US008124071B2

(12) United States Patent
Anversa et al.

(10) Patent No.: US 8,124,071 B2
(45) Date of Patent: Feb. 28, 2012

(54) METHODS OF REDUCING TRANSPLANT REJECTION AND CARDIAC ALLOGRAFT VASCULOPATHY BY IMPLANTING AUTOLOGOUS STEM CELLS

(75) Inventors: Piero Anversa, Boston, MA (US); Annarosa Leri, Boston, MA (US); Jan Kajstura, Brookline, MA (US)

(73) Assignee: New York Medical College, Valhalla, NY (US)

( * ) Notice: Subject to any disclaimer, the term of this patent is extended or adjusted under 35 U.S.C. 154(b) by 509 days.

(21) Appl. No.: 12/325,373

(22) Filed: Dec. 1, 2008

(65) Prior Publication Data

US 2009/0169525 A1 Jul. 2, 2009

Related U.S. Application Data

(60) Provisional application No. 60/991,499, filed on Nov. 30, 2007.

(51) Int. Cl.
*A61K 35/34* (2006.01)
*A61K 38/19* (2006.01)
(52) U.S. Cl. ........................ 424/93.7; 424/93.1; 435/325
(58) Field of Classification Search .................. 424/93.1, 424/93.7; 435/325
See application file for complete search history.

(56) References Cited

U.S. PATENT DOCUMENTS

| 5,434,134 | A | 7/1995 | Gluckman et al. |
|---|---|---|---|
| 5,908,782 | A | 6/1999 | Marshak et al. |
| 6,036,972 | A | 3/2000 | Nakamura et al. |
| 6,387,369 | B1 | 5/2002 | Pittenger et al. |
| 2003/0054973 | A1 | 3/2003 | Anversa |
| 2004/0258669 | A1 | 12/2004 | Dzau et al. |
| 2005/0170506 | A1 | 8/2005 | Sayre et al. |
| 2006/0239983 | A1 | 10/2006 | Anversa |
| 2006/0263337 | A1 | 11/2006 | Maziarz et al. |
| 2007/0054397 | A1 | 3/2007 | Ott et al. |
| 2009/0143296 | A1 | 6/2009 | Anversa |
| 2009/0148421 | A1 | 6/2009 | Anversa et al. |
| 2009/0157046 | A1 | 6/2009 | Anversa |
| 2009/0162329 | A1 | 6/2009 | Anversa et al. |
| 2009/0180998 | A1 | 7/2009 | Anversa et al. |

FOREIGN PATENT DOCUMENTS

| JP | 11-246433 | 9/1999 |
|---|---|---|
| WO | WO 92/11865 | 7/1992 |
| WO | WO 95/28174 | 10/1995 |
| WO | WO 99/45775 | 9/1999 |
| WO | WO 99/47163 A | 9/1999 |
| WO | WO 99/49015 A | 9/1999 |
| WO | WO 01/26694 | 4/2001 |
| WO | WO 01/34179 | 5/2001 |
| WO | WO 01/94420 | 12/2001 |
| WO | WO 02/13760 A | 2/2002 |
| WO | WO 03/033678 A | 4/2003 |
| WO | WO 03/103611 A | 12/2003 |
| WO | WO 2006/045331 A | 5/2006 |
| WO | WO 2007/100530 A1 | 9/2007 |
| WO | WO 2008/058216 A | 5/2008 |
| WO | WO 2009/073594 A | 6/2009 |

OTHER PUBLICATIONS

Beltrami et al., "Adult cardiac stem cells are multipotent and support myocardial regeneration", *Cell*, Sep. 19, 2003, 114(6):763-776.
International Search Report based on International Application PCT/US2008/085163 (Oct. 14, 2009).
Baba et al., "Flk1+ cardiac stem/progenitor cells derived from embryonic stem cells improve cardiac function in a dilated cardiomyopathy mouse model", *Cardiovascular Research*, 2007, 76:119-131.
Leri et al., "Heart failure and regenerative cardiology", *Regenerative Medicine*, 2006, 1(2):153-159.
International Search Report based on International Application PCT/US2008/085158 (Jan. 11, 2010).
Young et al., "Mesenchymal Stem Cells Reside Within the Connective Tissues of Many Organs." *Developmental Dynamics* 1995, vol. 202 pp. 137-144.
Nakamura et al., "Myocardial protection from ischemia/reperfusion injury by endogenous and exogenous HGF." *J. Clin. Invest.* 2000, vol. 106, pp. 1511-1519.
Yamamura et al., "IGF-I differentially regulates Bcl-xL and Bax and confers myocardial protection in the rat heart." *Am. J. Physiol. Heart Circ. Physiol.* 2001, vol. 280, pp. H1191-H1200.
Segers et al., "Stem-cell therapy for cardiac disease." *Nature* 2008, vol. 451, pp. 937-942.
International Search Report Based on International Application No. PCT/US08/085108 (Apr. 28, 2009).
International Search Report Based on International Application No. PCT/US08/084877 (Apr. 7, 2009).
Torella et al., "Biological properties and regenerative potential, in vitro and in vivo, of human cardiac stem cells isolated from each of the four chambers of the adult human heart" Circulation, vol. 114, No. 18, suppl: 87, 2006.
Bearzi et al., "Human cardiac stem cells" Proc. Natl. Acad. Sci. USA, vol. 104: 14068-14073, 2007.
Messina et al., "Isolation and expansion of adult cardiac stem cells from human and murine heart" Circulation Research, vol. 95: 911-921, 2004. Linke et al., "Stem cells in the dog heart are self-renewing, clonogenic, and multipotent and regenerate infarcted myocardium, improving cardiac function" Proc. Natl. Acad. Sci. USA, vol. 102: 8966-8971, 2005.
Beltrami et al., "Adult cardiac stem cells are multipotent and support myocardial regeneration" Cell, vol. 114: 763-766, 2003.
Dawn et al., "Cardiac stem cells delivered intravasculary traverse the vessel barrier, regenerate infarcted myocardium, and improve cardiac function" Proc. Natl. Acad. Sci. USA, vol. 102: 3766-3771, 2005.
Urbanek et al., "Intense myocyte formation from cardiac stem cells in human cardiac hypertophy" Proc. Natl. Acad. Sci. USA, vol. 100: 10440-10445, 2003.
Anversa et al., "Life and death of cardiac stem cells—A paradigm shift in cardiac biology" Circulation, vol. 113: 1451-1463, 2006.

(Continued)

*Primary Examiner* — Taeyoon Kim
(74) *Attorney, Agent, or Firm* — Cooley LLP

(57) ABSTRACT

The invention provides novel methods of reducing transplant rejection and cardiac allograft vasculopathy in humans by employing the implantation of autologous progenitor cells into the transplanted donor heart. The autologous progenitor cells can be vascular progenitor cells (VPCs) and/or myocyte progenitor cells (MPCs) isolated from the recipient's explanted heart. Alternatively, bone marrow progenitor cells (BMPCs) isolated from the recipient may also be used.

20 Claims, 29 Drawing Sheets

OTHER PUBLICATIONS

Urbanek et al., "Cardiac stem cells possess growth factor-receptor systems that after activation regenerate the infarcted myocardium, improving ventricular function and long-term survival" Circulation Research, vol. 97: 663-673, 2005.

Urbanek et al., "Myocardial regeneration by activation of multipotent cardiac stem cells in ischemic heart failure" Proc. Natl. Acad. Sci. USA, vol. 102: 8692-8697, 2005.

Sussman et al., "Myocardial aging and senescence: Where have the stem cells gone?" Annual Review of Physiology, vol. 66: 29-48, 2004.

Armandola, Written Opinion of International Search Authority for PCT/US08/084877, Apr. 2009.

Pêche et al., "Prolongation of Heart Allograft Survival by Immature Dendritic Cells Generated from Recipient Type Bone Marrow Progenitors", *American Journal of Transplantation*, Feb. 2005, vol. 5, No. 2, pp. 255-267.

Metcalfe et al., "Transplantation tolerance: gene expression profiles comparing allotolerance vs. allorejection", *International Immunopharmacology*, Jan. 2005, vol. 5, No. 1, pp. 33-39.

Orlic et al., "Mobilized bone marrow cells repair the infarcted heart, improving function and survival", Proc. Natl. Acad. Sci. USA, vol. 98: 10344-10349, 2001.

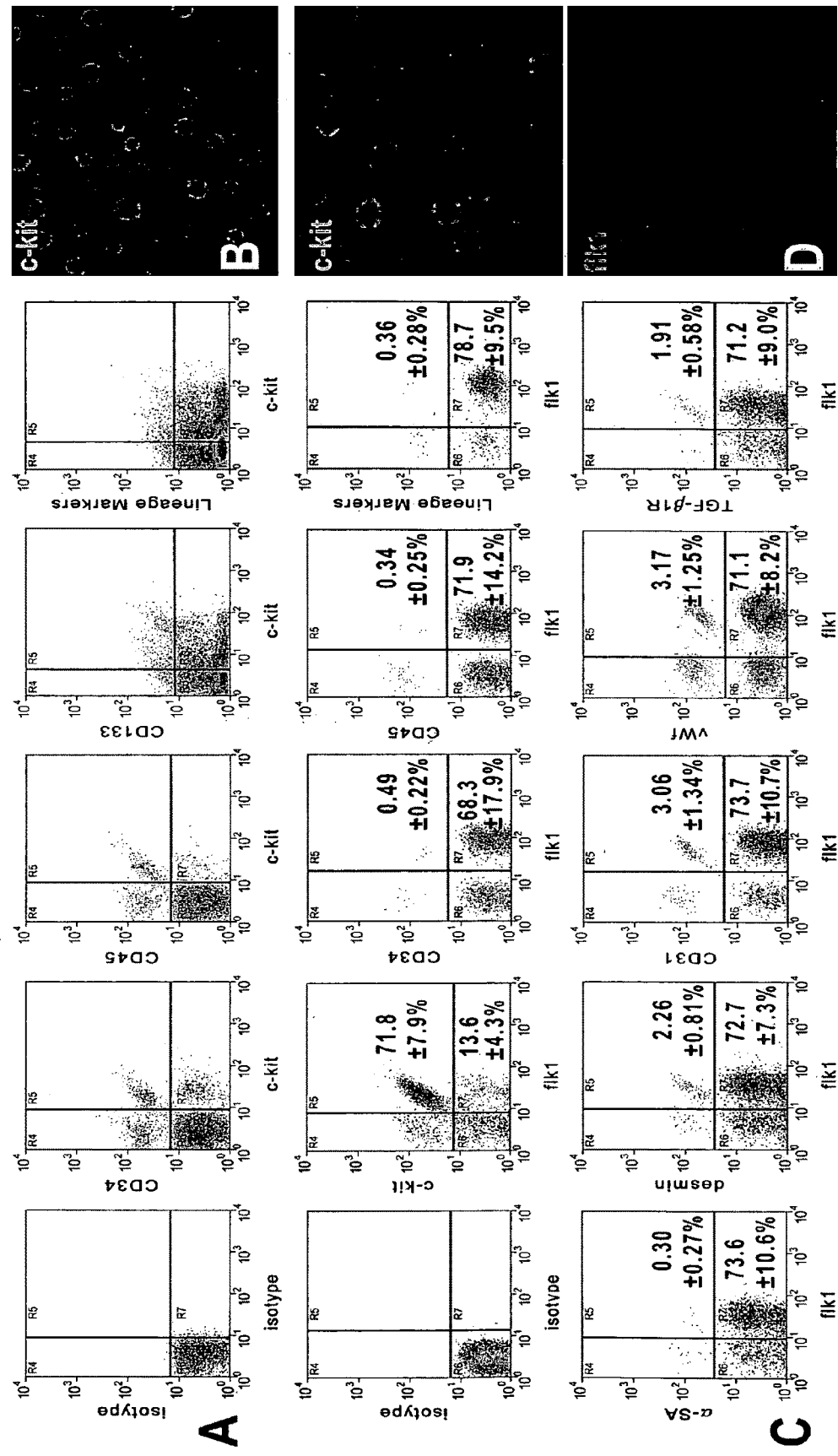
Figure 6 A-D

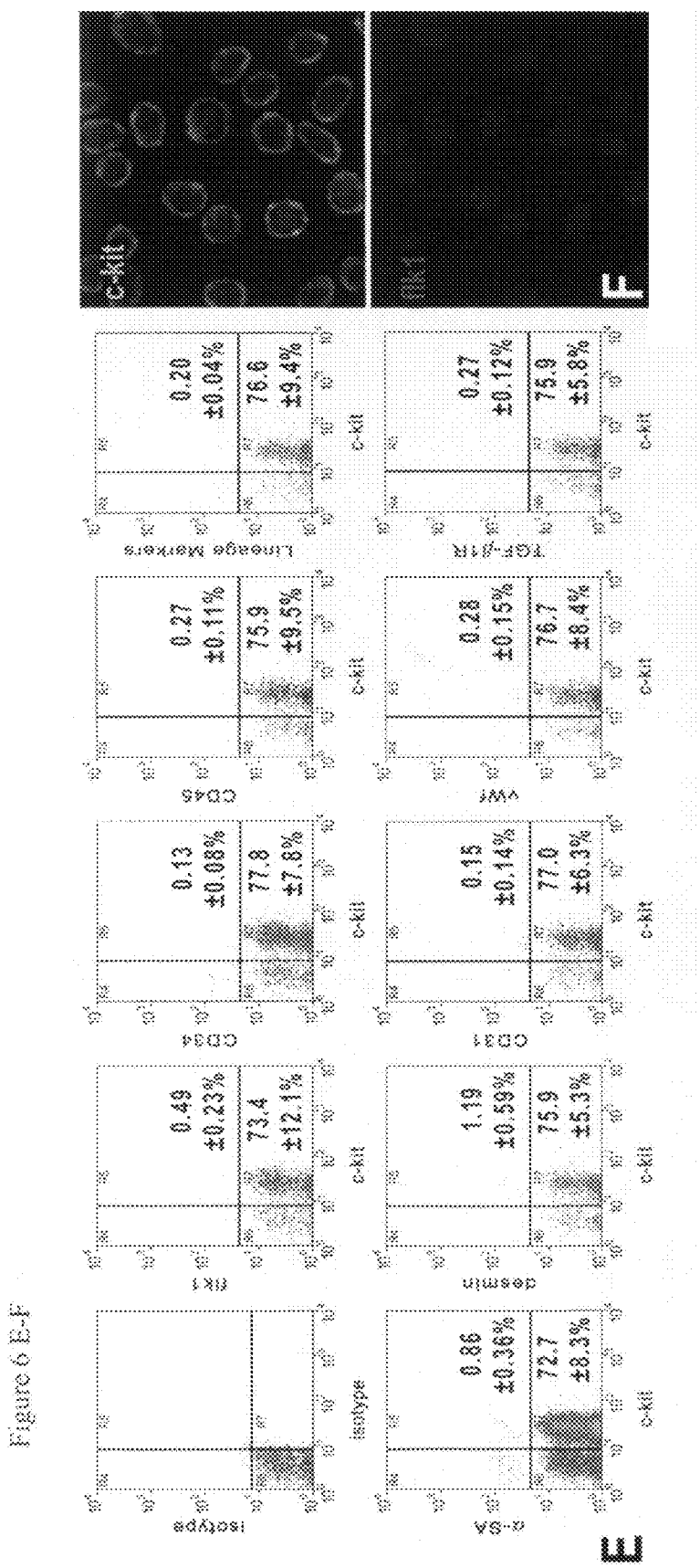
Figure 6 E-F

Figure 11A-F
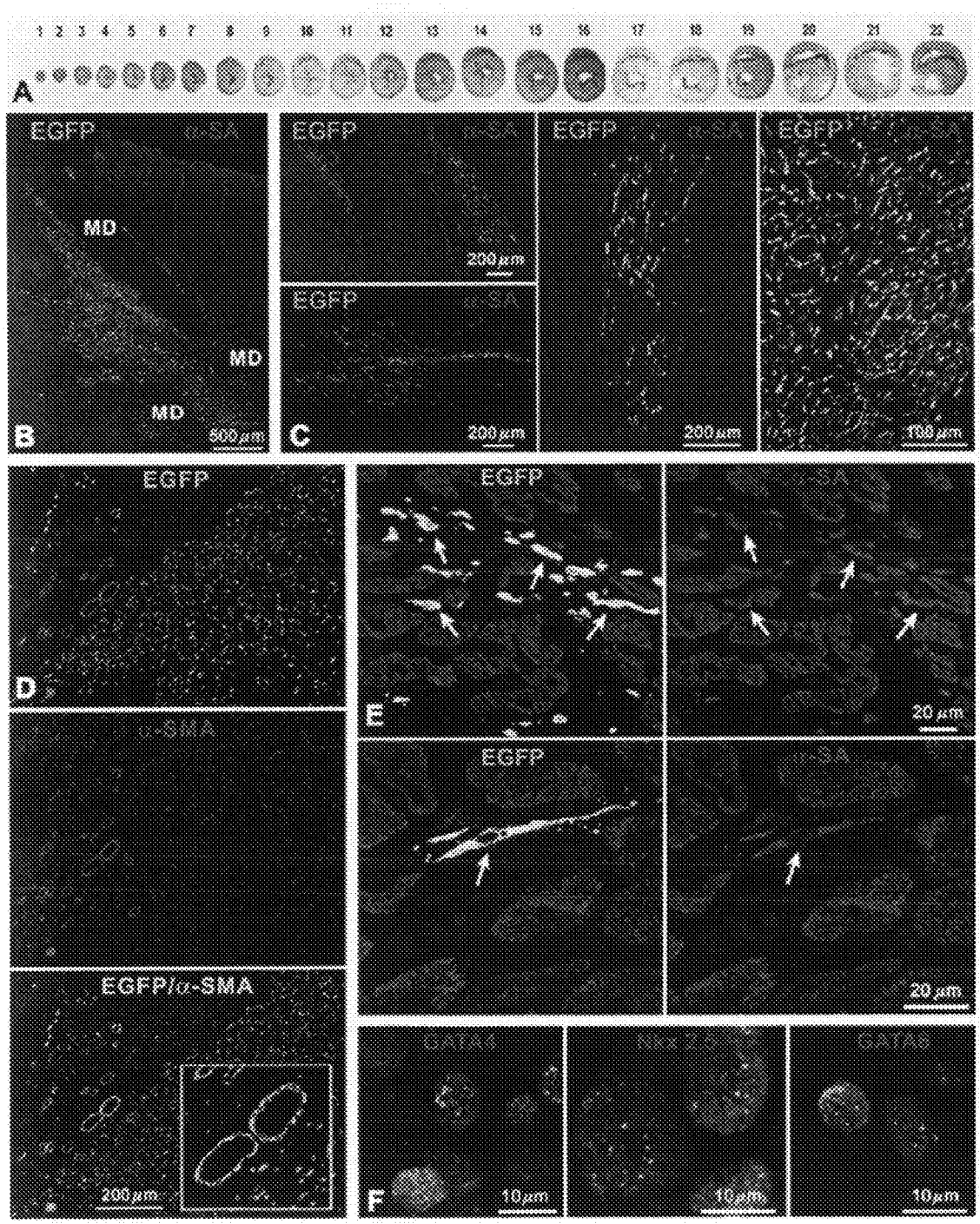

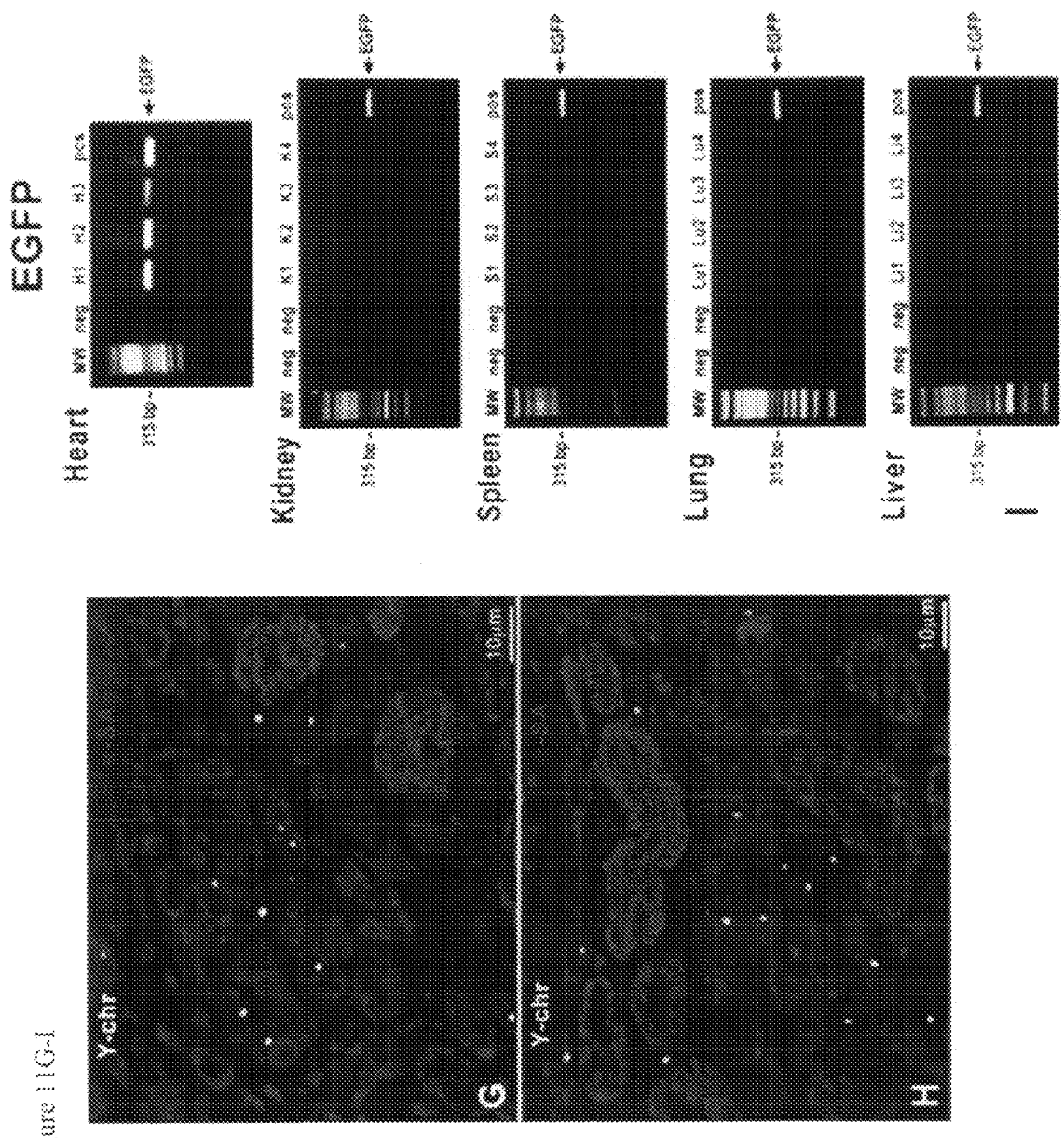

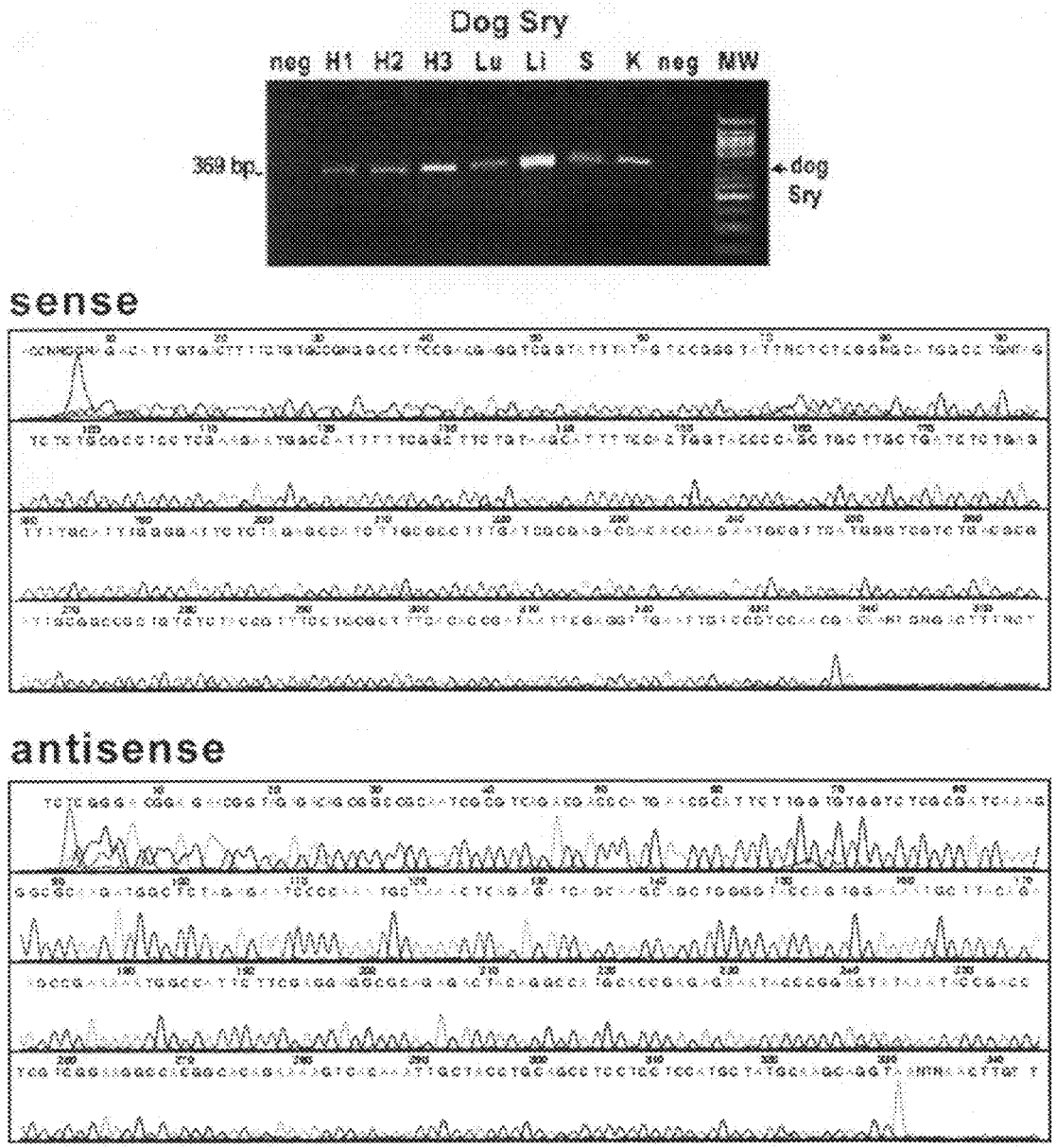

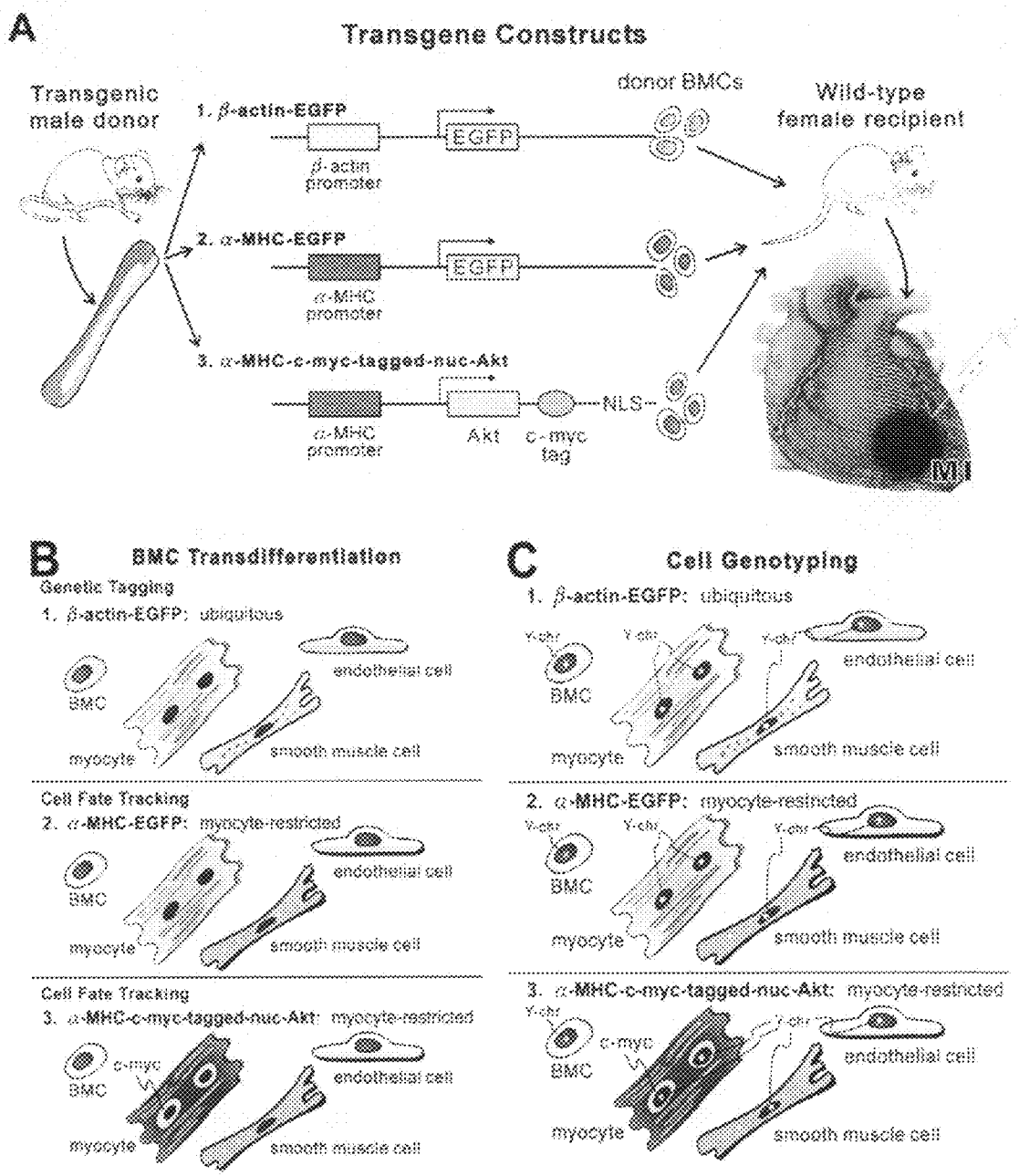

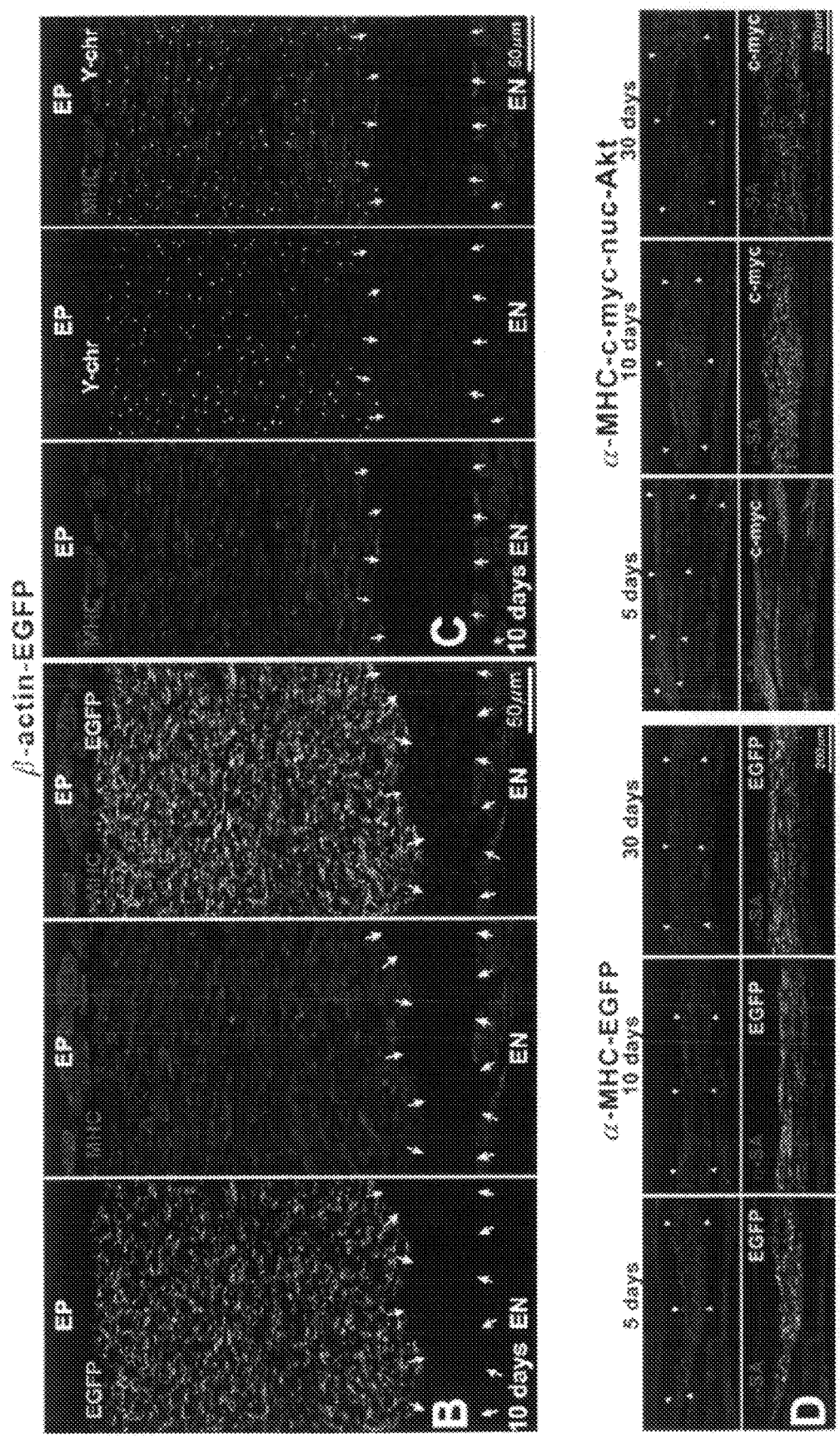
Figure 13 B-D

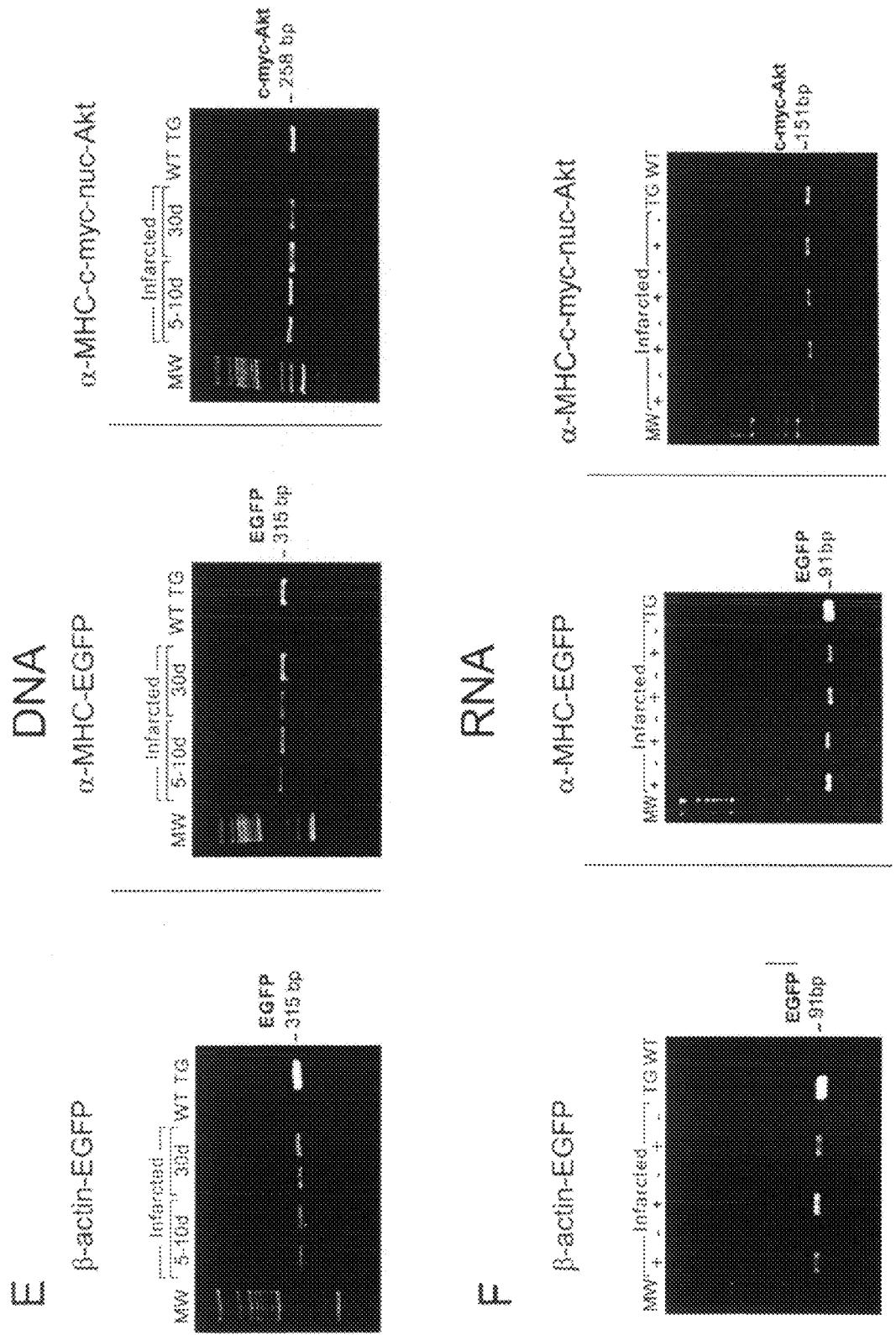
Figure 13 E-F

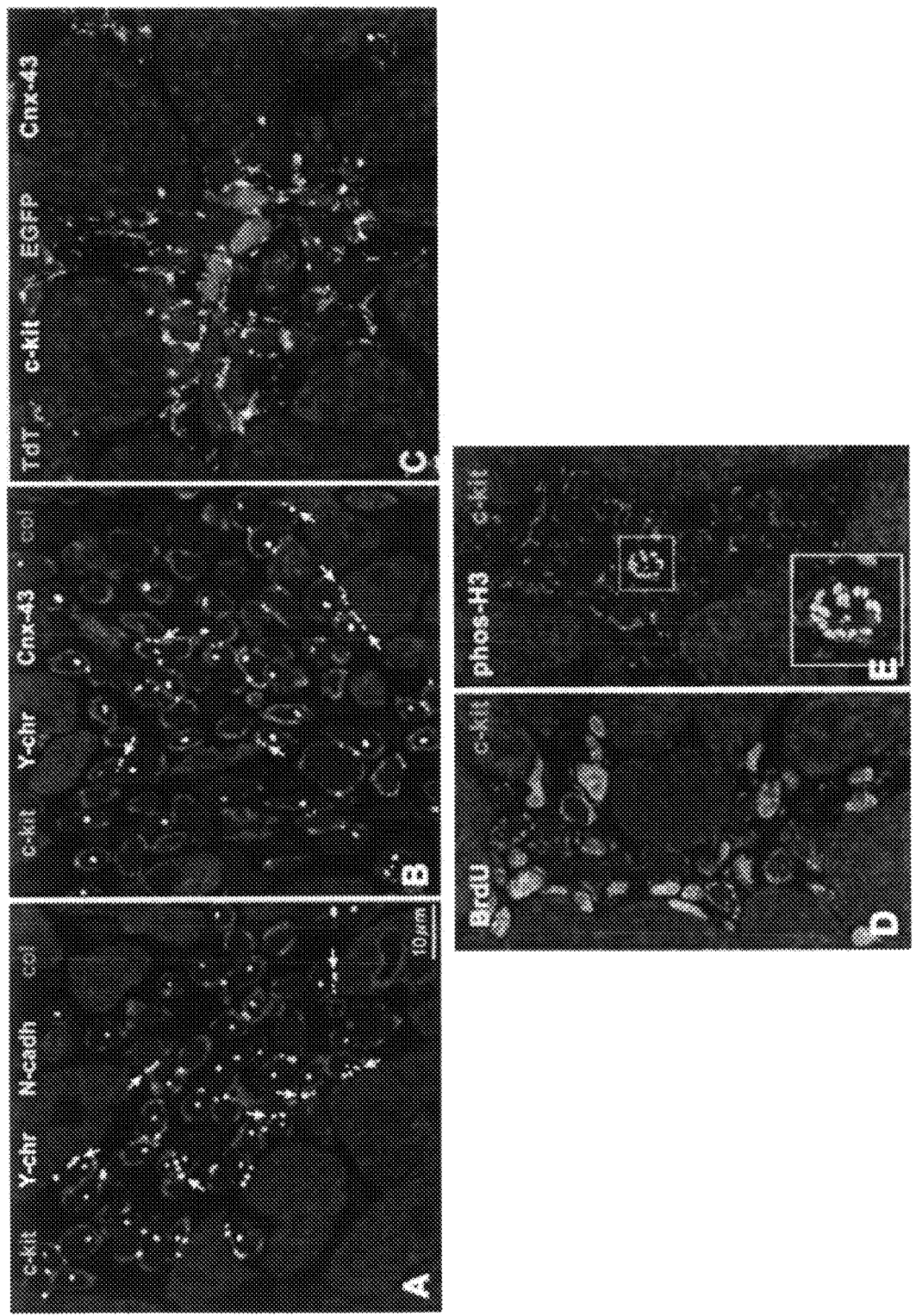

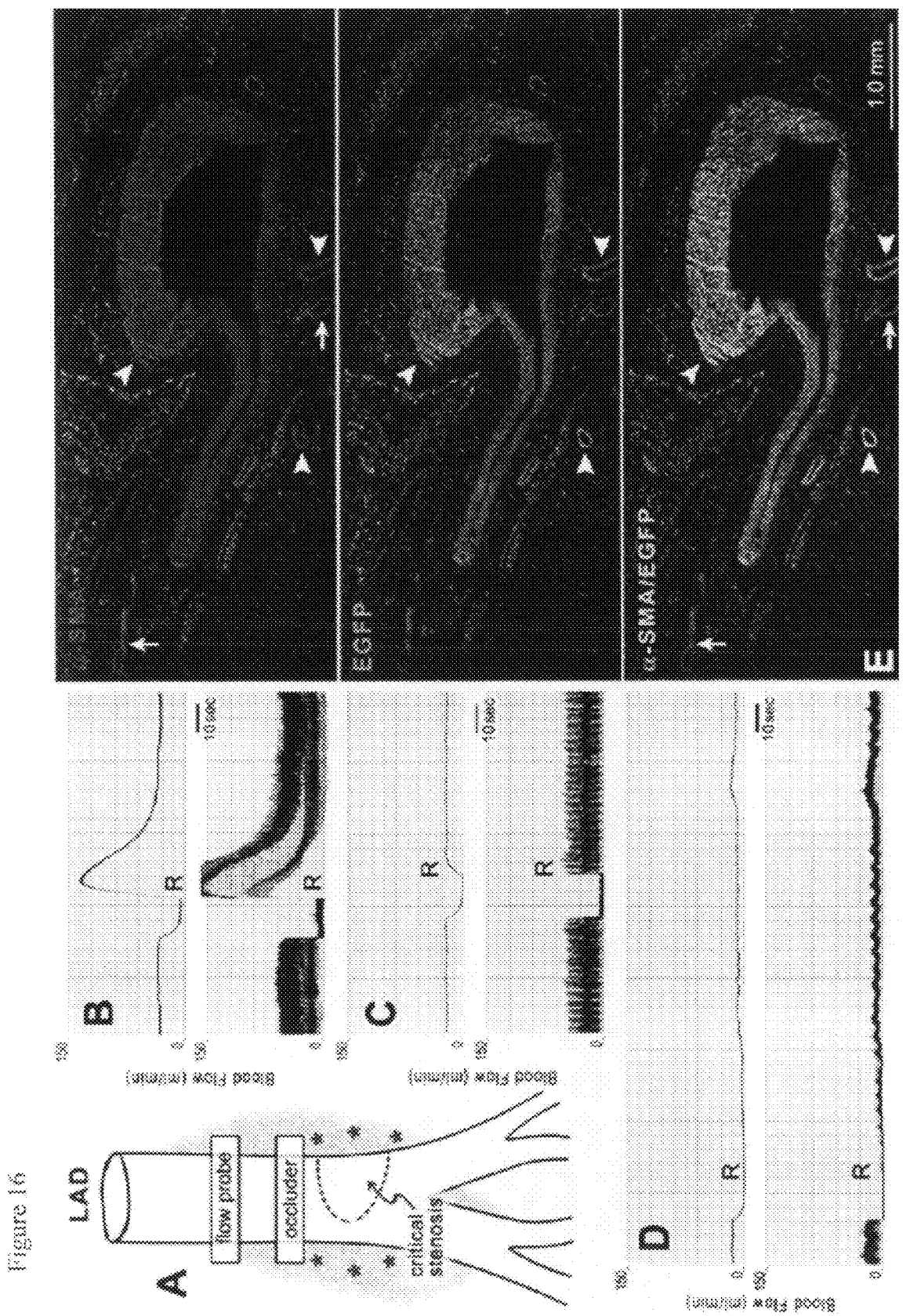

Figure 17A-B
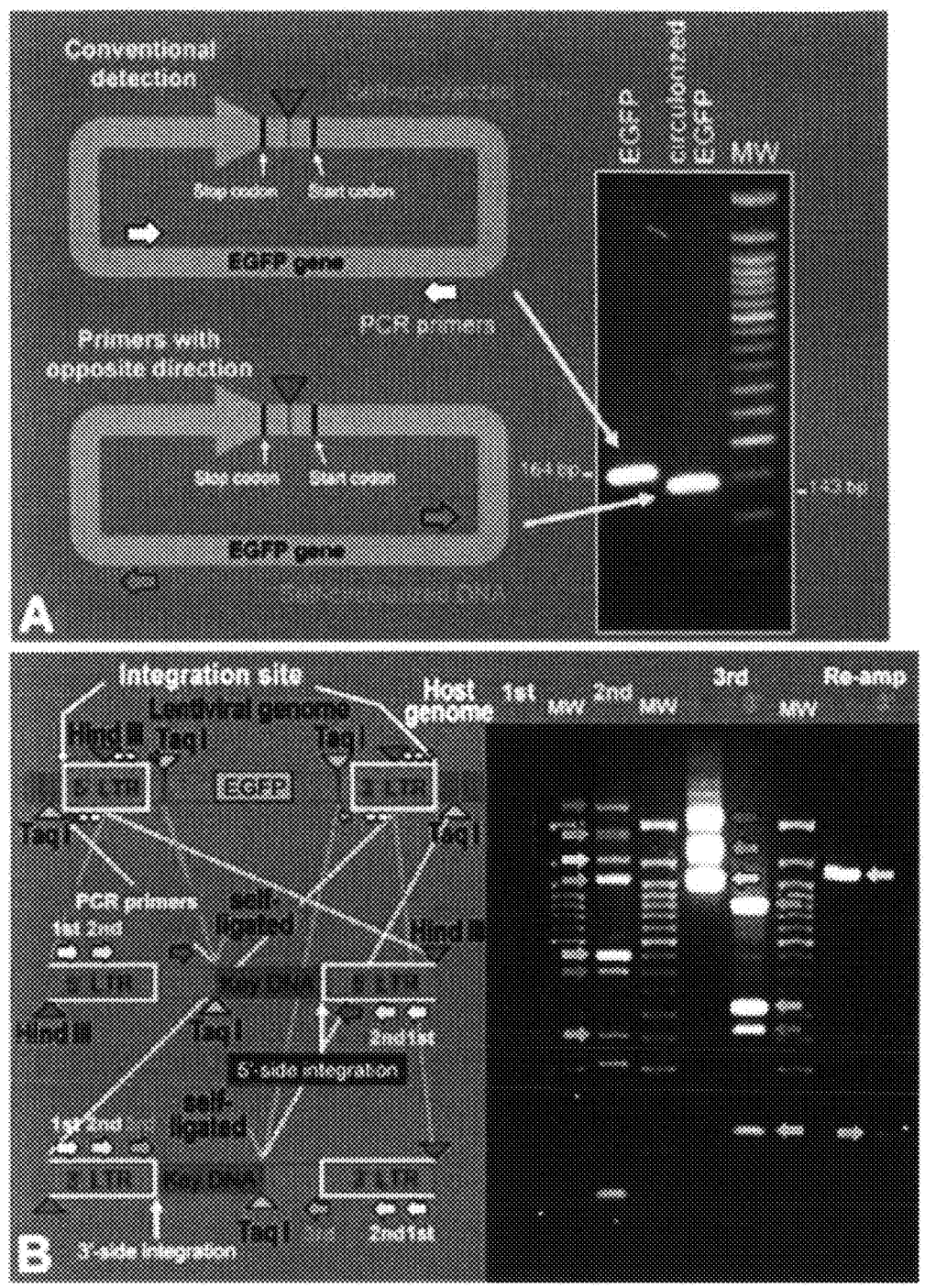

Figure 17C-D
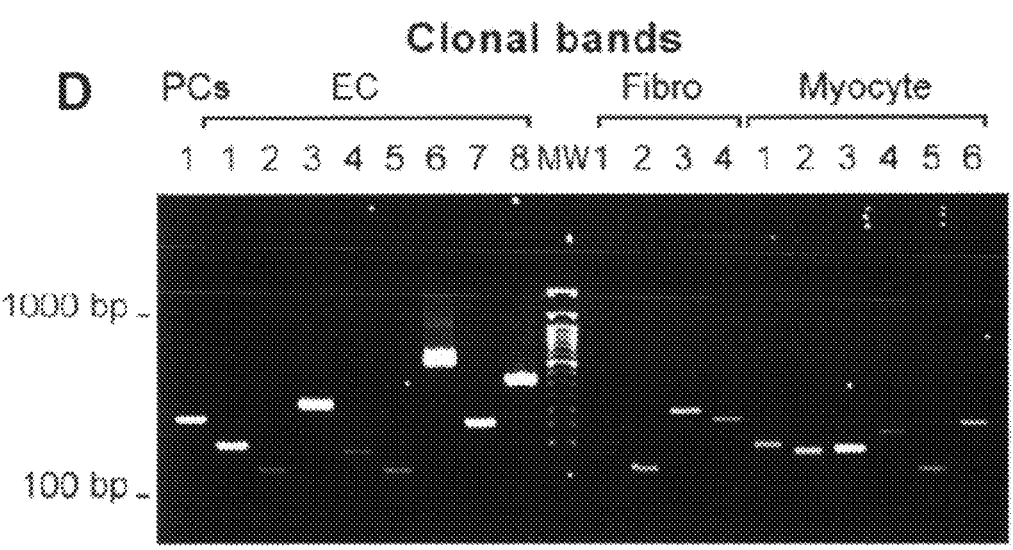

SEQUENCE LISTING

<160> NUMBER OF SEQ ID NOS: 16

<210> SEQ ID NO 1
<211> LENGTH: 26
<212> TYPE: DNA
<213> ORGANISM: Canis familiaris

<400> SEQUENCE: 1
cgttggacgg acaattcaac ctcgaa            26

<210> SEQ ID NO 2
<211> LENGTH: 26
<212> TYPE: DNA
<213> ORGANISM: Canis familiaris

<400> SEQUENCE: 2
acctgcttgc atagcatgga ggagga            26

```
<210> SEQ ID NO 3
<211> LENGTH: 354
<212> TYPE: DNA
<213> ORGANISM: Canis familiaris
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t
<220> FEATURE:
<221> NAME/KEY: misc_feature
<222> LOCATION: (342)..(342)
<223> OTHER INFORMATION: n is a, c, g, or t
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (352)..(352)
<223> OTHER INFORMATION: n is a, c, g, or t

<400> SEQUENCE: 3
accnnggnag acattgtgac ttttctgtgc cgnggccttc cgacgaggtc ggtatttata      60
gtccgggtat tnctctcggn gcatggcctg ntagtctctg cgcctcctcg aagaatggcc     120 attttcggc ttctgtaagc attttccact ggtacccag ctgcttgctg atctctgagt      180
tttgcatttg gggattctct agagccatct tgcgcctttg atcgcgagac cacaccaaga     240
atgcgttcat gggtcgtctg acgcgattgc ggccgctgtc tctaccgttt cctccgcttt     300
cacaccgata attcgaggtt gaattgtccg tccaacgaca antgngactt tnct          354

<210> SEQ ID NO 4
<211> LENGTH: 344
<212> TYPE: DNA
<213> ORGANISM: Canis familiaris
<220> FEATURE:
<221> NAME/KEY: misc_feature
<222> LOCATION: (334)..(334)
<223> OTHER INFORMATION: n is a, c, g, or t
<220> FEATURE:
<221> NAME/KEY: misc_feature
<222> LOCATION: (336)..(336)
<223> OTHER INFORMATION: n is a, c, g, or t

<400> SEQUENCE: 4
tctcgggacg gagaacggta gagacagcgg ccgcaatcgc gtcagacgac ccatgaacgc      60
attcttggtg tggtctcgcg atcaaagggc gcaagatggc tctagagaat ccccaaatgc     120
aaaactcaga gatcagcaag cagctggggt accagtggaa aatgcttaca gaagccgaaa     180
aatggccatt cttcgaggag gcgcagagac tacaggccat gcaccgagag aaatacccgg     240
actataaata ccgacctcgt cggaaggcca cggcacagaa aagtcacaaa ttgctacctg     300
```
cagcctcctc ctccatgcta tgcaagcagg taantnaact tgtt                    344

<210> SEQ ID NO 5
<211> LENGTH: 285
<212> TYPE: DNA
<213> ORGANISM: Mus musculus
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (282)..(282)
<223> OTHER INFORMATION: n is a, c, g, or t
<220> FEATURE:
<221> NAME/KEY: misc_feature
<222> LOCATION: (284)..(284)
<223> OTHER INFORMATION: n is a, c, g, or t

<400> SEQUENCE: 5
ctggggngnc atctggtgag ctggaggcga cgtaaacggc cacaagttca gcgtgtccgg      60
cgagggcgag ggcgatgcca cctacggcaa gctgaccctg aagttcatct gcaccaccgg     120
caagctgccc gtgccctggc ccaccctcgt gaccaccctg acctacggcg tgcagtgctt     180
caagccgcta ccccgaccac atgaagcagc acgacttctt caagtccgcc atgcccgaag     240
gctacgtcca ggagcgcacc atcttcttca agggacgacg gnana                     285

<210> SEQ ID NO 6
<211> LENGTH: 288
<212> TYPE: DNA
<213> ORGANISM: Mus musculus
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (282)..(283)
<223> OTHER INFORMATION: n is a, c, g, or t
<220> FEATURE:
<221> NAME/KEY: misc_feature
<222> LOCATION: (287)..(287)
<223> OTHER INFORMATION: n is a, c, g, or t

<400> SEQUENCE: 6
cccntggagn ccttgggcan gcggacttna agaagtcgtg ctgcttcatg tggtcggggt      60
agcggctgaa gcactgcacg ccgataggtt caggggtggt cacgagggtg ggccagggca    120
cgggcagctt gccggtggtg caaatgaact tcagggtcag cttgccgtag gtggcatcgc    180
cctcgccctc gccggacacg ctgaacttgt ggccgtttac gtcgccgtcc agctcgacca    240
ggatgggcac caccccggtg aacagctcct cgccctgctc annaaana                 288

```
<210> SEQ ID NO 7
<211> LENGTH: 284
<212> TYPE: DNA
<213> ORGANISM: Mus musculus
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (281)..(283)
<223> OTHER INFORMATION: n is a, c, g, or t

<400> SEQUENCE: 7 ctgggggnc atctggtgac tggaggcgac gtaaacggcc acaagttcag cgtgtccggc      60
gagggcgagg gcgatgccac ctacggcaag ctgaccctga agttcatctg caccaccggc     120
aagctgcccg tgccctggcc caccctcgtg accaccctga cctacggcgt gcagtgcttc    180
agccgctacc ccgaccacat gaagcagcac gacttcttca gtccgccat gcccgaaggc     240 tacgtccagg agcgcaccat cttcttcaag gacgacggna nnna                      284

<210> SEQ ID NO 8
<211> LENGTH: 291
<212> TYPE: DNA
<213> ORGANISM: Mus musculus
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (285)..(285)
<223> OTHER INFORMATION: n is a, c, g, or t
<220> FEATURE:
<221> NAME/KEY: misc_feature
<222> LOCATION: (291)..(291)
<223> OTHER INFORMATION: n is a, c, g, or t

<400> SEQUENCE: 8
cccgngggng nccttgggca tggcggactt gaagaagtcg tgctgcttca tggtggtcgg      60
ggtagcggct gaagcactgc acgccgatag gtcagggtgg tcacgagggt gggccagggc    120
acgggcagct tgccggtggt gcanatgaac ttcagggtca gcttgccgta ggtggcatcg    180
ccctcgccct cgccggacac gctgaacttg tggccgttta cgtcgccgtc cagctcgacc    240
aggatgggca ccaccccggt gaacagctcc tcgcccttgc tcacnaaaaa n             291

<210> SEQ ID NO 9
<211> LENGTH: 226
<212> TYPE: DNA
<213> ORGANISM: Mus musculus
<220> FEATURE:
<221> NAME/KEY: misc_feature
<222> LOCATION: (1)..(1)
<223> OTHER INFORMATION: n is a, c, g, or t
```

```
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t

<400> SEQUENCE: 9
nacgccgnct gatcagatga cagcatggta gtgtgtggac agtgagcgga ggccgcactt     60
cccccanctt ctcctactca gccaggtggc acagccaaac gggcggccgc agatccaaaa    120
aagaagagaa aggtagatcc aaaaaagaag agaaaggtag atccaaaaaa gaagagaaag    180
gtagatacgg ccgcagaaca aaaactcatc tcagaagagg atctga                   226

<210> SEQ ID NO 10
<211> LENGTH: 223
<212> TYPE: DNA
<213> ORGANISM: Mus musculus
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: misc_feature
<222> LOCATION: (121)..(121)
<223> OTHER INFORMATION: n is a, c, g, or t
<220> FEATURE:
<221> NAME/KEY: misc_feature
<222> LOCATION: (222)..(222)
<223> OTHER INFORMATION: n is a, c, g, or t

<400> SEQUENCE: 10
tntggcgtac acctttctct tctttttttgg atctacctttt ctcttctttt ttggatctac   60
cttnctcttc tttttttgaat ctgcggccgc ccgtttggct gtgccactgg ctgagtagga  120
naactggggg aagtgcggcc tccgctcact gtccacacac tccatgctgt catcttgatc   180
aggcggcgtg atggtgatca tctgagctgt gaactcctca tna                     223

<210> SEQ ID NO 11
<211> LENGTH: 96
<212> TYPE: DNA
<213> ORGANISM: Mus musculus
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t
```

<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (85)..(91)
<223> OTHER INFORMATION: n is a, c, g, or t

<400> SEQUENCE: 11
tntgggcncn nanatccgtg ggggcacagg gcctnggann tcaacctac caacaggccc    60 acaacggntc gtatatcatt gggannnnnn ncccctt    96

<210> SEQ ID NO 12
<211> LENGTH: 95
<212> TYPE: DNA
<213> ORGANISM: Mus musculus
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
<222> LOCATION: (84)..(90)
<223> OTHER INFORMATION: n is a, c, g, or t

<400> SEQUENCE: 12
tntgggcncn nanatccgtg ggggcacagg cctnggannt acaacctacc aacaggccca    60
caacggntcg tatatcattg ggannnnnnn ccctt    95

<210> SEQ ID NO 13
<211> LENGTH: 72
<212> TYPE: DNA
<213> ORGANISM: Mus musculus
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 13
gannncaccc ccgnggggca cngcctggag tcaacctacc aacagcccac caaccgttcc    60
tatatcatgg ga                                                          72

<210> SEQ ID NO 14
<211> LENGTH: 76
<212> TYPE: DNA
<213> ORGANISM: Mus musculus
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (74)..(74)
<223> OTHER INFORMATION: n is a, c, g, or t

<400> SEQUENCE: 14
gatttgntcn gccngtgggc ccnggantnt tngccggctc cctcctngga agttcgantg    60 cccttttcagn catnaa                                                    76

<210> SEQ ID NO 15
<211> LENGTH: 121
<212> TYPE: DNA
<213> ORGANISM: Mus musculus
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 15
ggncacgggc ggncgcgatc caaaaagaag agaagggta gatccaaaaa agaagagaaa    60
gggtagatcc aaaaaagaag agaaggtag atacggccgc agaacaaaaa ctcatctcag   120
a                                                                   121

```
<210> SEQ ID NO 16
<211> LENGTH: 121
<212> TYPE: DNA
<213> ORGANISM: Mus musculus
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (9)..(10)
<223> OTHER INFORMATION: n is a, c, g, or t

<400> SEQUENCE: 16
cgnnncttnn ctcttttttg gatctaccttt tctcttcttt tttggatcta cctttctctt        60
cttttttgga tctgcggccg cccgatttgg ctgtgccact ggctgagtag gagaactggg       120
a                                                                      121
```

METHODS OF REDUCING TRANSPLANT REJECTION AND CARDIAC ALLOGRAFT VASCULOPATHY BY IMPLANTING AUTOLOGOUS STEM CELLS

CROSS REFERENCE TO RELATED APPLICATIONS

This application claims the benefit of U.S. Provisional Application No. 60/991,499, filed Nov. 30, 2007, which is herein incorporated by reference in its entirety.

FIELD OF THE INVENTION

The present invention relates generally to the field of cardiology, and more particularly relates to methods of reducing transplant rejection by implanting cardiac stem cells or bone marrow progenitor cells isolated from the recipient into the donor heart.

BACKGROUND OF THE INVENTION

The interaction between donor and recipient cells after transplantation has received great attention in an attempt to identify the basis of rejection and graft-versus-host disease (1-5). Cell migration from the allograft to the recipient results in systemic chimerism (6-8), and cell migration from the host to the transplanted organ results in chimerism of the organ (9, 10). Chimerism can be detected easily after sex-mismatched organ transplantation with FISH for the Y-chromosome (11-13) and several studies on cardiac chimerism have provided consistent results concerning the migration of progenitor cells (PCs) from the host to the graft (14-26). The sex-mismatched transplants make it possible to document and evaluate quantitatively a process that is part of cardiac homeostasis but it is otherwise not measurable in humans (27). After homing, host PCs undergo replication and differentiation, generating mature myocytes and vascular structures in the transplanted heart (14). Although there is little disagreement among authors in terms of the occurrence of this phenomenon, the magnitude of cardiac chimerism varies significantly in different reports (14-27). This discrepancy involves mostly ventricular myocytes and to a much lesser extent coronary vessels. For myocytes, the published values range from as high as 18% (14) to as low as 0.02% (15). Conversely, levels of endothelial cell chimerism and vessel formation have been shown to involve up to 22% of the coronary circulation (14, 25). In spite of these differences which previously have been discussed (27-31), the regenerated cardiomyocytes and coronary arterioles together with capillary profiles have normal morphology and are distributed predominantly in areas of intact donor myocardium (14). These data provide evidence that adult PCs contribute to the formation of solid-organ tissue cells (32-36), but leave unanswered the question whether the migrating cells arise from precursors in the atrial remnants of the recipient's heart or translocate from the recipient's bone marrow through the circulation to the transplanted organ (37).

After the first year, chronic loss of graft function (71) is the predominant cause of mortality in cardiac transplant patients (72). Inflammation and immune-mediated reactions (73) are responsible for the reduced sensitivity of myocytes to catecholamines, alterations in surface receptors, defects in ion-channels and depressed contractility (74, 75). Graft dysfunction is characterized by changes in the coronary arteries by a process termed cardiac allograft vasculopathy (CAV) (76). Although a causal relationship between reduced graft function and CAV remains to be demonstrated, the progressive occlusion of coronary vessels and ischemic myocardial damage are the critical mechanisms of graft failure (77-81). Several risk factors for CAV have been identified; they include systemic hypertension, body mass index, advanced donor age and number of rejection episodes (82-90). CAV inexorably leads to a chronic ischemic myopathy and death (91); 75% of transplant patients suffer from CAV one year following surgery (92, 93). Histologically, four etiologic factors have been considered: (a) intimal thickening mediated by migration of smooth muscle cells and/or proliferation of resident or migratory smooth muscle cells (94, 95); (b) infiltration of the intima by leukocytes recruited in response to injury or inflammation (96, 97); (c) accumulation of T lymphocytes and macrophages which generate a peri-vascular cuffing, local injury and irreversible damage, commonly defined as constrictive vascular remodeling (98-103); and (d) dynamic reduction in vessel diameter sustained by abnormalities in vasoconstriction and dilation (104-107). CAV differs from typical atherosclerotic lesions (108). With CAV, lesions are concentric and diffuse rather than eccentric and focal and extend beyond the large arteries reaching the penetrating smaller ramifications. Because of its diffuse distribution, CAV cannot be corrected with bypass surgery, angioplasty or stenting (72). In some cases, both types of lesions are present.

The cause of graft coronary artery disease remains elusive although immune and non-immune mechanisms have been implicated (70, 109). Controversy exists as to the origin of the proliferating cells present in CAV (110). It has been proposed that thickening of the intima is dictated by accumulation of recipient cells which derive from a pool of circulating PCs that differentiate locally into endothelial cells (ECs) and smooth muscle cells (SMCs) (111). Endothelial progenitor cells (EPCs) from the recipient may home to the intima and differentiate into endothelial-like cells (112-118) contributing to the vascular lesion. Similarly, SMC precursors could be recruited from the circulation and participate in vessel pathology (119-124). The results of cardiac chimerism in humans, however, question the negative effects of PCs of recipient origin (14, 15, 19, 20, 23, 25). There is general agreement that these cells contribute minimally to CAV and the formed coronary vasculature is structurally intact with no signs of atherosclerosis. The opposite view is supported by animal studies in which the orthotopic aorta allograft has been employed (117, 125, 126). This model has limitations; the aorta is structurally different from the coronary arteries and its intramural branches (127-130). Most importantly, medial necrosis is present in the orthotopic aorta allograft (125, 126, 131-133) while it is never observed in human CAV. These differences raise questions on the appropriateness of this model for graft vascular disease. At present, a few effective pharmacological therapies have been applied to the treatment of CAV. The HMG-CoA reductase inhibitors and the cell cycle inhibitor rapamycin reduce neointimal proliferation, myocardial infarction, the need for revascularization and death (134, 135). These therapies are extremely valuable but only delay the progression of CAV in the transplanted heart. Cell therapy with the formation of coronary vessels (47, 48, 51-53, 56, 57, 59, 64, 65) may increase coronary blood flow (CBF), decrease coronary resistance and enhance tissue oxygenation (136). The problem in need of resolution involves the identification and characterization of PCs that can form large conductive coronary arteries and their distal branches together with a large quantity of cardiomyocytes (59, 64, 137).

SUMMARY OF THE INVENTION

The present invention provides a novel approach to reduce transplant rejection and cardiac allograft vasculopathy in humans. The inventors have discovered distinct classes of progenitor cells that create immunocompatible myocardium within the non-immunocompatible transplanted heart and improve myocardial performance, reduce morbidity-mortality and ultimately prolong life.

In some embodiments, the methods of the instant invention comprise delivery of cardiac progenitor cells isolated from the recipient into the transplanted donor heart, wherein the progenitor cells engraft and differentiate into myocytes, smooth muscle cells, and endothelial cells resulting in the formation of functionally-competent, immunocompatible myocardium and coronary vessels. Thus, the present invention provides a method of reducing an immune response to a transplanted donor heart in a subject. In one embodiment, the method comprises obtaining myocardial tissue from the subject's explanted heart; extracting cardiac progenitor cells from said myocardial tissue; expanding said cardiac progenitor cells in culture; and administering said cardiac progenitor cells to the transplanted donor heart, wherein said cardiac progenitor cells generate immunocompatible myocardium and immunocompatible myocardial vessels following their administration, thereby reducing the immune response to said transplanted donor heart. In another embodiment, the cardiac progenitor cells are separated into vascular progenitor cells and myocyte progenitor cells prior to administration. Vascular progenitor cells may be c-kit positive and flk1 positive, and differentiate into immunocompatible smooth muscle cells and endothelial cells. Myocyte progenitor cells may be c-kit positive and flk1 negative and differentiate into immunocompatible cardiomyocytes. In another embodiment, the method further comprises activating the cardiac progenitor cells prior to administration by exposing the cells to one or more cytokines.

In another embodiment of the invention, the method of reducing an immune response to a transplanted donor heart in a subject comprises obtaining a bone marrow specimen from the subject; extracting adult bone marrow progenitor cells from said specimen; expanding said bone marrow progenitor cells in culture; and administering said bone marrow progenitor cells to the transplanted donor heart, wherein said bone marrow progenitor cells generate immunocompatible myocardium and immunocompatible myocardial vessels following their administration, thereby reducing the immune response to said transplanted donor heart. In some embodiments, the bone marrow progenitor cells are c-kit positive. In another embodiment, the bone marrow progenitor cells are administered immediately after transplantation. In another embodiment, the bone marrow progenitor cells differentiate into immunocompatible endothelial cells, smooth muscle cells, and cardiomyocytes.

In another embodiment of the invention, the method further comprises extracting cardiac progenitor cells from said subject's explanted heart; separating said cardiac progenitor cells into vascular progenitor cells and myocyte progenitor cells; and administering said vascular progenitor cells and myoctye progenitor cells to the transplanted donor heart. The vascular progenitor cells and myoctye progenitor cells may be administered by multiple administrations after transplantation. The multiple administrations may occur at a set interval after administration of the bone marrow progenitor cells.

In another embodiment of the invention, the method of reducing an immune response to a transplanted donor heart in a subject comprises obtaining myocardial tissue from the subject's explanted heart; extracting cardiac myocyte progenitor cells from said myocardial tissue; expanding said myocyte progenitor cells in culture; and administering said myocyte progenitor cells to the transplanted donor heart, wherein said myocyte progenitor cells generate immunocompatible myocardium following their administration, thereby reducing the immune response to said transplanted donor heart. The myocyte progenitor cells may be c-kit positive and flk1 negative. In one embodiment, the myocyte progenitor cells differentiate into immunocompatible cardiomyocytes.

The present invention also provides a method of reducing cardiac allograft vasculopathy in a subject who has received a transplanted donor heart. In one embodiment, the method comprises obtaining myocardial tissue from the subject's explanted heart; extracting cardiac vascular progenitor cells from said myocardial tissue; expanding said vascular progenitor cells in culture; and administering said vascular progenitor cells to the transplanted donor heart, wherein said vascular progenitor cells generate immunocompatible coronary vasculature, thereby repairing/and or regenerating the non-immunocompatible coronary arteries of the donor heart. The vascular progenitor cells may be c-kit positive and flk1 positive. In one embodiment, the vascular progenitor cells differentiate into immunocompatible endothelial cells and smooth muscle cells.

In some embodiments, the methods described herein may further comprise administering to the subject an immunosuppressive therapy. The immunosuppressive therapy may be administered concurrently or subsequently to the administration of the progenitor cells to the donor heart. Preferably, the dose and frequency of a standard immunosuppressive therapy is reduced following the administration of one or more types of progenitor cells (e.g. bone marrow progenitor cells, vascular progenitor cells, or myocyte progenitor cells) to the donor heart.

BRIEF DESCRIPTION OF THE DRAWINGS

FIG. 6. PC classes. Freshly isolated dog BMPCs, and VPCs and MPCs expanded in vitro (P3-P4). A: BMPCs were stained with antibodies for blood lineages. B: Lineage negative c-kit-positive BMPCs were identified and sorted and analyzed in cytospin preparations; c-kit (green). C: VPCs are positive for c-kit and flk1 and negative for hematopoietic markers and $\alpha$-SA; they express at very low levels desmin, CD31, vWf and TGF-$\beta$1 receptor. D: VPCs are c-kit-positive (green) and flk1-positive (red). E: MPCs are negative for flk1 and for hematopoietic markers, CD31, vWf and TGF-$\beta$1 receptor; they express at very low levels $\alpha$-SA and desmin. F: MPCs are c-kit-positive (green) and flk1-negative.

FIG. 11. Transplanted heart. A: The heart was cut in 22 slices and 114 sections were examined. B: Large transverse section of the LV in which a cluster of EGFP-positive (green) myocytes ($\alpha$-sarcomeric actin, $\alpha$-SA: red) is located in proximity of three areas of myocardial damage (MD). More than 2000 EGFP-positive cells are present. C: Four other examples of clusters of EGFP-positive myocytes within the transplanted heart. D: Newly formed EGFP-positive coronary vessels (EGFP: green; $\alpha$-smooth muscle actin, $\alpha$-SMA: red). Inset: co-localization of EGFP and a-SMA in the vessel wall (yellow). E: Higher magnification of newly formed myocytes (left panels: EGFP, green; right panels: $\alpha$-SA: red; arrows). F: EGFP-positive cells express GATA4 (red), Nkx2.5 (red) and GATA6(red) documenting the acquisition of the myocyte and SMC lineage. G, H: Newly formed myocytes ($\alpha$-SA, red) carry the Y-chr (white dots). I: By PCR, EGFP DNA sequences were detected only in the heart (H) but not in the kidney (K), spleen (S), lung (Lu) and liver (L). J: The recognition of Sry by PCR in the heart (H) indicates the presence of male cells of recipient origin in the donor heart. K, S, Lu and L correspond to organs of the recipient dog that have therefore a male genotype (SEQ ID NOS.: 3 and 4).

FIG. 12. BMPC differentiation and cell genotyping. A: Transgene constructs in donor mice. The promoter that controls the ubiquitous or myocyte restricted expression of the transgene is shown. Also the scheme illustrates that male donor BMPCs were injected intramyocardially in wild-type female infarcted mice. NLS, nuclear localization signal; MHC, myosin heavy chain; MI, myocardial infarct. Three classes of BMPCs were employed to induce myocardial regeneration: 1. Male EGFP-positive BMPCs from $\beta$-actin-EGFP mice; 2. Male EGFP-negative BMPCs from $\alpha$-MHC-EGFP mice; and 3. Male EGFP-negative BMPCs from $\alpha$-MHC-c-myc-tagged-nuc-Akt mice. B: In case 1, all cardiac cells generated by BMPC differentiation are expected to express EGFP; in case 2, only myocytes generated by BMPC differentiation are expected to express EGFP; and in case 3, only nuclei of myocytes generated by BMPC differentiation are expected to express c-myc-tag. C: The detection of the Y-chr allowed us to discriminate resident female cardiac cells from newly formed male cardiac cells generated by BMPC differentiation.

FIG. 15. PC engraftment. Male BMPCs (Y-chr: white dots) injected in the infarcted female mouse heart express N-cadherin (A: yellow) and connexin 43 (B: yellow). Connexin 43 and N-cadherin were detected between BMPCs and between BMPCs and resident myocytes (α-SA: red) and fibroblasts (procollagen: magenta). Apoptosis of BMPCs was restricted to non-engrafted cells (C); connexin 43 was absent in TdT labeled PCs (magenta). Engrafted BMPCs are BrdU-positive (D: yellow). Mitosis is shown by phospho-H3 labeling of metaphase chromosomes (E: yellow).

FIG. 16. A: A doppler flow transducer and hydraulic occluder were implanted on the LAD. A critical stenosis was created as shown by the absence of reactive hyperemia after release (R) of 15-sec occlusion. In the absence of stenosis (B), the release leads to reactive hyperemia shown as mean and phasic CBF in the upper and lower. C: Lack of reactive hyperemia with critical stenosis 10 days after LAD constriction and the injection of EGFP-positive VPCs in six sites around the stenotic artery (A: red stars). As documented in D, 30 days after coronary constriction and cell implantation there was a slow return of CBF after release of 15-sec occlusion. These data suggest the formation of coronary vessels which restored in part CBF in the presence of a functional critical stenosis. Histologically, at 30 day, in proximity of the stenotic vessel, a large developing artery (E: diameter=~1 mm) was identified (EGFP: green; α-SMA: red; arrowheads). Preexisting vessels are EGFP negative and α-SMA positive (arrows).

DETAILED DESCRIPTION OF THE INVENTION

Figure 1:
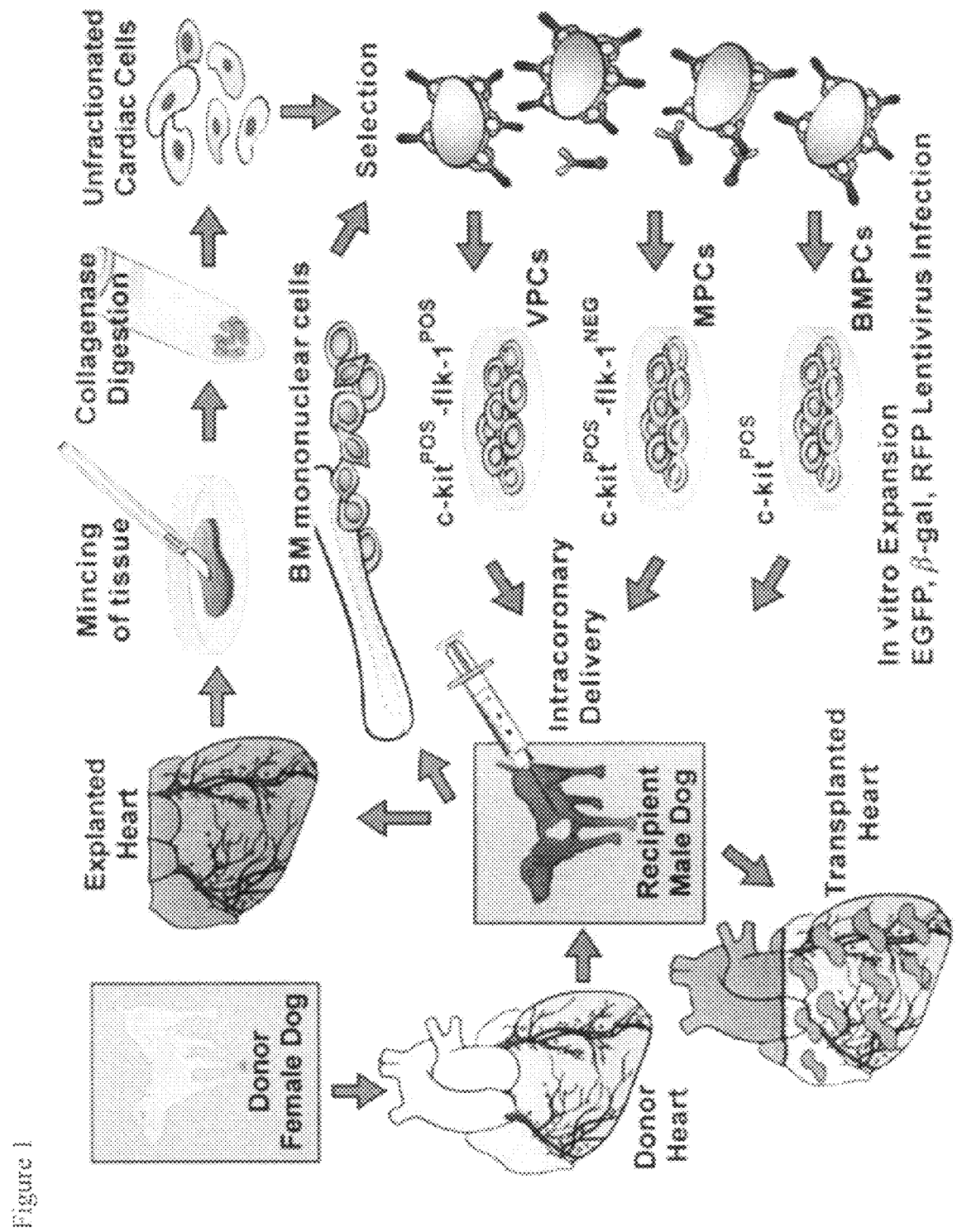
FIG. 1. Administration of progenitor cells (PCs) to the cardiac transplant. Bone marrow is harvested from the recipient male dog and mononuclear cells are lineage depleted and sorted for c-kit (BMPCs). Following transplantation of a female donor heart, the explanted heart from the recipient is dissociated and vascular progenitor cells (VPCs) and myocyte progenitor cells (MPCs) are isolated and expanded. PC classes will be infected with a lentivirus expressing EGFP, β-gal or RFP for the subsequent identification of the injected cells and their progeny at different time points. Newly formed EGFP-, β-gal and RFP-positive myocardial structures will develop within the donor myocardium. Since labeled-PCs are given repeatedly over time, the coronary route is considered the most feasible form of cell delivery.

As used herein, "autologous" refers to something that is derived or transferred from the same individual's body (i.e., autologous blood donation; an autologous bone marrow transplant).

As used herein, "allogeneic" refers to something that is genetically different although belonging to or obtained from the same species (e.g., allogeneic tissue grafts or organ transplants).

As used herein, "stem cells" are used interchangeably with "progenitor cells" and refer to cells that have the ability to renew themselves through mitosis as well as differentiate into various specialized cell types. The stem cells used in the invention are somatic stem cells, such as bone marrow or cardiac stem cells or progenitor cells. "Vascular progenitor cells" or VPCs are a subset of adult cardiac stem cells that are c-kit positive and flk1 positive, which generate predominantly endothelial cells and smooth muscle cells. "Myocyte progenitor cells" or MPCs are a subset of adult cardiac stem cells that are c-kit positive and flk1 negative, which generate cardiomyocytes predominantly.

As used herein, "adult" stem cells refers to stem cells that are not embryonic in origin nor derived from embryos or fetal tissue.

Stem cells (e.g. progenitor cells) employed in the invention are advantageously selected to be lineage negative. The term "lineage negative" is known to one skilled in the art as meaning the cell does not express antigens characteristic of specific cell lineages. For example, bone marrow progenitor cells (BMPCs) do not express any of the hematopoietic lineage markers, such as CD3, CD20, CD33, CD14, and CD15. And, it is advantageous that the lineage negative stem cells are selected to be c-kit positive. The term "c-kit" is known to one skilled in the art as being a receptor which is known to be present on the surface of stem cells, and which is routinely utilized in the process of identifying and separating stem cells from other surrounding cells.

As used herein, the term "immunocompatible" refers to the antigenic similarity of cells or tissues from a donor source to the cells or tissues in a recipient subject such that the donor cells or tissues do not induce an immune response in the recipient subject. A donor cell or tissue that does not induce an immune response in a recipient and is not rejected by the recipient subject is said to be immunocompatible.

As used herein, the term "cytokine" is used interchangeably with "growth factor" and refers to peptides or proteins that bind receptors on cell surfaces and initiate signaling cascades thus influencing cellular processes. The terms "cytokine" and "growth factor" encompass functional variants of the native cytokine or growth factor. A functional variant of the cytokine or growth factor would retain the ability to activate its corresponding receptor. Variants can include amino acid substitutions, insertions, deletions, alternative splice variants, or fragments of the native protein. The term "variant" with respect to a polypeptide refers to an amino acid sequence that is altered by one or more amino acids with respect to a reference sequence. The variant can have "conservative" changes, wherein a substituted amino acid has similar structural or chemical properties, e.g., replacement of leucine with isoleucine. Alternatively, a variant can have "nonconservative" changes, e.g., replacement of a glycine with a tryptophan. Analogous minor variations can also include amino acid deletion or insertion, or both. Guidance in determining which amino acid residues can be substituted, inserted, or deleted without eliminating biological activity can be found using computer programs well known in the art, for example, DNASTAR software.

As used herein, "patient" or "subject" may encompass any vertebrate including but not limited to humans, mammals, reptiles, amphibians and fish. However, advantageously, the patient or subject is a mammal such as a human, or a mammal such as a domesticated mammal, e.g., dog, cat, horse, and the like, or production mammal, e.g., cow, sheep, pig, and the like.

The pharmaceutical compositions of the present invention may be used as therapeutic agents—i.e. in therapy applications. As herein, the terms "treatment" and "therapy" include curative effects, alleviation effects, and prophylactic effects. In certain embodiments, a therapeutically effective dose of progenitor cells is applied, delivered, or administered to the heart or implanted into the heart. An effective dose or amount is an amount sufficient to effect a beneficial or desired clinical result. Said dose could be administered in one or more administrations.

Mention is made of the following related pending patent applications:

U.S. Application Publication No. 2003/0054973, filed Jun. 5, 2002, which is herein incorporated by reference in its entirety, discloses methods, compositions, and kits for repairing damaged myocardium and/or myocardial cells including the administration of cytokines.

U.S. Application Publication No. 2006/0239983, filed Feb. 16, 2006, which is herein incorporated by reference in its entirety, discloses methods, compositions, and kits for repairing damaged myocardium and/or myocardial cells including the administration of cytokines and/or adult stem cells as well as methods and compositions for the development of large arteries and vessels. The application also discloses methods and media for the growth, expansion, and activation of human cardiac stem cells.

Successful transplantation has an inherent yearly 6% mortality and most patients die within 10-12 years. The improved immunosuppressive regimen has resulted in increased short-term survival but long-term survival has remained largely the same. Post-operative morbidity and mortality associated with cardiac transplantation is dictated by acute and chronic complications which rapidly affect the performance of the new heart or lead with time to a progressive deterioration of cardiac function. Chronic rejection with accelerated cardiac allograft vasculopathy (CAV) is the major pathological event that determines the fatal evolution of the transplanted heart. Graft failure due to CAV is characterized by occlusive vessel disease that results in myocardial infarction, multiple focal areas of tissue injury, arrhythmias, sudden death and congestive heart failure. Infarct healing with scar formation is impaired by immunosuppressive therapy which further complicates the devastating consequences of graft atherosclerosis and arteriosclerosis. The mechanisms of graft atherosclerosis and arteriosclerosis are not understood but repetitive cell-mediated and/or humoral-mediated immunological damage followed by a potentiated myointimal response are involved in the manifestations of this unique form of coronary artery disease. Thus, three interrelated pathologic processes appear to be critical determinants of heart failure in the transplanted heart: rejection, evolving coronary atherosclerosis and chronic ischemic myocardial injury.

Chronic rejection with accelerated graft atherosclerosis is the major pathological event that determines the fatal evolution of the transplanted heart. Occlusive vessel disease of the large, intermediate and small coronary arteries results in multiple focal areas of injury, myocardial infarction and ischemic heart failure. The novel methods of the invention provide a solution to the major problems associated with the unfavorable progression of cardiac transplantation in humans by employing progenitor cells from the recipient to repopulate the donor heart with immunocompatible cardiomyocytes and coronary vessels.

Functionally competent cardiac progenitor cells also known as cardiac stem cells are present in the explanted heart of patients undergoing cardiac transplantation and these can be isolated and grown in vitro for subsequent autologous cell therapy. Additionally, in the acute phase, bone marrow progenitor cells (BMPCs) from the recipient can be utilized in view of their ability to transdifferentiate and acquire the cardiomyocyte fate and form vascular structures.

Thus, the donor heart can provide the scaffolding for the generation of a new heart derived from implantation, engraftment and differentiation of BMPCs and cardiac progenitor cells isolated from the recipient. Two distinct classes of cardiac progenitor cells exist within the heart: vascular progenitor cells (VPCs) and myocyte progenitor cells (MPCs). VPCs are programmed to differentiate predominantly into vascular smooth muscle cells (SMCs) and endothelial cells (ECs), but also have the ability to acquire the cardiomyocyte lineage. On the other hand, MPCs predominantly generate cardiomyocytes and to a more limited extent SMCs and ECs.

Successful engraftment of progenitor cells is the initial process of tissue repair. Myocardial reconstitution necessitates the generation of a cardiomyocyte compartment together with a proportional coronary vasculature. Myocytes alone in the absence of adequate blood supply cannot perform their function, and coronary vessels alone without muscle mass cannot restore cardiac performance (36, 184, 185). Engrafted progenitor cells may result in a coordinated growth response in which myocytes and vessels are concurrently formed to engender functionally competent myocardium. Coronary blood flow is regulated by conductive coronary arteries and resistance coronary arterioles (186) while oxygen availability and diffusion are controlled by the capillary network (136, 188).

BMPCs, VPCs, and MPCs isolated from the recipient can be delivered to the donor heart to promote the formation of immunocompatible myocardium within the non-immunocompatible transplanted heart. The reconstituted myocardium will be comprised of immunocompatible coronary vessels and coronary myocytes which can replace and/or repair the non-immunocompatible diseased arteries and myocardium. Thus, immunosuppressive therapy may no longer be required resulting in significant improvement of quality of life and lifespan of patients after cardiac transplantation.

The present invention provides methods of reducing transplant rejection in a subject by isolating cardiac or bone marrow progenitor cells from tissue specimens from the recipient, expanding and optionally activating the progenitor cells in culture, and subsequently administering the recipient's progenitor cells to the transplanted donor heart. The implanted progenitor cells then generate immunocompatible endothelial cells, smooth muscle cells, and cardiomyocytes within the non-immunocompatible donor myocardium, which assemble into immunocompatible myocardium and myocardial vessels, thus reducing the immune response to the donor organ.

In one embodiment, the present invention provides a method of reducing an immune response to a transplanted donor heart in a subject comprising obtaining myocardial tissue from the subject's explanted heart; extracting cardiac progenitor cells from said myocardial tissue; expanding said cardiac progenitor cells in culture; and administering said cardiac progenitor cells to the transplanted donor heart, wherein said cardiac progenitor cells generate immunocompatible myocardium and immunocompatible myocardial vessels following their administration, thereby reducing the immune response to said transplanted donor heart. In some embodiments, the subject is human.

Figure 5:
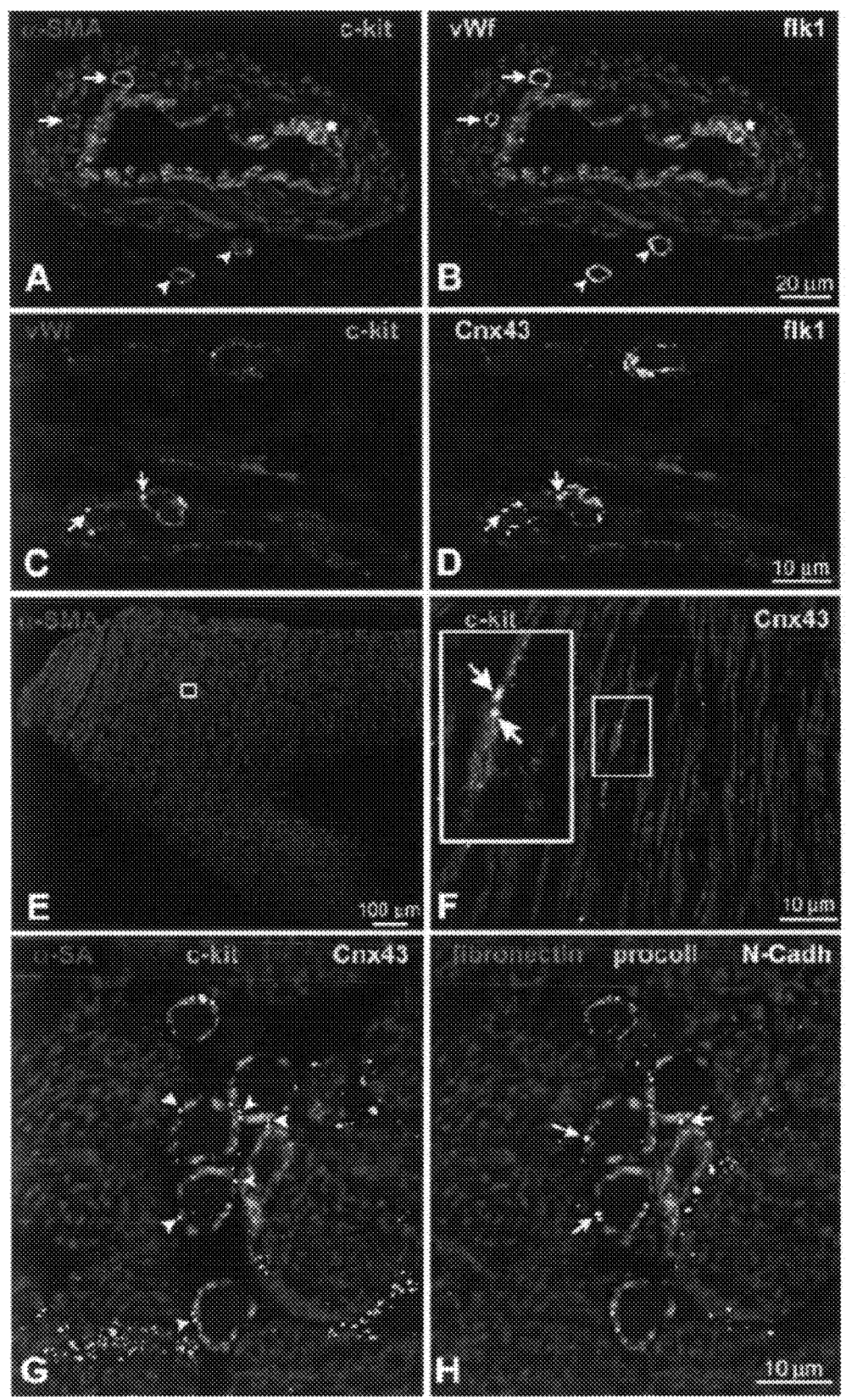
FIG. 5. Dog heart: vascular and myocardial niches. A: Resistance coronary arteriole; c-kit-positive cells (green) are present in the intima (vWf, yellow, *), SMC layer ($\alpha$-SMA, red, arrows) and adventitia (not stained, arrowheads). B: The c-kit-positive-cells express flk1 (white), i.e., VPC niche. C, D: Tangential section of myocardial capillaries that exhibit 3 c-kit-positive flk1-positive VPCs. Connexin 43 (yellow, arrows) is present between VPCs and ECs. E: Large section of a dog coronary artery (SMCs, $\alpha$-SMA; red). Area in the rectangle is shown in panel F: 2 VPCs are connected to SMCs. The inset illustrates connexin 43 (yellow, arrows). (G, H: LV myocardium which shows a cluster of c-kit-positive flk1-negative cells (green), i.e., MPC niche. Connexin 43 (arrowheads) and N-cadherin (arrows) are present between two MPCs, and between MPCs and myocytes ($\alpha$-SA, red) or MPCs and fibroblasts (procollagen, light blue).

It is preferable that the cardiac progenitor cells be c-kit positive. The c-kit stem cell marker is associated with progenitor cells with apparent comparable functional behavior for cardiac repair whether they derive from the heart or the bone marrow (47, 48, 51, 57, 59, 64, 139, 140). In some embodiments, the cardiac progenitor cells are separated into vascular progenitor cells and myocyte progenitor cells prior to administration. Recently, the inventors have discovered that the adult heart in mice, dogs and humans contains two populations of progenitor cells (PCs); a vascular progenitor cell (VPC), which is stored in niches located within the wall of coronary vessels, and a myocyte progenitor cell (MPC), which is located in myocardial niches, distinct from vascular niches (FIG. 5). See also U.S. Provisional Application No. 60/991,515, which is herein incorporated by reference in its entirety. VPCs are primitive cells which are self-renewing, clonogenic and multipotent in vitro and can regenerate coronary vessels in vivo. Although coronary VPCs are programmed to differentiate predominantly into smooth muscle cells (SMCs) and endothelial cells (ECs), they also possess the inherent ability to acquire modestly the cardiomyocyte lineage. Conversely, MPCs generate predominantly cardiomyocytes and to a limited extent vascular SMCs and ECs.

The c-kit marker is present in the absence of flk1 in MPCs (29, 64, 138-140) and together with flk1 in VPCs (FIG. 5). Therefore, the pool of lineage negative c-kit-positive PCs in the heart may be separated into two cell categories according to the expression of the vascular endothelial growth factor receptor 2 (VEGF-R2/flk1). The expression of VEGFR2 or kinase domain receptor (KDR/flk1), which represents the earliest marker of angioblast precursors (141-145), is a good predictor of VPCs. Flk1 is an epicardium-specific marker and epicardial-derived cells initiate vasculogenesis in the prenatal heart (146, 147). In the mouse embryo, flk1 is necessary for the development of the coronary vasculature (148, 149). Recent results have suggested that the growth potential of flk1-positive PCs exceeds hematopoiesis and vasculogenesis (144, 145, 150-156). The endocardium and a small population of cells in the myocardium originate from a pool of flk1-positive cells (153-156). Additionally, multipotent flk1 PCs form colonies of ECs, SMCs and myocytes (145). Thus, the expression of flk1 and c-kit may be utilized to distinguish VPCs and MPCs. In one embodiment, the vascular progenitor cells are c-kit positive and flk1 positive. In another embodiment, the vascular progenitor cells differentiate into immunocompatible endothelial cells and smooth muscle cells. In another embodiment, the myocyte progenitor cells are c-kit positive and flk1 negative. In still another embodiment, the myocyte progenitor cells differentiate into immunocompatible cardiomyocytes.

In another embodiment, the present invention provides a method of reducing an immune response to a transplanted donor heart in a subject comprising obtaining myocardial tissue from the subject's explanted heart; extracting cardiac myocyte progenitor cells from said myocardial tissue; expanding said myocyte progenitor cells in culture; and administering said myocyte progenitor cells to the transplanted donor heart, wherein said myocyte progenitor cells generate immunocompatible myocardium following their administration, thereby reducing the immune response to said transplanted donor heart. In some embodiments, the myocyte progenitor cells are c-kit positive and flk1 negative. In other embodiments the myocyte progenitor cells differentiate into immunocompatible cardiomyocytes.

Adult bone marrow progenitor cells (BMPCs) are capable of generating mature cells beyond their own tissue boundaries, a process which has been termed developmental plasticity. Based on this premise, the inventors have documented that BMPCs regenerate infarcted myocardium in rodents leading to the formation of cardiomyocytes and coronary vessels which are structurally and functionally connected to resident cardiomyocytes and the primary coronary circulation. Thus, BMPCs can also be employed to generate immunocompatible myocardium to prevent rejection of a transplanted heart. Because BMPCs can be obtained from the recipient subject prior to the transplant surgery, the BMPCs can be expanded in culture and ready for administration to the donor heart at the time of the transplant surgery. Therefore, in another embodiment of the invention, the method of reducing an immune response to a transplanted donor heart in a subject comprises obtaining a bone marrow specimen from the subject; extracting adult bone marrow progenitor cells from said specimen; expanding said bone marrow progenitor cells in culture; and administering said bone marrow progenitor cells to the transplanted donor heart, wherein said bone marrow progenitor cells generate immunocompatible myocardium and immunocompatible myocardial vessels following their administration, thereby reducing the immune response to said transplanted donor heart. In some embodiments, the bone marrow progenitor cells are administered immediately after transplantation.

The stem cell antigen c-kit is expressed in a population of BMPCs that are capable of differentiating into cardiomyocytes and SMCs and ECs organized in coronary vessels (47, 48, 51). Therefore, the presence of c-kit may be employed to isolate BMPCs. Accordingly, in one embodiment of the invention, the bone marrow progenitor cells are c-kit positive. In another embodiment, the bone marrow progenitor cells differentiate into immunocompatible endothelial cells, smooth muscle cells, and cardiomyocytes.

In another embodiment, vascular progenitor cells and/or myocyte progenitor cells may be administered to the donor heart following administration of bone marrow progenitor cells. For instance, in some embodiments, the method further comprises extracting cardiac progenitor cells from said subject's explanted heart; separating said cardiac progenitor cells into vascular progenitor cells and myoctye progenitor cells; and administering said vascular progenitor cells and myoctye progenitor cells to the transplanted donor heart. In such embodiments, the BMPCs administered at the time of transplant surgery initiate the generation of immunocompatible myocardial tissue and vessels, and this generation is expanded by the subsequent administration of VPCs and MPCs. The VPCs and MPCs may be administered multiple times after transplantation and the multiple administrations may occur at a set interval after the administration of the BMPCs. For example, VPCs and/or MPCs may be administered to the donor heart every week, two weeks, three weeks, month, two months, three months, six months, nine months, year, two years, three years, or five years after BMPC administration.

The present invention also provides a method of reducing cardiac allograft vasculopathy in a subject who has received a transplanted donor heart. Cardiac allograft vasculopathy is an accelerated form of coronary artery disease that affects the vasculature of the allograft and is the primary cause of death in transplant patients surviving one year after transplantation. The non-immunocompatible tissue of the allograft induces an immune response in the recipient subject that leads to endothelial cell damage and vascular injury. The vascular injury initiates a repair response that can lead to the occlusion of the vessel and subsequent infarction.

Use of cardiac progenitor cells isolated from the recipient may be used to generate immunocompatible myocardial tissue in the donor heart to reduce an immune response, and thus also reduce the development of cardiac allograft vasculopathy. In addition, vascular progenitor cells obtained from the recipient subject can be employed to generate immunocompatible vessels in the donor heart that would not be susceptible to immune-mediated injury. Thus, in one embodiment of the invention, the method of reducing cardiac allograft vasculopathy in a subject comprises obtaining myocardial tissue from the subject's explanted heart; extracting cardiac vascular progenitor cells from said myocardial tissue; expanding said vascular progenitor cells in culture; and administering said vascular progenitor cells to the transplanted donor heart, wherein said vascular progenitor cells generate immunocompatible coronary vasculature, thereby repairing/and or regenerating the non-immunocompatible coronary arteries of the donor heart. In some embodiments, the vascular progenitor cells are c-kit positive and flk1 positive. In other embodiments, the vascular progenitor cells differentiate into immunocompatible endothelial cells and smooth muscle cells.

Progenitor cells may be isolated from tissue specimens, such as myocardium or bone marrow, obtained from a subject or patient, such as the transplant recipient. By way of example, myocardial tissue specimens obtained from the recipient's explanted heart may be minced and placed in appropriate culture medium. Cardiac progenitor cells growing out from the tissue specimens can be observed in approximately 1-2 weeks after initial culture. At approximately 4 weeks after the initial culture, the expanded progenitor cells may be collected by centrifugation. An exemplary method for obtaining bone marrow progenitor cells from a subject is described as follows. Bone marrow may be harvested from the iliac crests using a needle and the red blood cells in the sample may be lysed using standard reagents. Bone marrow progenitor cells are collected from the sample by density gradient centrifugation. Optionally, the bone marrow progenitor cells may be expanded in culture. Other methods of isolating adult progenitor cells, such as bone marrow progenitor cells and cardiac progenitor cells, from a subject are known in the art and can be employed to obtain suitable progenitor cells for use in the methods of the invention. U.S. Patent Application Publication No. 2006/0239983, filed Feb. 16, 2006, which is herein incorporated by reference in its entirety, describes media appropriate for culturing and expanding adult progenitor cells. However, one of ordinary skill in the art would be able to determine the necessary components and modify commonly used cell culture media to be employed in culturing the isolated progenitor cells of the invention.

It is preferable that the progenitor cells of the invention are lineage negative. Lineage negative progenitor cells can be isolated by various means, including but not limited to, removing lineage positive cells by contacting the progenitor cell population with antibodies against lineage markers and subsequently isolating the antibody-bound cells by using an anti-immunoglobulin antibody conjugated to magnetic beads and a biomagnet. Alternatively, the antibody-bound lineage positive stem cells may be retained on a column containing beads conjugated to anti-immunoglobulin antibodies. For instance, lineage negative bone marrow progenitor cells may be obtained by incubating mononuclear cells isolated from a bone marrow specimen with immunomagnetic beads conjugated with monoclonal antibodies for CD3 (T lymphocytes), CD20 (B lymphocytes), CD33 (myeloid progenitors), CD14 and CD15 (monocytes). The cells not bound to the immunomagnetic beads represent the lineage negative bone marrow progenitor cell fraction and may be isolated. Similarly, cells expressing markers of the cardiac lineage may be removed from cardiac progenitor cell populations to isolate lineage negative cardiac progenitor cells.

In a preferred embodiment of the invention, the lineage negative progenitor cells express the stem cell surface marker, c-kit, which is the receptor for stem cell factor. Positive selection methods for isolating a population of lineage negative progenitor cells expressing c-kit are well known to the skilled artisan. Examples of possible methods include, but are not limited to, various types of cell sorting, such as fluorescence activated cell sorting (FACS) and magnetic cell sorting as well as modified forms of affinity chromatography. In a preferred embodiment, the lineage negative progenitor cells are c-kit positive. In some embodiments, c-kit positive cardiac progenitor cells are further separated into subpopulations of cells expressing the VEGFR2 receptor, flk1. Cardiac progenitor cells that are c-kit positive and flk1 positive are vascular progenitor cells, while cardiac progenitor cells that are c-kit positive and flk1 negative are myocyte progenitor cells. Similar positive selection methods for isolating c-kit positive progenitor cells may be used to select cells expressing the flk1 receptor (e.g. immunobeads, cell sorting, affinity chromatography, etc.).

Isolated lineage negative, c-kit positive progenitor cells may be plated individually in single wells of a cell culture plate and expanded to obtain clones from individual progenitor cells. In some embodiments, cardiac progenitor cells that are c-kit positive and flk1 positive are plated individually to obtain pure cultures of vascular progenitor cells. In other embodiments, cardiac progenitor cells that are c-kit positive and flk1 negative are plated individually to obtain pure cultures of myocyte progenitor cells.

In certain embodiments of the invention, the cardiac progenitor cells or bone marrow progenitor cells are activated prior to administration. Activation of the progenitor cells may be accomplished by exposing the progenitor cells to one or more cytokines. Suitable concentrations of the one or more cytokines for activating the progenitor cells include a concentration of about 0.1 to about 500 ng/ml, about 10 to about 500 ng/ml, about 20 to about 400 ng/ml, about 30 to about 300 ng/ml, about 50 to about 200 ng/ml, or about 80 to about 150 ng/ml. In one embodiment, the concentration of one or more cytokines is about 25, about 50, about 75, about 100, about 125, about 150, about 175, about 200, about 225, about 250, about 275, about 300, about 325, about 350, about 375, about 400, about 425, about 450, about 475, or about 500 ng/ml. In some embodiments, the cardiac progenitor cells or bone marrow progenitor cells are activated by contact with hepatocyte growth factor (HGF), insulin-like growth factor-1 (IGF-1), or variant thereof.

HGF positively influences stem cell migration and homing through the activation of the c-Met receptor (Kollet et al. (2003) J. Clin. Invest. 112: 160-169; Linke et al. (2005) Proc. Natl. Acad. Sci. USA 102: 8966-8971; Rosu-Myles et al. (2005) J. Cell. Sci. 118: 4343-4352; Urbanek et al. (2005) Circ. Res. 97: 663-673). Similarly, IGF-1 and its corresponding receptor (IGF-1R) induce cardiac stem cell division, upregulate telomerase activity, hinder replicative senescence and preserve the pool of functionally-competent cardiac stem cells in the heart (Kajstura et al. (2001) Diabetes 50: 1414-1424; Torella et al. (2004) Circ. Res. 94: 514-524; Davis et al. (2006) Proc. Natl. Acad. Sci. USA 103: 8155-8160). In some embodiments, the cardiac progenitor cells or bone marrow progenitor cells are contacted with HGF and IGF-1.

Some other non-limiting examples of cytokines that are suitable for the activation of the cardiac progenitor cells or bone marrow progenitor cells include Activin A, Bone Morphogenic Protein 2, Bone Morphogenic Protein 4, Bone Morphogenic Protein 6, Cardiotrophin-1, Fibroblast Growth Factor 1, Fibroblast Growth Factor 4, Flt3 Ligand, Glial-Derived Neurotrophic Factor, Heparin, Insulin-like Growth Factor-II, Insulin-Like Growth Factor Binding Protein-3, Insulin-Like Growth Factor Binding Protein-5, Interleukin-3, Interleukin-6, Interleukin-8, Leukemia Inhibitory Factor, Midkine, Platelet-Derived Growth Factor AA, Platelet-Derived Growth Factor BB, Progesterone, Putrescine, Stem Cell Factor, Stromal-Derived Factor-1, Thrombopoietin, Transforming Growth Factor-α, Transforming Growth Factor-β1, Transforming Growth Factor-β2, Transforming Growth Factor-β3, Vascular Endothelial Growth Factor, Wnt1, Wnt3a, and Wnt5a, as described in Kanemura et al. (2005) Cell Transplant. 14:673-682; Kaplan et al. (2005) Nature 438:750-751; Xu et al. (2005) Methods Mol. Med. 121:189-202; Quinn et al. (2005) Methods Mol. Med. 121:125-148; Almeida et al. (2005) J Biol Chem. 280:41342-41351; Barnabe-Heider et al. (2005) Neuron 48:253-265; Madlambayan et al. (2005) Exp Hematol 33:1229-1239; Kamanga-Sollo et al. (2005) Exp Cell Res 311:167-176; Heese et al. (2005) Neuro-oncol. 7:476-484; He et al. (2005) Am J Physiol. 289:H968-H972; Beattie et al. (2005) Stem Cells 23:489-495; Sekiya et al. (2005) Cell Tissue Res 320:269-276; Weidt (2004) Stem Cells 22:890-896; Encabo et al (2004) Stem Cells 22:725-740; and Buytaeri-Hoefen et al. (2004) Stem Cells 22:669-674, the entire text of each of which is incorporated herein by reference.

Functional variants of the above-mentioned cytokines can also be employed in the invention. Functional cytokine variants would retain the ability to bind and activate their corresponding receptors. Variants can include amino acid substitutions, insertions, deletions, alternative splice variants, or fragments of the native protein. For example, NK1 and NK2 are natural splice variants of HGF, which are able to bind to the c-MET receptor. These types of naturally occurring splice variants as well as engineered variants of the cytokine proteins that retain function can be employed to activate the progenitor cells of the invention.

The present invention involves administering a therapeutically effective dose or amount of progenitor cells to a donor heart. An effective dose is an amount sufficient to effect a beneficial or desired clinical result. Said dose could be administered in one or more administrations. In some embodiments, at least three effective doses are administered to the donor heart in the recipient subject. In other embodiments, at least five effective doses are administered to the donor heart in the recipient subject. Each administration of progenitor cells may comprise a single type of progenitor cell (e.g. BMPC, VPC, or MPC) or may contain mixtures of the different types of progenitor cells. In one embodiment, bone marrow progenitor cells (BMPCs) are administered to the subject at the time of transplantation, and vascular progenitor cells (VPCs) and/or myocyte progenitor cells (MPCs) are administered at set intervals after transplantation. Examples of suitable intervals include, but are not limited to, 1 week, 2 weeks, 3 weeks, 1 month, 2 months, 3 months, 6 months, 12 months, 18 months or 24 months.

An effective dose of progenitor cells may be from about $2 \times 10^4$ to about $1 \times 10^7$, more preferably about $1 \times 10^5$ to about $6 \times 10^6$, or most preferably about $2 \times 10^6$. As illustrated in the examples, $2 \times 10^6$ to $1 \times 10^7$ progenitor cells are used to effect regeneration of immunocompatible myocardium in a canine model. Although there would be a size difference between the heart of a canine and the heart of a human, it is likely that this range of progenitor cells would be sufficient in a human as well. However, the precise determination of what would be considered an effective dose may be based on factors individual to each patient, including their size, age, size of donor heart, type of repopulating progenitor cells (e.g. VPCs, MPCs, or BMPCs), and amount of time after transplantation. One skilled in the art, specifically a physician or cardiologist, would be able to determine the number of progenitor cells that would constitute an effective dose without undue experimentation.

The progenitor cells (e.g. stem cells) may be administered to the heart by injection. The injection is preferably intramyocardial. As one skilled in the art would be aware, this is the preferred method of delivery for stem cells as the heart is a functioning muscle. Injection by this route ensures that the injected material will not be lost due to the contracting movements of the heart.

In another embodiment, the progenitor cells are administered by injection transendocardially or trans-epicardially. In another embodiment of the invention, the progenitor cells are administered using a catheter-based approach to deliver the trans-endocardial injection. The use of a catheter precludes more invasive methods of delivery wherein the opening of the chest cavity would be necessitated. As one skilled in the art would appreciate, optimum time of recovery would be allowed by the more minimally invasive procedure. A catheter approach involves the use of such techniques as the NOGA catheter or similar systems. The NOGA catheter system facilitates guided administration by providing electromechanic mapping of the area of interest, as well as a retractable needle that can be used to deliver targeted injections or to bathe a targeted area with a therapeutic. Any of the embodiments of the present invention can be administered through the use of such a system to deliver injections or provide a therapeutic. One of skill in the art will recognize alternate systems that also provide the ability to provide targeted treatment through the integration of imaging and a catheter delivery system that can be used with the present invention. Information regarding the use of NOGA and similar systems can be found in, for example, Sherman (2003) Basic Appl. Myol. 13: 11-14; Patel et al. (2005) The Journal of Thoracic and Cardiovascular Surgery 130:1631-38; and Perrin et al. (2003) Circulation 107: 2294-2302; the text of each of which are incorporated herein in their entirety.

In still another embodiment, the progenitor cells may be administered to a donor heart by an intracoronary route. This route obviates the need to open the chest cavity to deliver the cells directly to the heart. One of skill in the art will recognize other useful methods of delivery or implantation which can be utilized with the present invention, including those described in Dawn et al. (2005) Proc. Natl. Acad. Sci. USA 102, 3766-3771, the contents of which are incorporated herein in their entirety.

In some embodiments, the methods of the invention described herein further comprise administering to the subject an immunosuppressive therapy or immunosuppressant. Non-limiting examples of immunosuppressants include cyclosporine A, azathioprine, glucocorticoids (e.g. methylprednisolone, cortisol, prednisone, dexamethasone, betamethasone), cyclophosphamide, methotrexate, mercaptopurine, dactinomycin, anthracyclines, mitomycin C, bleomycin, mithramycin, tacrolimus, sirolimus, everolimus, myriocin, and antibodies (e.g. basiliximab, daclizumab, anti-thymocyte globulin, anti-lymphocyte globulin). Other therapeutic agents that are typically given to transplant patients, for instance HMG-CoA reductase inhibitors, rapamycin, and paclitaxel, may also be used in combination with the administration of progenitor cells. The immunosuppressants or other therapeutic agents may be administered to the subject in multiple doses subsequent to the administration of the progenitor cells. The immunosuppressants or other therapeutic agents may be taken on a routine schedule for a set period of time. For example, the immunosuppressants or other therapeutic agents may be taken once daily for about 1 month, about 2 months, about 3 months, about 6 months, about 12 months, or about 24 months after transplantation and administration of the progenitor cells. Other dosing schedules may be employed. Preferably, the dose and/or frequency of immunosuppressants or other therapeutic agents will be reduced following one or more administrations of the progenitor cells to the donor heart. One of skill in the art, particularly a physician or cardiologist, would be able to determine the appropriate dose and schedule for the administration of the immunosuppressants or other therapeutic agents.

The invention also comprehends methods for preparing compositions, such as pharmaceutical compositions, including one or more of the different type of progenitor cells described herein, for instance, for use in inventive methods for reducing cardiac allograft vasculopathy or transplant rejection. In one embodiment, the pharmaceutical composition comprises bone marrow progenitor cells and a pharmaceutically acceptable carrier, wherein said bone marrow progenitor cells are c-kit positive. In another embodiment, the pharmaceutical composition comprises vascular progenitor cells and a pharmaceutically acceptable carrier, wherein said vascular progenitor cells are c-kit positive and flk1 positive. In another embodiment, the pharmaceutical composition comprises myocyte progenitor cells and a pharmaceutically acceptable carrier, wherein said myocyte progenitor cells are c-kit positive and flk1 negative. In still another embodiment, the pharmaceutical composition comprises vascular progenitor cells, myocyte progenitor cells and a pharmaceutically acceptable carrier, wherein said vascular progenitor cells are c-kit positive and flk1 positive and said myocyte progenitor cells are c-kit positive and flk1 negative.

In an additionally preferred aspect, the pharmaceutical compositions of the present invention are delivered via injection. These routes for administration (delivery) include, but are not limited to, subcutaneous or parenteral including intravenous, intraarterial (e.g. intracoronary), intramuscular, intraperitoneal, intramyocardial, transendocardial, trans-epicardial, intranasal administration as well as intrathecal, and infusion techniques. Accordingly, the pharmaceutical composition is preferably in a form that is suitable for injection.

When administering a therapeutic of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion, and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions.

Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the progenitor cells and other compounds used in combination with the progenitor cells.

Sterile injectable solutions can be prepared by incorporating the compounds utilized in practicing the present invention in the required amount of the appropriate solvent with various amounts of the other ingredients, as desired.

The pharmaceutical compositions of the present invention, e.g., comprising a therapeutic dose of progenitor cells (e.g. BMPCs, VPC, and MPCs), can be administered to the patient in an injectable formulation containing any compatible carrier, such as various vehicles, adjuvants, additives, and diluents. Compounds, such as immunosuppressants or other therapeutic agents, to be administered as a combination therapy with the progenitor cells can be administered parenterally to the patient in the form of slow-release subcutaneous implants or targeted delivery systems such as monoclonal antibodies, iontophoretic, polymer matrices, liposomes, and microspheres.

Examples of compositions comprising a therapeutic of the invention include liquid preparations for parenteral, subcutaneous, intradermal, intramuscular, intracoronarial, intramyocardial or intravenous administration (e.g., injectable administration), such as sterile suspensions or emulsions. Such compositions may be in admixture with a suitable carrier, diluent, or excipient such as sterile water, physiological saline, glucose or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

The compositions can be isotonic, i.e., they can have the same osmotic pressure as blood and lacrimal fluid. The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions may be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount which will achieve the selected viscosity. Viscous compositions are normally prepared from solutions by the addition of such thickening agents.

A pharmaceutically acceptable preservative can be employed to increase the shelf-life of the compositions. Benzyl alcohol may be suitable, although a variety of preservatives including, for example, parabens, thimerosal, chlorobutanol, or benzalkonium chloride may also be employed. A suitable concentration of the preservative will be from 0.02% to 2% based on the total weight although there may be appreciable variation depending upon the agent selected.

Those skilled in the art will recognize that the components of the compositions should be selected to be chemically inert with respect to the active compound. This will present no problem to those skilled in chemical and pharmaceutical principles, or problems can be readily avoided by reference to standard texts or by simple experiments (not involving undue experimentation), from this disclosure and the documents cited herein.

The inventive compositions of this invention are prepared by mixing the ingredients following generally accepted procedures. For example, isolated progenitor cells can be resuspended in an appropriate pharmaceutically acceptable carrier and the mixture adjusted to the final concentration and viscosity by the addition of water or thickening agent and possibly a buffer to control pH or an additional solute to control tonicity. Generally the pH may be from about 3 to 7.5. Compositions can be administered in dosages and by techniques well known to those skilled in the medical and veterinary arts taking into consideration such factors as the age, sex, weight, and condition of the particular patient, and the composition form used for administration (e.g., liquid). Dosages for humans or other mammals can be determined without undue experimentation by the skilled artisan, from this disclosure, the documents cited herein, and the knowledge in the art.

Suitable regimes for initial administration and further doses or for sequential administrations also are variable, may include an initial administration followed by subsequent administrations; but nonetheless, may be ascertained by the skilled artisan, from this disclosure, the documents cited herein, and the knowledge in the art.

This invention is further illustrated by the following additional examples that should not be construed as limiting. The contents of all references, patents and published patent applications cited throughout this application, as well as the Figures, are incorporated herein by reference in their entirety.

EXAMPLES

Example 1

Cardiac Transplantation in Dogs

In all examples described herein, female dog hearts are transplanted in male dogs and the cells to be injected (bone marrow progenitor cells (BMPCs), vascular progenitor cells (VPCs) or myocyte progenitor cells (MPCs)) are infected with a lentivirus expressing enhanced green fluorescent protein (EGFP), β-gal or red fluorescent protein (RFP) so that the progeny formed by cells given at different time points can be identified and measured.

Figure 7:
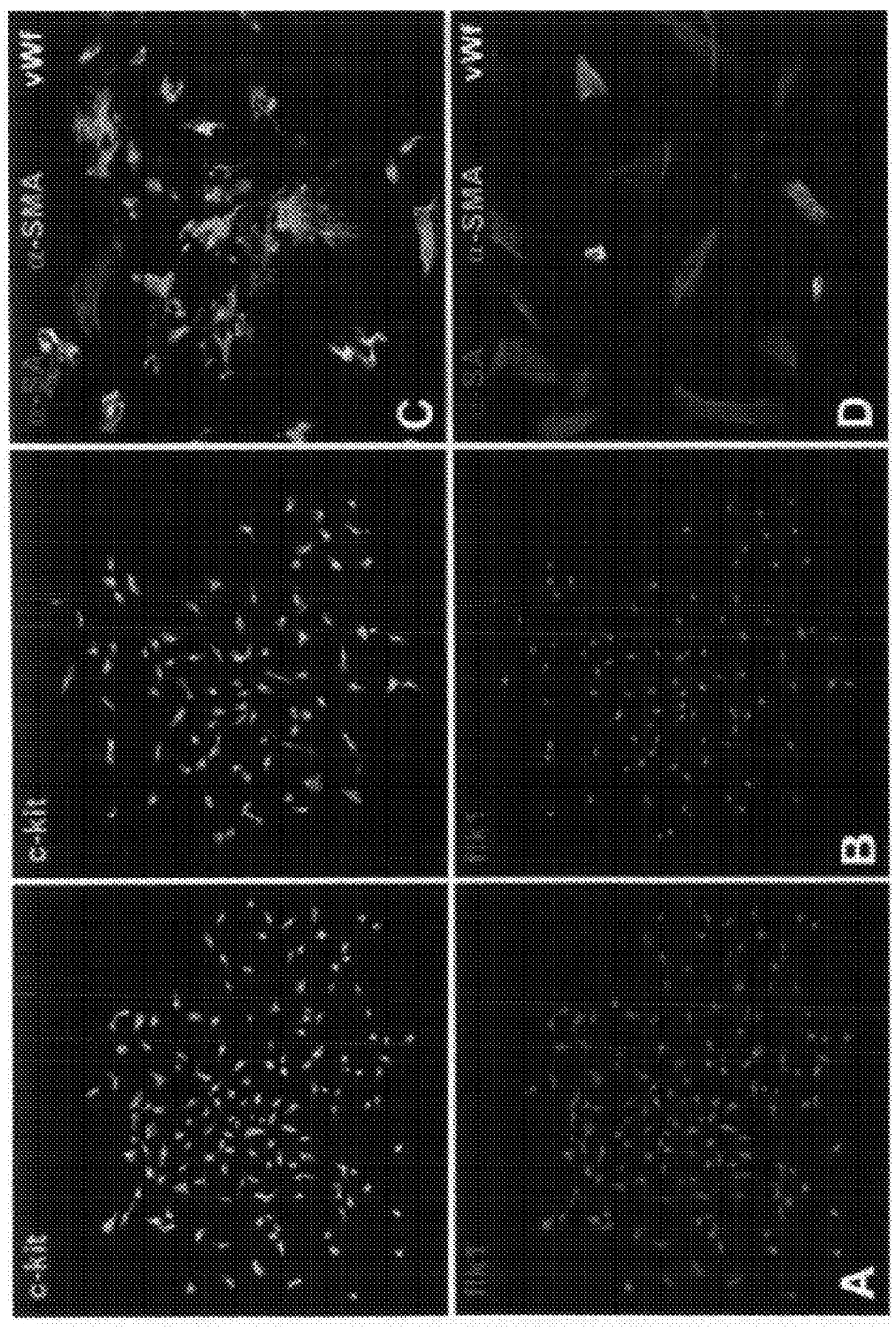
FIG. 7. Clones and derived progeny. Single VPCs isolated from dog coronary arteries (A) and MPCs from the myocardium (B) formed multicellular clones. VPCs are c-kit (green) and flk1 (red) positive. MPCs are c-kit (green) positive and flk1-negative. C: Clonogenic VPCs differentiate into SMCs ($\alpha$-SMA, green), 59±4%, ECs (vWf, yellow), 31±4%, and myocytes ($\alpha$-SA, red), 10±2%. D: Clonogenic MPCs differentiate into SMCs, 16±6%, ECs, 11±5%, and myocytes, 73±9%.
Figure 8:
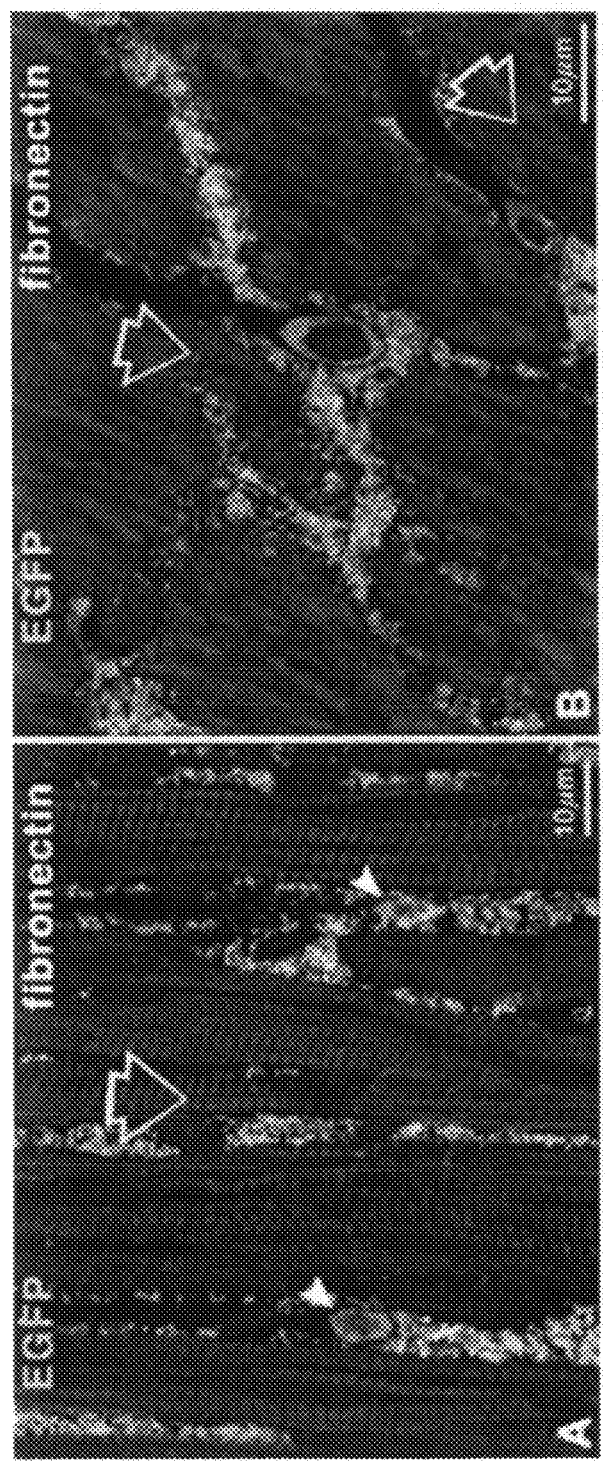
FIG. 8. Translocation of PCs. Migrating EGFP-MPCs (A & B) are located within interstitial fibronectin tunnels (yellow). Arrows point to the direction of migration of the EGFP-MPCs established in living tissue by two-photon microscopy.

In the last two years, a tremendous effort was made to develop a model of cardiac transplantation in the dog. The dog model was chosen after careful review because the dog is the smallest animal that fits the experimental requirements. Immunosuppression is well described in dogs (198-200) and canine MPCs and VPCs (64; FIGS. 5-7) have been isolated, expanded and characterized in vitro and in vivo. Thus, the use of the dog model maximizes efficiency.

Figure 4:
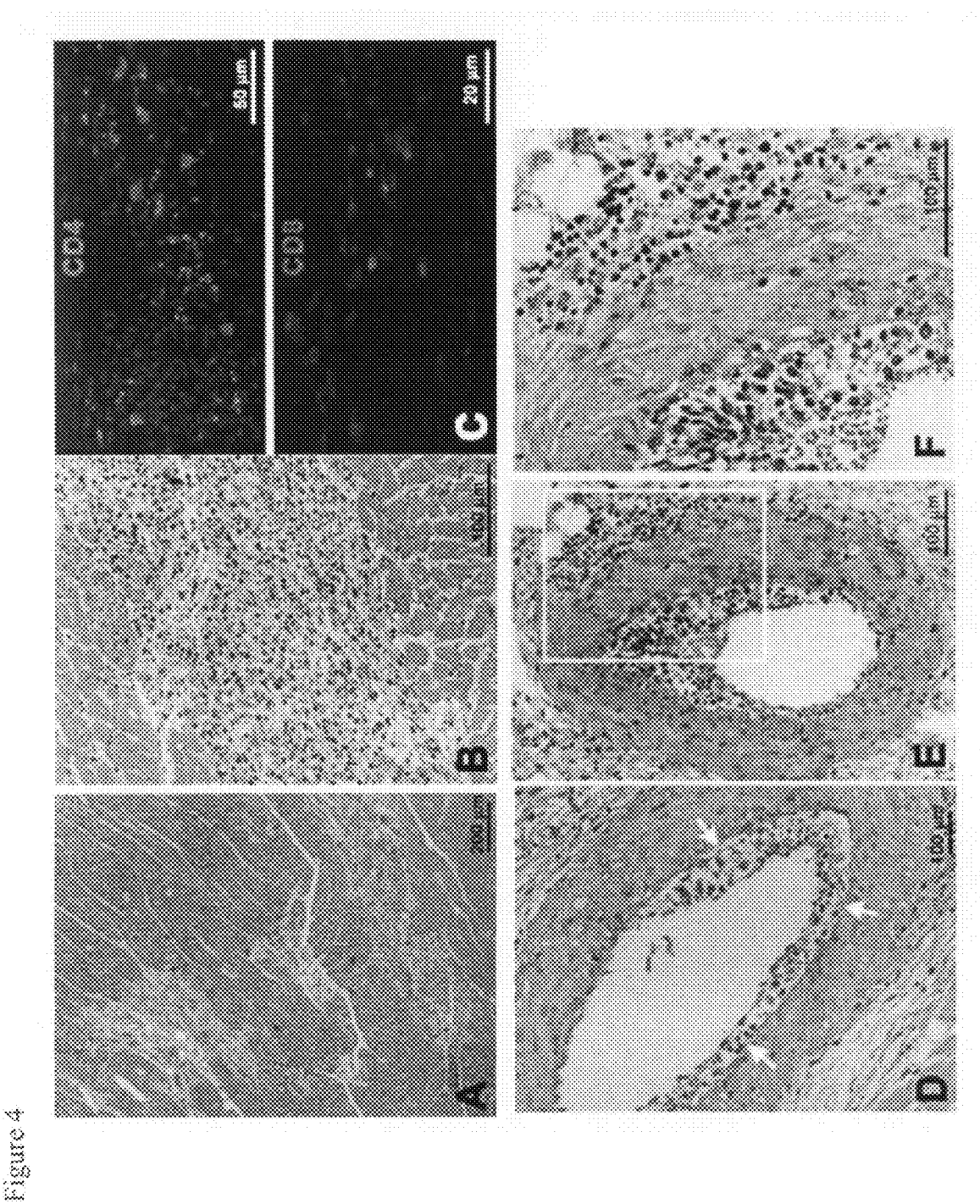
FIG. 4. Transplanted dog heart. A, B: Areas of myocardial damage occupied by inflammatory cells. C: These cells are CD4 (B lymphocytes) and CD8 (T lymphocytes) positive. D-F: Lymphocytic infiltrates in the luminal and abluminal aspects of a large and intermediate branch of LAD.

In addition, data in the transplanted dog heart model show inflammatory infiltrates in the major coronary vessels and distal branches together with initial myointimal thickening (FIG. 4). Additionally, vast zones of damage characterized by clusters of T lymphocytes, monocytes and macrophages have been detected in the ventricular myocardium. Typically, myocytes are lost and collagen accumulates in the areas of injury.

Of the 113 samples examined in this case myocardial pathology was identified in 90. These results indicate that the transplanted dog heart is a good model of cardiac allograft vasculopathy which occurs in human cardiac transplants.

A. Surgery

The female donor dog is positioned, heparin, 300 IU/kg, administered and anesthesia induced by thiopental, 6-10 mg/kg. A left lateral thoracotomy is performed, the pericardium opened, cardioplegic solution (ViaSpan) infused and the heart explanted and kept on ice. The male recipient dog is given pre-operative analgesia with oral carprofen and fentanyl patch 2 hours before surgery. Cephalic vein intravenous access is established. The animal is anesthetized (pre-anesthetics: atropine, 0.04 mg/kg, and telazol, 4 mg/kg; anesthetic: thiopental, 6-10 mg/kg), injected with heparin and placed in a warming blanket to preserve normothermia. Analgesia during surgery is provided by a bolus injection of 5 µg/kg fentanyl. Throughout surgery, anesthesia is maintained with isoflurane, 1-3% in 100% oxygen, delivered via an orotracheal tube. A neuromuscular blocking agent cisatracurium, 0.25 mg/kg, is given after depth anesthesia is established. The ECG is continuously recorded. An oral gastric tube is introduced for decompression and methylprednisolone, 500 mg, is given as initial immunosuppressive dose. Following thoracotomy and opening of the pericardium, the superior and inferior vena cava are looped with umbilical tapes and cannulated for venous drainage. The descending thoracic aorta is cannulated for arterial return and cardiopulmonary bypass initiated. The dog is maintained at 37-38° C. using a heater cooler within the cardiopulmonary bypass circuit. The aorta is cross-clamped and the heart removed, leaving a posterior remnant containing portions of the right and the left atria. The donor heart is sewn in using running, continuous 3-0 and 4-0 prolene suture. The atrial cuffs are joined first; the aorta and pulmonary artery anastomoses are then connected. The aortic clamp is removed and the heart is de-aired and allowed to recover. After reperfusion (⅓ of the time of cold ischemic period), the recipient is weaned off the extracorporeal circulation. Anticoagulation is reversed with protamine (1 mg/mg heparin given). Epicardial pacing wires and a chest tube are placed, thoracotomy closed in layers, air evacuated from the chest cavity and the tube secured to the skin. Vital signs (blood pressure, heart and respiratory rate, urine output and oxygen saturation) are monitored and recorded every hour for the first 4 hours and every two hours for the subsequent 14 hours. Arterial blood gases and electrolytes are periodically checked until the acidosis has resolved and the blood count has stabilized. Dogs remain on the ventilator overnight with Normosol-R intravenous drip, 2 ml/kg/h. On the morning of the first postoperative day, dogs that are hemodynamically stable are extubated.

B. Drug Administration

For analgesia, dogs receive a fentanyl transdermal patch, 75 µg/h, and carprofen, 4.4 mg/kg for 7 days postoperatively. Animals showing discomfort are further treated with buprenorphine, 0.02 mg/kg every 12 hours. The antibiotic cefazolin, 10 mg/kg is administered every 8 hours for 2 days. Beginning the day of transplantation, recipient dogs receive triple drug immunosuppression consisting of cyclosporine A, 18 mg/kg/day, azathioprine, 2 mg/kg/day, and methylprednisolone, 50 mg/day. The trough level of cyclosporine A is determined twice a week and immunosuppression is adjusted until a stable level of the agent is reached. Aspirin, 81 mg, is given daily to prevent venous thromboembolism.

C. Instrumentation

During transplantation, the recipient dog is chronically instrumented. A Tygon catheter is placed into the descending thoracic aorta to measure arterial pressure. Probes are implanted in the donor heart during extracorporeal circulation. A solid-state pressure gauge (Konigsberg) is inserted in the left ventricle through the apex. A Doppler-flow transducer is placed around the left circumflex coronary artery to measure blood flow and a pair of 3-MHz piezoelectric crystals are fixed on opposing endocardial surfaces at the base of the left ventricle. Wires and catheters are run subcutaneously to the intrascapular region. After recovery, dogs are trained to lie quietly on the laboratory table (64, 201-204).

D. Hemodynamics

Measurements are obtained at 10 days after each cell treatment and at sacrifice. The aortic catheter is connected to a P23 ID strain-gauge transducer to measure aortic pressure. LV pressure is determined and dP/dt is calculated. LV diameter is measured by connecting the implanted piezoelectric crystals to a transit time ultrasonic dimension gauge that generates a voltage linearly proportional to the transit time of the ultrasound traveling between the two crystals (1.55×µm/s). The analog signals are digitized at a sampling rate of 500 Hz. Systolic, diastolic, and mean arterial pressures, positive and negative dP/dt, heart rate, end-diastolic and end-systolic diameter, and pressure-diameter loop areas are evaluated (201-204).

E. Echocardiography

In conscious dogs, M-mode recordings are made from short axis views, with 2D guidance. LV chamber dimensions and wall thickness are measured in a plane below the mitral valve and perpendicular to the LV in an M-mode recording, LV chamber volume is assessed in a two-dimensional parasternal long axis view. LV volumes are calculated using the hemi-cylindrical hemi-ellipsoid model. Stroke volume is computed as the difference between LV end-systolic and end-diastolic volume. Cardiac output corresponds to the product of stroke volume and heart rate. Myocardial wall stress (WS) is calculated from the product of intraventricular pressure (LVP), radius of curvature (R) and wall thickness (h): WS=LVP×R/h.

F. Cell Infection

Progenitor cells (PCs) are infected with lentiviruses carrying EGFP (green), β-gal (blue) or RFP (red) so that the contribution of separate cell injections to the transplanted heart can be established quantitatively. In a separate set of studies, PCs to be injected are divided in three equal parts and infected respectively with lentiviruses carrying EGFP-Flag-tag under the cardiomyocyte specific α-MHC promoter, RFP-HA-tag under the SMC-specific Sm22a promoter and TFP-c-myc-tag under the EC-specific VE-cadherin promoter so that the generation of myocytes, smooth muscle cells (SMCs) and endothelial cells (ECs) in the transplanted heart are determined quantitatively by real-time RT-PCR and Western blotting by measuring the expression of the reporter constructs at the mRNA and protein level (57). These biochemical measurements are complemented with immunocytochemical determinations.

G. Cell Implantation

Figure 9:
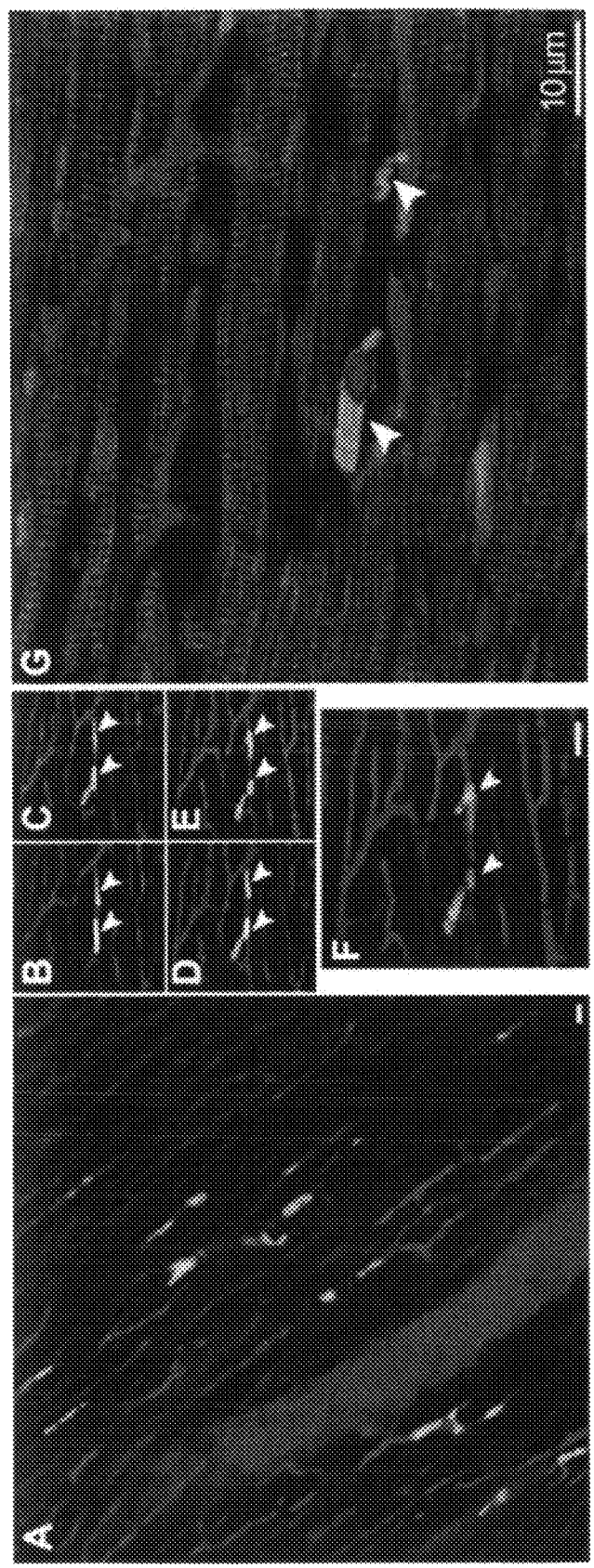
FIG. 9. PC translocation. A: Two-photon microscopy: 20 min after injection, EGFP-MPCs (green) are within the lumen of coronary vessels (red). B-F: Transcoronary migration of EGFP-MPCs; images of the same field were taken at 30 min intervals. Arrowheads point to 2 EGFP-MPCs detected in the living tissue. G: After fixation, migrated cells were identified by confocal microscopy. Myocytes are stained by cardiac myosin heavy chain (MHC: magenta).

The intra-coronary route was selected to deliver the progenitor cells to the donor heart. This route was chosen to obviate the need for multiple survival surgeries that would be required with intramyocardial injection of cells. Experiments were performed in rats subjected to brief episodes of ischemia followed by reperfusion to document that progenitor cells cross the vessel wall and reach the myocardium (183). Ischemia typically occurs at transplantation (71). Movement of EGFP-tagged MPCs (green) was assessed ex vivo by two-photon microscopy after perfusion of the coronary vasculature with rhodamine labeled dextran (red). EGFP-labeled MPCs migrate across the wall of coronary vessels and within 3 hours move into the ischemic area (FIG. 9; see ref. 183 for detail). Thus, intra-arterial delivery of MPCs leads to their extravasation and homing to the myocardial interstitium.

Figure 10:
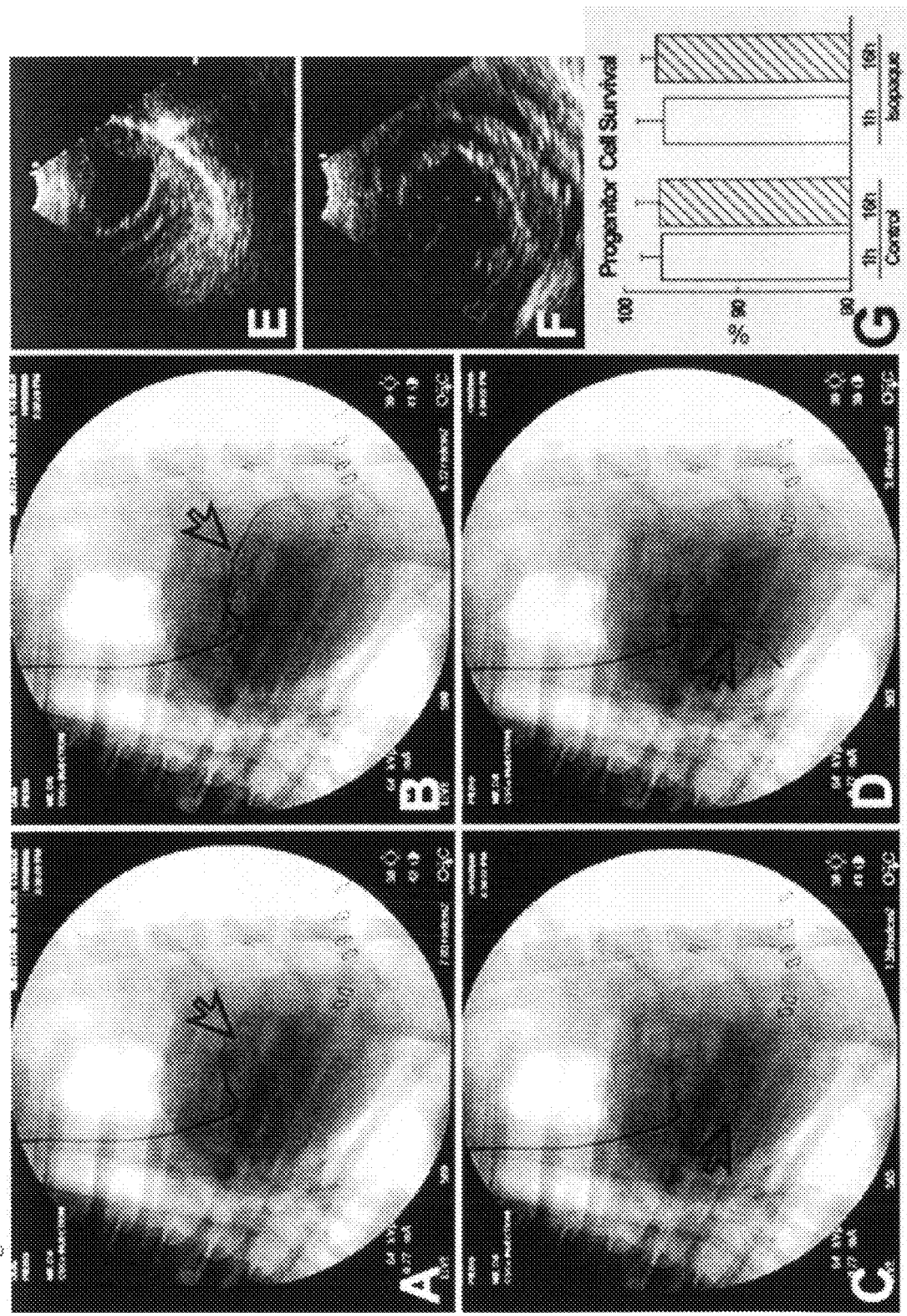
FIG. 10. Position of the catheter (A, C) and injection of cardiac PCs together with Isopaque into the circumflex coronary artery (B) and the LAD (D) of a transplanted dog. Echocardiographic images of the transplanted heart at 8 (E) and 15 days after surgery. (G) Isopaque and cell viability.

In the transplanted dog, left Amplatz or right Judkins catheter is inserted into the left or right coronary artery under fluoroscopy. Cells are suspended in 0.5-2.0 mL of Isopaque and injected. The dye allows the visualization of the coronary vasculature and delivery of cells (FIG. 10). Then, the catheter is removed and the vessels repaired. Dogs are given antibiotics baytril, 6 mg/kg, and trimethoprim/sulfa, 33 mg/kg. Isopaque does not affect cardiac PC viability for as long as 16 hours. During the procedure, cardiac PCs are exposed to Isopaque for less than 5 min.

H. Generation of Immunocompatible Myocardium

Figure 3:
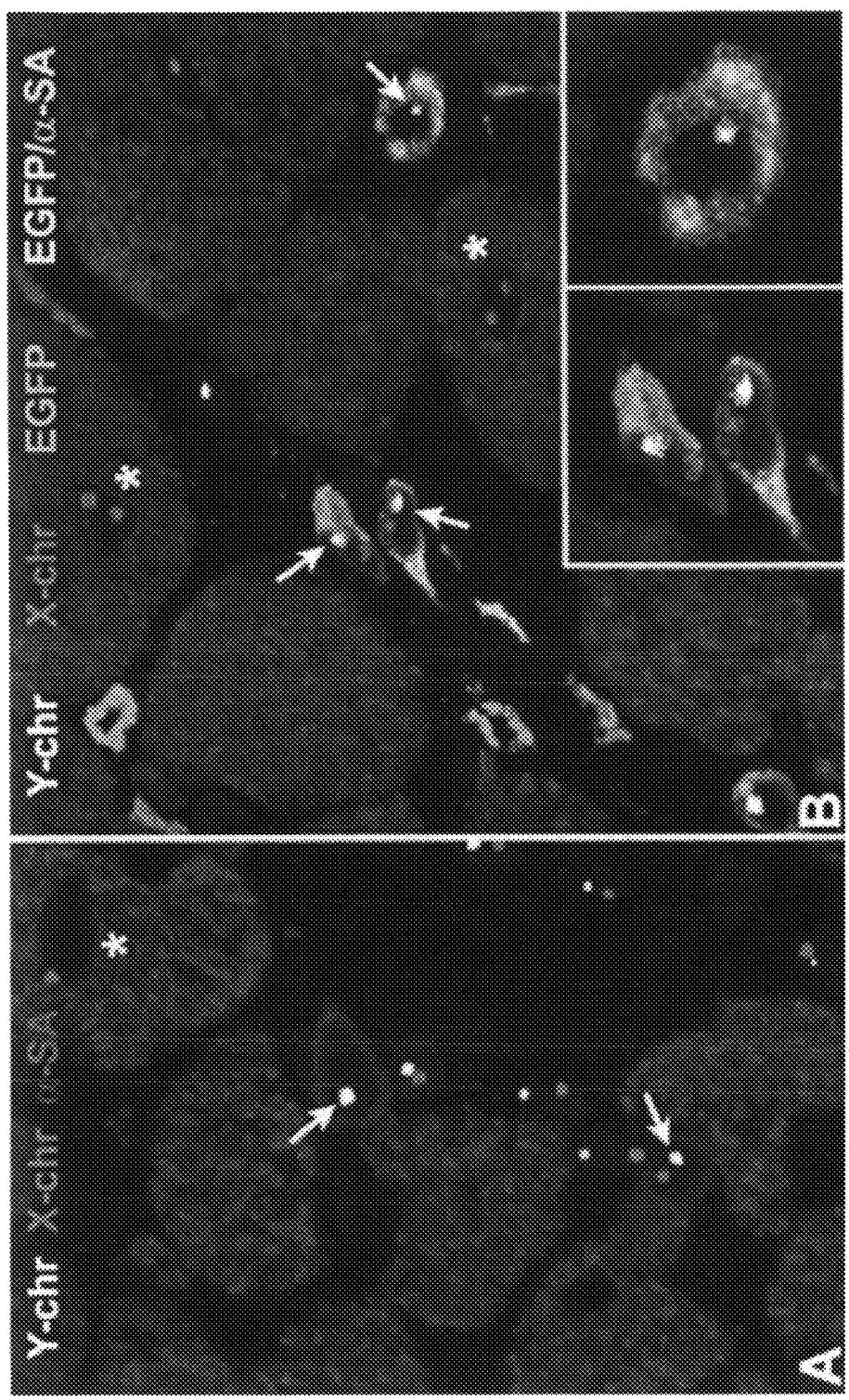
FIG. 3. Chimerism of the dog heart. Donor female heart transplanted in male recipient. Subsequently the donor heart was injected with autologous-recipient EGFP-positive PCs. Several small developing myocytes are present (A, B: α-SA: red). These new myocytes are also EGFP-positive (B: α-SA- EGFP, yellow). Three of these cells are shown at higher magnification in the inset (B). Analysis of sex-chromosomes documented the male genotype of the forming myocytes (arrows) which carried at most one Y-chr (white dots) and one X-chr (magenta dots). Female recipient myocytes show at most two X-chr (*).

In these initial studies, VPCs and MPCs were not separated and the PC pool was isolated from the explanted heart and expanded in vitro. Cells were infected with EGFP lentivirus (65% efficiency). Male EGFP-PCs were given 15 and 24 days after transplantation and the donor heart was examined 6 days after the second treatment, i.e., 30 days following surgery. The heart was sliced in 22 sections ~4 mm each and several samples were obtained from each section (FIG. 11A): 114 samples were analyzed histologically. A similar protocol is used in all studies discussed in Examples 2-5. Clusters of newly formed EGFP-positive myocytes and coronary vessels (FIG. 11B-E) were detected in 109 of 114 specimens of the left and right ventricle. The ability of EGFP-PCs to differentiate into myocytes and SMCs was confirmed by detection of myocyte transcription factors, GATA4 and Nkx2.5, and the SMC transcription factor, GATA6 (FIG. 11F). The detection of the Y chromosome (Y-chr) confirmed the male genotype of the regenerated myocytes (FIG. 11G-H). As shown before, at most one X- and Y-chr were identified in the formed cells excluding cell fusion (FIG. 3). In contrast, at most 2 X-chr were seen in donor cardiac cells documenting their female genotype. The engraftment and survival of male EGFP-PCs was confirmed by PCR for EGFP DNA and the Sry gene located in the Y-chromosome (FIG. 11I and J). Random sampling of tissue from kidney, spleen, lung and liver failed to reveal DNA sequences for EGFP by PCR (FIG. 11I). Thus, at 15 and 6 days after the first and second injection no EGFP-PCs were found to be engrafted outside of the heart. Comparable findings were obtained in a second dog in which male EGFP-PCs were given 15 and 22 days after transplant and the animal was sacrificed 2 weeks later, i.e., 45 days after surgery.

I. Immunohistochemistry with Quantum Dots, Fish and Confocal Microscopy

The recognition of regenerated male myocardium within the female donor heart requires immunolabeling of structures and confocal microscopy. To evaluate the lineage commitment of differentiating cells, antibodies for the following proteins are utilized. Markers for myocytes include GATA4, Nkx2.5, MEF2C, α-SA, α-cardiac actinin, troponin I, troponin T, cardiac MHC, atrial and ventricular myosin light chain (MLC), connexin 43 and N-cadherin; for SMCs, GATA-6, TGF-β1 receptor, α-SMA and calponin; and for ECs, Ets1, Vezf, CD31 and vWf (14, 47, 48, 51, 57, 59, 64, 137, 139). Y- and X-chr are identified by FISH (14, 47, 51, 57, 139) with canine specific probes (Cambio).

Example 2

Implantation of BMPCs from the Recipient into the Transplanted Donor Heart Generates Immunocompatible Coronary Vessels and Myocytes Improving the Evolution of the Cardiac Graft

This Example demonstrates that bone marrow progenitor cells (BMPCs) can acquire the cardiomyocyte, and vascular smooth muscle cell (SMC) and endothelial cell (EC) lineages in support of the therapeutic efficacy of BMPCs. Additionally, the consequences of cell fusion events and paracrine effects on myocardial regeneration are addressed.

A. Transdifferentiation

To date, the hematopoietic stem cell appears to be the most versatile stem cell in crossing lineage boundaries and the most prone to break the law of tissue fidelity (40, 205). Early studies on BMPC differentiation into myocardium have generated great enthusiasm (47, 51, 52, 168) but other observations have rejected the initial results (41-43) and promoted a wave of skepticism about the therapeutic potential of BMPCs for the injured heart (46, 206). The major criticisms include inaccurate interpretation of the original data due to autofluorescence artifacts and the lack of genetic markers for the recognition of the donor BMPCs and their progeny (41-43, 46, 206).

To address these issues, female infarcted mice were injected with male BMPCs obtained from transgenic mice in which EGFP was under the control of the ubiquitous β-actin promoter and the consequences of this intervention on post-infarction remodeling were determined. In another set of experiments donor BMPCs were collected from male mice carrying EGFP or c-myc-tagged nuclear Akt transgene under the control of α-MHC promoter (FIG. 12A). Thus, the destiny of BMPCs within the recipient heart was determined by genetic tagging with EGFP, cell fate tracking with EGFP and c-myc, cell genotyping by sex-chr identification (FIGS. 12B and C), EGFP and c-myc gene detection by PCR, mRNA transcripts for EGFP and c-myc-tag by RT-PCR, and protein expression for EGFP and c-myc-tag by Western blotting. Additionally, a critical part of the experiments was the development of a methodology in which primary antibodies are directly labeled with quantum dots (36, 139, 207). This protocol eliminates the need for secondary antibody and avoids the interference of autofluorescence in the specificity of the reaction (57).

Figure 13A:
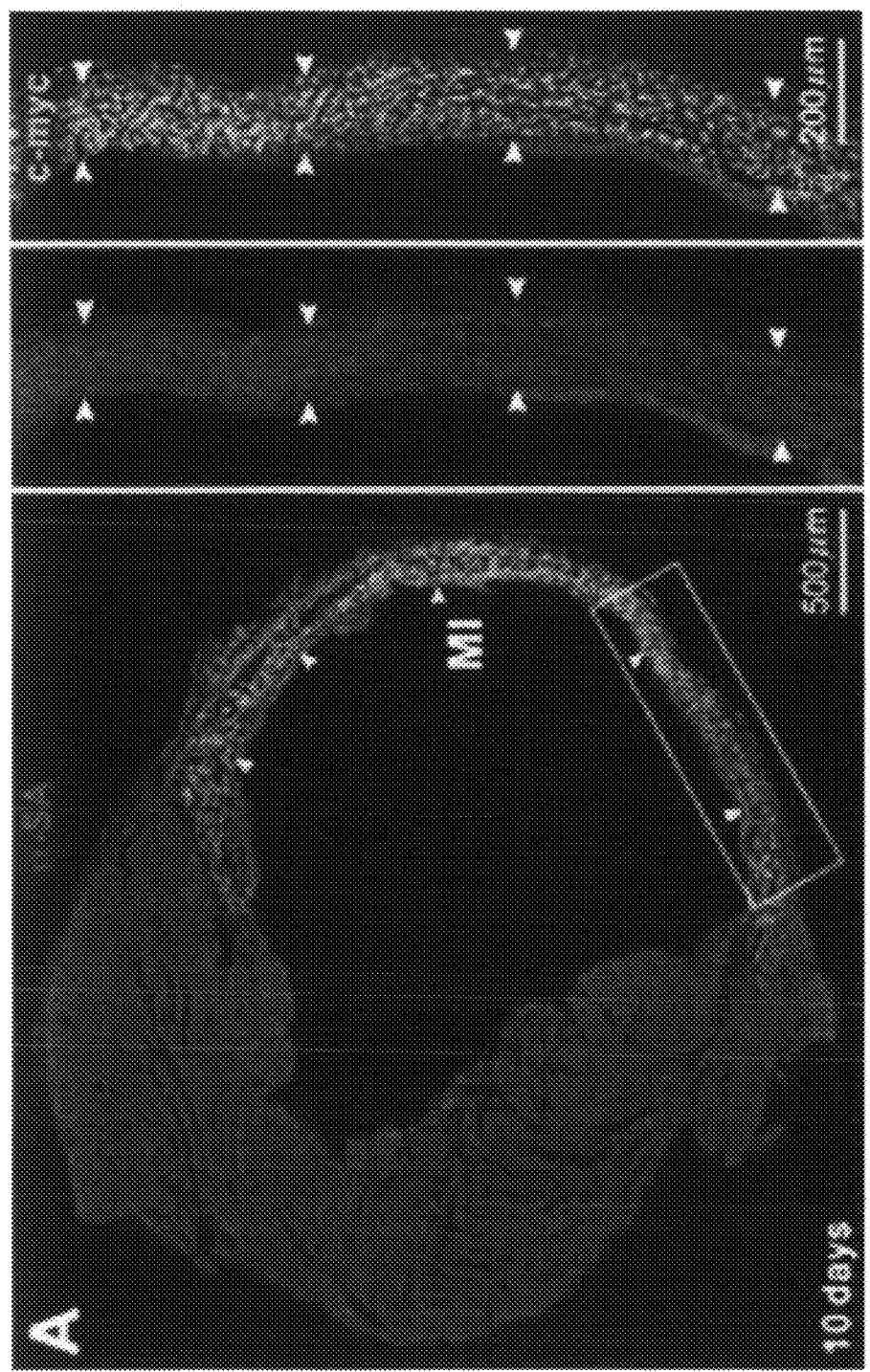
FIG. 13. A: BMPCs from a-MHC-c-myc-tagged-nuc-Akt mice regenerated myocytes ($\alpha$-SA: red; c-myc: green; arrowheads). B: Infarcts treated with BMPCs from $\beta$-actin-EGFP mice. EP: epicardium; EN: endocardium. Left, central and right panels show EGFP (green), new myocytes (MHC, red) and their merge. Arrows: non regenerated infarct. C: Left, central and right panels illustrate new myocytes (MHC, red), distribution of Y-chr (white) and their merge. Arrows: non regenerated infarct. D: Higher magnification of new myocytes within the formed myocardium. The restored myocyte mass increased with time. E: DNA sequences (see SEQ ID NOS.: 5-10) of EGFP and c-myc-tag by PCR. DNA from the tail of donor TG and WT mice was employed as +and –control. F: Transcripts and sequences (see SEQ ID NOS.: 11-16) for EGFP and c-myc-tag by RT-PCR in infarcted treated hearts (+). Absence of RT reaction (–). RNA from hearts of TG and WT was employed as + and – control G: EGFP and c-myc-tag protein by Western blotting.
Figure 13:
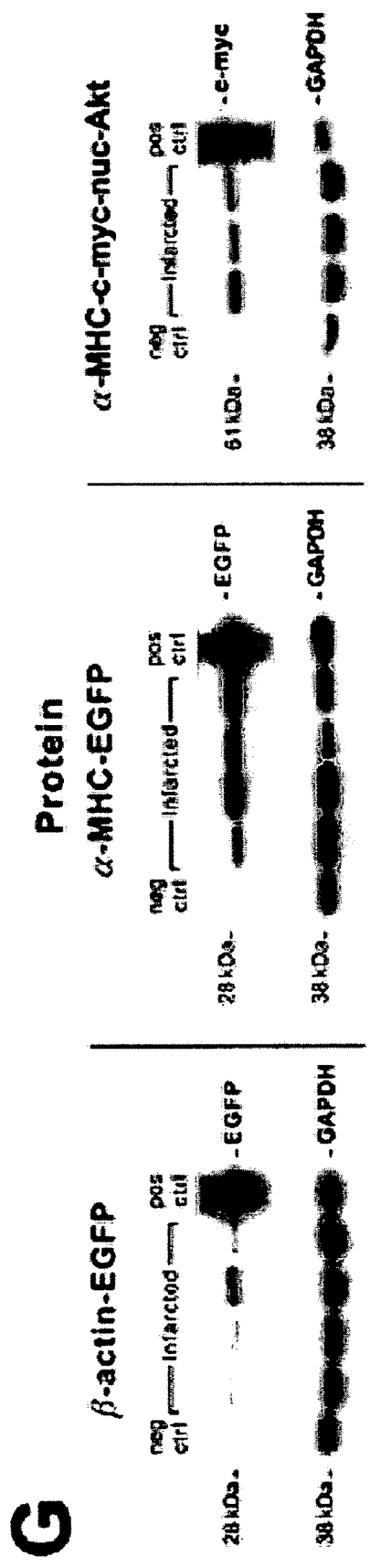

The results show that BMPCs integrate within the host heart where they establish temporary niches which create the microenvironment necessary for the engrafted cells to acquire the cardiac fate and form de novo myocardium (FIG. 13; 57). These data are consistent with our hypothesis and may offer mechanistic insights on the positive results recently obtained in double blind clinical trials (208, 209). These findings suggest that myocardial regeneration is a likely possibility and BMPCs may have implications for the treatment of the transplanted heart.

B. Cell Fusion

Figure 2:
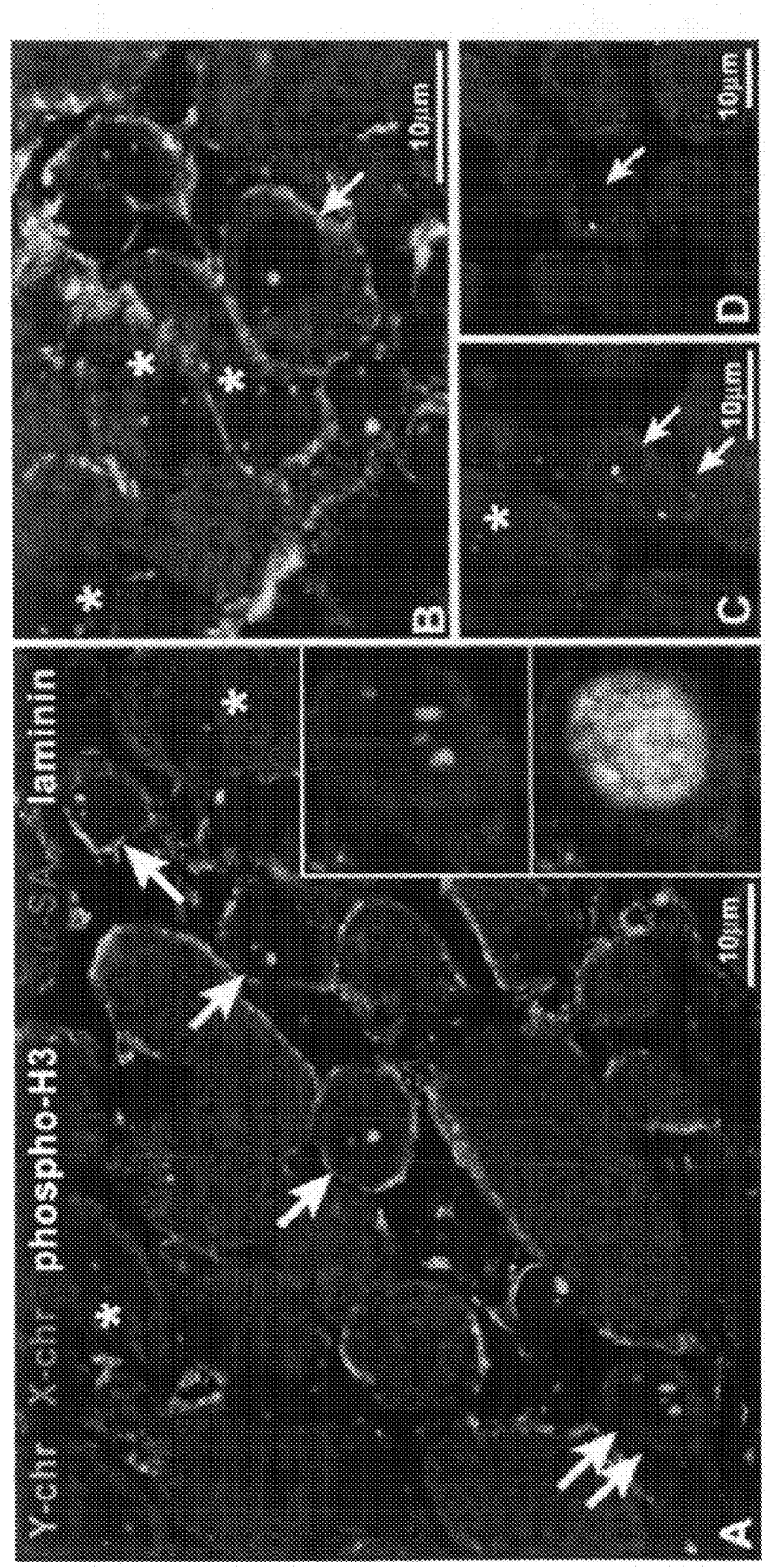
FIG. 2. Cardiac chimerism. A 67-year-old man died 9 days after sex mismatched heart transplant. The donor female heart showed regeneration foci characterized by clusters of developing myocytes. A-D: α-SA: red; nuclei: DAPI, blue. Myocyte boundaries were defined by laminin (yellow). The analysis of sex-chromosomes by FISH documented the male genotype of the new myocytes (arrows) which carried at most one Y-chr (green-dots) and one X-chr (magenta-dots). Large myocytes (asterisks) had a female genotype (two X-chr). A: one new myocyte contained two sets of X- and Y-chr suggesting cell fusion (double arrows). However, phospho-H3 (inset, white) demonstrated mitotic division and excluded cell fusion. Similar examples were found in other transplanted hearts.
Figure 14:
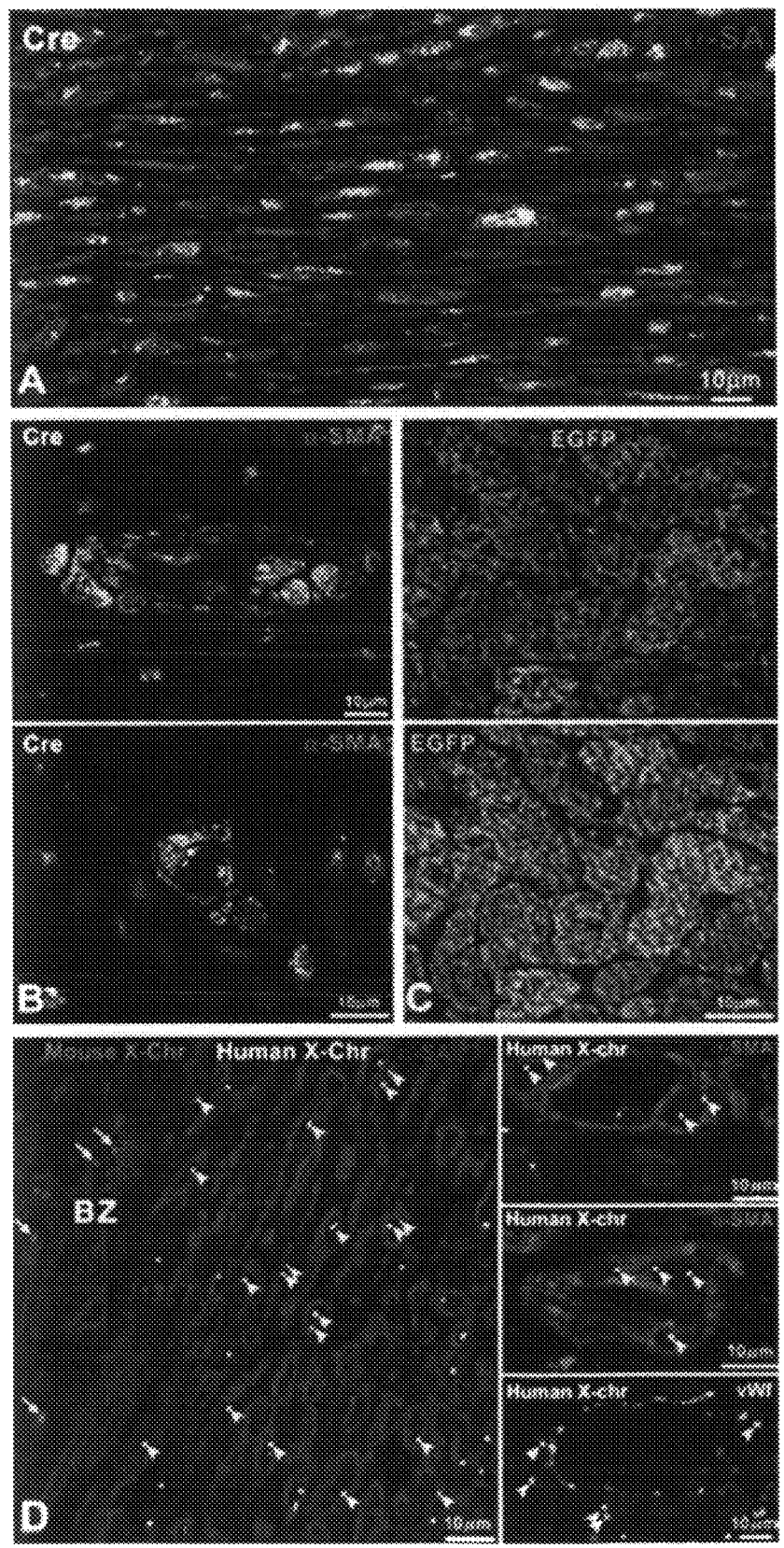
FIG. 14. Lack of cell fusion. Regenerated human myocytes (A) and vessels (B) are Cre-recombinase positive (white) but EGFP-negative. C: Positive control: EGFP-myocytes of mice in which EGFP was driven by $\alpha$-MHC promoter. D: Myocytes and vessels show at most two human X-chr (white dots; arrowheads). Mouse X-Chr (magenta dots; arrows) are present in myocytes bordering the infarct (BZ). See ref. 139 for detail.

In several studies of myocardial regeneration, we have never found examples of fusion between BMPCs or other progenitor cells with resident cardiac cells (47, 48, 51, 59, 137, 139). We have investigated the possibility of cell fusion in several conditions by measuring the number of sex chromosomes in newly formed cardiomyocytes and coronary vessels (14, 47, 51, 57, 139, 217). For example, with this approach, we have excluded that male myocytes and vessels present in female transplanted hearts are the product of cell fusion (see FIG. 2). Additionally, we have employed the Cre-Lox genetic system to evaluate whether human MPCs can form human myocardium within the infarcted mouse or rat heart (139) and whether myocardial regeneration in these models is, at least in part, the product of fusion events. We have found no indication that cell fusion contributes to cardiac repair (FIG. 14). To exclude the possibility that heterokaryons are formed when the donor hear is colonized with recipient progenitor cells, the number of sex chromosomes is measured in the newly formed structures to assess the participation of cell fusion in myocardial regeneration.

C. Paracrine Effects

We test the possibility of a paracrine effect of administered progenitor cells by giving BrdU chronically after transplantation by a well established protocol (51, 57, 139). Over time, cumulative BrdU labeling of female myocytes and coronary vessels provides a quantitative measurement of the cellular responses of the donor heart to the injection of recipient male progenitor cells. Additionally, the fraction of cycling female myocytes, ECs and SMCs at sacrifice is determined by Ki67, MCM5 and phospho-H3 labeling to assess the characteristics of the donor myocardium at the end of the study. Finally, the number of female myocytes and vessels is determined to define the composition of the donor heart and its changes with time. The injected cells could also attenuate cell death mechanisms. Thus, apoptosis of EGFP-, β-Gal- or RFP-negative and Y-chr negative cells is measured. Similarly, the contribution of male myocytes and vessels to the restoration of immunocompatible structures within the non-immunocompatible myocardium is evaluated.

D. Implantation of BMPCs in Transplanted Donor Heart in Canines (1) Cell Preparation The bone marrow is harvested from the iliac crests through a Jamshidi needle (13 G×2") (218); ~10 ml of bone marrow is obtained. This protocol yields a total of $20 \times 10^8$ mononuclear cells in each recipient dog. Following lysis of red blood cells in NH4Cl/K, cells are enriched by equilibrium centrifugation over a cushion of Ficoll-Hypaque-400 at a density of 1.077 g/ml. For lineage-depletion, mononuclear cells are incubated with immunomagnetic beads conjugated with monoclonal antibodies for CD3 (T lymphocytes), CD20 (B lymphocytes), CD33 (myeloid progenitors), CD14 and CD15 (monocytes). The lineage-negative fraction is exposed to c-kit-conjugated-immunobeads (clone AC126). A small aliquot is analyzed by FACS to confirm the purity of the preparation (47, 168). Cells are stained with c-kit-A3C6E2 antibody that does not cross-react with the epitope recognized by the AC126 antibody; $~10 \times 10^6$ c-kit-positive BMPCs are collected from each recipient dog. Since at most 5 injections of BMPCs is done in each dog, $2 \times 10^6$ cells are injected each time.

(2) Intervals

One month after transplantation, dogs are anesthetized for left heart catheterization and cell injection (Group 1; EGFP-labeled cells). This protocol is then applied twice for the next month (Group 2; β-Gal-labeled cells) and subsequently twice for an additional month (Group 3; RFP-labeled cells). Group 1 animals are sacrificed one month after a single cell injection, 2 months after transplantation; Group 2 animals are sacrificed one month after the last of 3 cell injections, 3 months after transplantation; and Group 3 animals are sacrificed one month after the last of 5 cell injections, 4 months after transplantation. Another group of animals, Group 4, is injected bi-weekly for 2 months (5 injections) with BMPCs infected with three lentiviruses carrying reporter genes driven by cell lineage specific promoters. These animals are sacrificed 4 months after transplantation mimicking Group 3. The end-points indicated here are formulated to evaluate the progressive accumulation of immunocompatible myocardium. In Groups 1-3, BrdU is injected twice a day (50 mg/kg b.w.× 2) to label forming cells over time (64).

(3) Immunocompatible Myocytes and Coronary Vessels

Three methods are used to detect immunocompatible myocytes and vessels within the donor heart: a) Genetic tagging/clonal marking; b) Real-time RT-PCR and Western blotting for reporter genes; and c) Structural analysis. Because of these objectives, at sacrifice the donor heart is subdivided into two parts: one for genetic tagging and biochemical analysis of BMPC transdifferentiation and the second for the quantitative characterization of the contribution of donor and regenerated recipient myocardium to the transplanted heart.

a) Genetic tagging/clonal marking (see Example 4): The objective is to document whether the site of integration of the EGFP, β-gal and RFP lentivirus in BMPCs is found in the committed progeny. This demonstrates that BMPCs transdifferentiate and have the ability to form de novo myocardium.

b) Real-time RT-PCR and Western blotting for reporter genes (see Example 4).

c) Structural analysis (see Example 3): The morphometric approach developed in our laboratory allows us to measure the proportion of newly formed male myocardial structures and resident female myocardium.

The results of these experiments in canines is expected to show that BMPCs isolated from the recipient male dog will differentiate into myocytes, smooth muscle cells, and endothelial cells and generate immunocompatible myocardium and myocardial vessels in the female donor heart. No evidence of fusion events between the male bone marrow progenitor cells and the donor female myocardial cells is expected to be observed.

Example 3

Implantation of Vascular Progenitor Cells from the Recipient into the Transplanted Donor Heart Generates Immunocompatible Coronary Vessels Improving the Evolution of the Cardiac Graft Cardiac allograft vasculopathy (CAV) is a major pathological event which severely affects the unfavorable evolution of the transplanted heart (72, 85, 91-93, 108, 109). In this Example, the therapeutic potential of vascular progenitor cells (VPCs) is defined. This cell category is the most powerful for the replacement of the coronary circulation of the donor heart with immunocompatible vessels and thus, the possibility to introduce stem cell therapy for the treatment of coronary artery disease is dramatically advanced. Moreover, the documentation that progenitor cells with angiogenic properties reside in the heart questions the notion that the bone marrow is the exclusive reservoir or source of stem cells for therapeutic vasculogenesis and points to VPCs as the cell of choice for biological bypass. Two issues are addressed in this Example: cell engraftment and necessity to create the various portions of the coronary circulation.

A. Engraftment

Figure 17E:
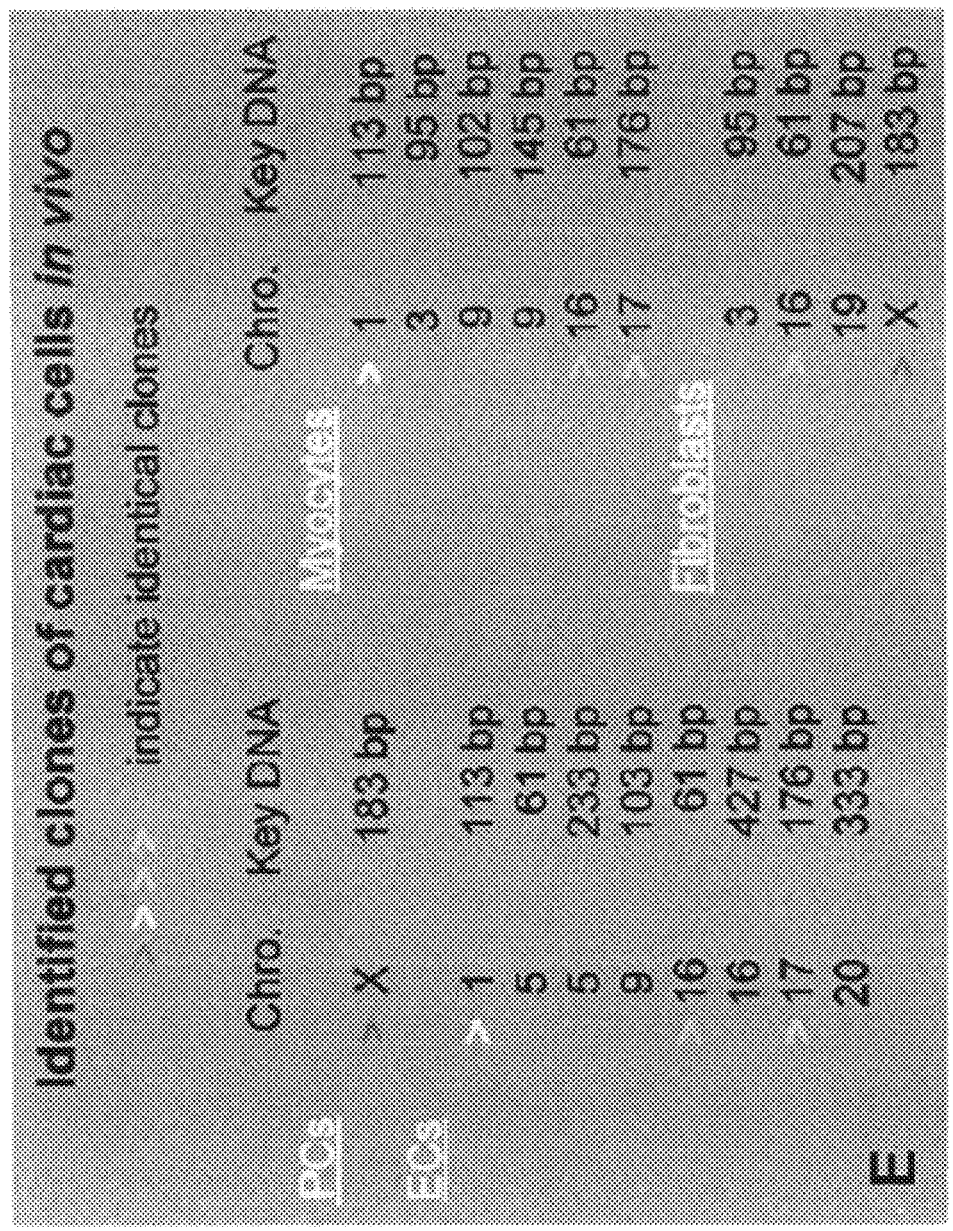
FIG. 17. AKANE protocol (Amplification of the Key DNA sequence Adjacent to an integrated provirus by Nested PCR coupled with Enzymatic digestion and ligation of the genome). This method corresponds to an inverse PCR which is the most sensitive strategy for the amplification of unknown DNA sequences that flank a region of known sequence. The primers are oriented in the reverse direction of the usual orientation and the template for the reverse primers is a restriction fragment that has been ligated and self-circularized. A: The AKANE method was first developed in human cardiac PCs infected with an EGFP lentivirus in vitro at low efficiency (~10%). Genomic DNA was extracted, digested with EcoR1 and ligated with T4 DNA ligase to circularize the DNA fragments. Two sets of PCR primers were used to amplify the coding region of the EGFP gene: (1) one set of conventional primers that produced a single band of 164 bp and (2) a set of primers with opposite directions that amplify only circularized DNA and produced a single band of 143 bp. B: To determine the clonal profile of the infected human cardiac PCs, extracted DNA was digested with Taql, ligated with T4 DNA ligase and re-linearized with Hind3. One round of PCR and two additional nested PCR were performed. The PCR primers employed in the first (1st) and second (2nd) amplification round were designed in the region of Long Terminal Repeat, LTR, which is commonly located at the 5'- and 3'-sides of the lentiviral genome. The PCR primers employed in the third round (3rd) were specific for either the 5'- or the 3'-side of the site of integration. In all cases, primers were oriented in the opposite direction. No clear bands were detected after the 1st round because of the low amount of the target templates in the sample. Arrows of the same color point to the corresponding bands in different lanes. As expected, the size of the amplicons decreased by 112 by for the 5'-side products and 138 bp for the 3'-side products. The seven bands indicated by the arrows reflect different sites of integration of the EGFP lentivirus in the genomic DNA of the infected human cardiac PCs. Two of the amplified bands were excised from the gel and the DNA was re-amplified as shown in the last two lanes. DNA sequencing analysis of the two re-amplified bands demonstrated that the DNA contained the proviral genome together with the key DNA sequence of the human genome. The human genome is linked to the proviral DNA through the integration site and the Taql restriction site. The sites of integration were located in chromosomes 20 and 6, respectively. C: Multiple clones were identified in human cardiac PCs, and the identified chromosomes are listed. D: After EGFP lentiviral infection (~80% efficiency), human cardiac PCs were implanted in infarcted rats that were sacrificed one month later. Cardiac cells were enzymatically digested and separated in cardiac PCs, ECs, fibroblasts and myocytes. By the AKANE protocol, various clones were identified: one clone in c-kit positive cells, eight clones in ECs, four clones in fibroblasts, and six clones in myocytes. DNA sequencing analysis demonstrated that the DNA contained the proviral genome together with the key DNA sequence of the human genome. One of the detected clones was present in all committed cell types indicating that these cells constitute the progeny of one of the injected c-kit positive cardiac PCs which underwent multilineage differentiation. E: An example of the detected sites of integration in the various cardiac cells of the same animal are listed. Some clones were common to different category of the cells (arrowheads). The distribution of the integration sites, again, confirmed the random integration of the EGFP lentivirus into the human genome.

The criteria that govern myocardial regeneration and replacement of damaged non-immunocompatible tissue with functionally competent immunocompatible myocardium involve the ability of the delivered progenitor cells to home to or in proximity of the injured sites together with the permissive behavior of the donor myocardium (47, 48, 50-53, 59, 137, 139, 173, 221). These variables dictate the number of cells that actually engraft within the hostile environment of the target organ which, in turn, condition the efficacy of cell therapy. Engraftment necessitates a surrounding where the cells can survive, divide and differentiate (64, 163, 165-167). Based on data with BMPCs (57) and treated transplanted hearts (FIG. 15), cell engraftment is completed in a few days. Junctional and adhesion proteins are present on the implanted cells documenting a successful interaction between progenitor cells and resident cells; connexin 43 and 45, and N- and E-cadherin have been found between progenitor cells and myocytes or fibroblasts which operate as supporting cells (57, 137, 169). Also, apoptosis occurs in non-engrafted cells and cell division occurs in engrafted cells (FIG. 17). Thus, the destiny of VPCs is established by measuring cell death and proliferation and their integration with resident cardiac cells 2-5 days after injection.

B. Coronary Vasculature

The identification and characterization of a coronary VPC discussed above raises the possibility that the heart harbors a coronary VPC which regulates the turnover, growth and differentiation of the coronary circulation. To test this possibility, human VPCs were infected with a lentivirus expressing EGFP and were subsequently examined for the ability to create functionally competent coronary vessels in dogs with critical coronary artery stenosis. These VPCs formed human conductive and intermediate-sized coronary arteries together with small resistance arterioles and capillary profiles within the immunosuppressed recipient myocardium, restoring in part myocardial blood flow to the distal portion of the heart (FIG. 16). Thus, VPCs may be implemented for the replacement of coronary vessels affected by allograft vasculopathy in the transplanted dog heart.

As described in Example 2 with BMPCs, at most 5 injections of VPCs are done in each dog; $2\times10^6$ cells are injected each time.

C. Analysis of the Transplanted Heart

At sacrifice the donor heart is subdivided into two parts: one for the identification by genetic tagging/clonal marking and biochemical-molecular parameters of progenitor cell differentiation in cardiac lineages (see Example 4) and the second for the quantitative characterization of the contribution of donor and regenerated recipient myocardium to the transplanted heart discussed below.

The first portion of the heart is enzymatically digested (see Example 4). The second portion of the heart is utilized for the evaluation of myocytes and coronary vessels of donor and recipient origin. A branch of the coronary artery is cannulated and the heart and coronary vasculature is fixed by perfusion with formalin. Briefly, the chest is opened, 20,000 units of heparin is given intravenously, and vessels originating from the aortic arch is ligated. The heart is arrested in diastole, the descending aorta ligated and cannulated. The heart is perfused with phosphate buffer and before perfusion with formalin, a portion of the heart is removed for cell isolation and the studies discussed in Example 4 (64, 232-237). The expression of EGFP, β-gal or RFP together with the localization of the Y-chromosome allows us to distinguish structures mediated by growth and differentiation of progenitor cells at different time points following cardiac transplantation. In contrast, cardiomyocytes and coronary vessels negative for these reporter proteins and showing the female genotype constitute the remaining component of the donor myocardium.

D. Cell Engraftment

The ability of male EGFP-, β-gal- and RFP-tagged VPCs to home and form junctional complexes with resident female cardiac cells is determined as previously performed (57, 137, 139, 169). This analysis includes the identification of connexin 43, connexin 45, N-cadherin, E-cadherin, and L-selectin. The number of actually engrafted cells is measured quantitatively (57).

E. Cell Growth and Death

The progeny of the injected cells is recognized by the presence of EGFP, β-gal and RFP. This labeling is combined with the detection of BrdU indicative of newly formed cells and cumulative growth (169). This measurement is complemented by the expression of MCM5, Ki67 and phospho-H3 to recognize the fraction of cycling cells (MCM5, Ki67) and in mitosis (phospho-H3). The degree of apoptosis and necrosis in VPCs and their progeny is also measured (139, 169, 232-237).

F. Coronary Vasculature and Cardiomyocytes

Morphometric measurements of coronary vessels require a specific approach. This technique and its theoretical principles have been previously described (136). This protocol applies to the analysis of capillaries as well (40, 47, 48, 59). Classes of vessels positive for EGFP, β-gal or RFP together with the Y-chromosome is measured separately. An identical analysis is conducted in vessels which are negative for these markers. Thus, an estimation of the immunocompatible and non-immunocompatible coronary vasculature is obtained.

The number of newly formed and existing myocytes is measured quantitatively by a protocol developed previously which includes measurements in tissue sections and isolated cells (136). Sampling for coronary circulation and cardiomyocytes: see ref. 136.

The results of these experiments are expected to show that vascular progenitor cells isolated from the explanted heart of the male recipient dog will engraft in the donor female heart after administration and differentiate into predominantly smooth muscle cells and endothelial cells. The differentiated cells will assemble into immunocompatible coronary vasculature (coronary arteries, arterioles, and capillaries) similar to that formed after the administration of human vascular progenitor cells (see section B above).

Example 4

Implantation of MPCs from the Recipient into the Transplanted Donor Heart Generates Immunocompatible Cardiomyocytes Improving the Evolution of the Cardiac Graft Myocyte progenitor cells (MPCs) are programmed to give rise to cardiomyocytes and these cells should be superior to bone marrow progenitor cells (BMPCs) and vascular progenitor cells (VPCs) for replacement of lost muscle mass. This is suggested by in vitro results in which the differentiated progenies of MPCs and VPCs were compared (see FIG. 7). BMPCs differentiate into myocytes (239-241), smooth muscle cells (242, 243) and endothelial cells (244, 245) in vitro. However, the relative proportion of these cell types in the same preparation is difficult to obtain.

To address the issue of the regenerative capacity of the different progenitor cell classes (e.g. BMPCs, MPCs, and VPCs), the quantitative measurements of newly formed myocytes and vessels based on morphometric principles and immunolabeling (Example 3) is complemented with a novel genetic-molecular assay developed previously in our laboratory (246). Thus, two complementary methods are used: a genetic-molecular assay and a structural assay. Genetic tagging is discussed below together with a series of other molecular determinations.

A lentivirus expressing EGFP, β-gal and RFP is employed for in vitro infection of BMPCs, VPCs and MPCs. The detection of the lentiviral integration site is based on the premise that it contains two restriction enzyme (RE) cleavage sites at a reasonable distance (50-2000 bp) from the lentiviral LTRs located at the 3' and 5' sites of the viral genome. Following the cleavage of the genomic DNA with the RE, DNA products are self-ligated to produce circularized DNA. This step creates a genomic sequence of a length that is variable in view of the random location of the RE site within the region of the dog genome flanking the viral DNA. The unknown lentiviral flanking region is entrapped between two known sequences and can be, therefore, amplified by PCR and resolved on gel; each band corresponds to one insertion site. Data have been obtained after intramyocardial injection of human cardiac progenitor cells in immunosuppressed infarcted rats to validate this novel approach (246; FIG. 17).

The data indicate that similarities exist between forming myocardium (36, 51, 57, 59, 64, 139) and late-fetal and postnatal cardiac maturation (136, 247, 248). The volume of myocytes is comparable although differences in number exist; regeneration tends to recapitulate the processes present in the fetal-neonatal heart (249, 250). Accordingly, the prenatal and postnatal heart are used for comparison.

Hearts from female donors are transplanted into male recipients as described in Example 1. Progenitor cells isolated from the male explanted heart are infected with lentivirus carrying EGFP, β-gal and RFP. The infected progenitor cells are then injected into the transplanted donor heart. At most 5 injections of progenitor cells are done in each dog; $2 \times 10^6$ cells are injected each time.

Molecular assays and immunocytochemistry are used to identify the time-course of myocardial regeneration in the transplanted heart and in the developing heart (fetal dog heart at 40 and 60 days of gestation, 1-2 days after birth, at the time of weaning, 4-5 weeks, and 8 months). The expression of transcription factors that control myogenesis and vasculogenesis is determined (247, 248, 251-253). Moreover, membrane and cytoplasmic proteins specific of myocytes, smooth muscle cells and endothelial cells are studied (254-257). Molecular and cytochemical detections are both relevant to obtain information with two complementary methods and ensure that protein expression is properly distributed within cells. Postnatally, apoptosis decreases rapidly and this adaptation is paralleled by a reduction in myocyte formation coupled with binucleation of the enlarging myocytes (258-260). Myocyte karyokinesis in the absence of cytokinesis is accompanied by downregulation of the transcription factor Tsc (tuberous sclerosis complex) and upregulation of Gax (growth arrest gene). Similar adaptations may occur in the transplanted heart.

Transplanted Heart: At sacrifice, in a portion of the heart, a coronary artery branch is cannulated and cardiac cells are enzymatically dissociated with collagenase for biochemical-molecular determinations (232-237). Large myocytes of donor origin and small cardiac cells (newly formed myocytes and non-myocytes) of both donor and recipient origin are separated by Ficoll gradient and differential centrifugation (246). Within the small cells, the progeny of the injected progenitor cells are sorted by FACS based on the presence of EGFP, β-gal and RFP. The spontaneous fluorescence of EGFP- and RFP-positive cells allow their direct collection. When β-gal-positive progenitor cells are injected, the isolated cells are fixed in 4% paraformaldehyde for 15 min, stained with anti β-gal antibody (168) and sorted by FACS. Cells are employed directly for RNA extraction and real-time RT-PCR. For genetic tagging, an additional step is required. Progenitor cells are sorted by FACS on the basis of c-kit and flk1 expression (47, 59, 64, 139). C-kit-negative cells are subdivided in CD31-positive (endothelial cells), calponin-positive (smooth muscle cells), α-SA-positive (myocytes) and procollagen-I-positive (fibroblasts) cells.

Genetic tagging: Genomic DNA is extracted and employed for the detection of the site of viral integration. Importantly, each cell population isolated from each heart is processed separately according to the AKANE protocol (see FIG. 17 and legend). Primers are designed to include a portion of the coding regions of EGFP, β-gal and RFP to distinguish the three viral genomes. Amplified DNA is run on agarose gel. Bands are cut, DNA extracted and sequenced from both ends to determine the insertion site of each clone (246).

Biochemical-molecular determinations: These analyses are performed in freshly isolated EGFP-, β-gal- and RFP-positive cells and whole lysates of fetal, neonatal and young adult hearts by real time RT-PCR (139, 263). Western blotting is also employed. These analyses are complemented by the detection of proteins by immunocytochemistry. For real-time RT-PCR, total RNA is extracted with Trizol or RecoverAll™ Total Nucleic Acid Isolation Ambion Kit which is designed for formalin/paraformaldehyde fixed structures (139, 263).

Changes in expression of transcription factors involved in differentiation of myocytes (Nkx2.5, GATA4, MEF2C, Tbx, SRF, HAND-1, HAND-2), smooth muscle cells (GATA6) and endothelial cells (Ets1, Vezf1) are determined. Moreover, mRNA expression of membrane and cytoplasmic components specific of myocytes (connexin 43, N-cadherin, troponin I, atrial and ventricular MLC-2, α- and β-MHC, α-SA), smooth muscle cells (α-SMA, TGF-βR) and endothelial cells (eNOS, CD31, vWf) is studied. For myocyte karyokinesis and cytokinesis, Tsc and Gax expression is determined.

PCR for Y-chromosome DNA: Primers are employed to detect Sry, the sex determining region of the Y-chromosome: dogSry-F: 5'-CGTTGGACGGACAATTCAACCTCGAA-3' SEQ ID NO.: 1 (26 nt, Tm 61° C.) and dogSry-R: 5'-ACCT-GCTTGCATAGCATGGAGGAGGA-3' SEQ ID NO.: 2 (26 nt, Tm 64° C.) [amplicon size: 369 bp].

Immunocytochemistry: These analyses are conducted by confocal microscopy of isolated cells and developing heart to complement the real-time RT-PCR studies.

The results of this set of experiments is expected to show the myocyte progenitor cells will generate predominantly new myocytes of recipient origin, while vascular progenitor cells will generate predominantly smooth muscle cells and endothelial cells of recipient origin. The bone marrow progenitor cells will generate myocytes, smooth muscle cells, and endothelial cells of recipient origin, but are expected to generate fewer numbers of myocytes than myocyte progenitor cells. It is also expected that the generation of immuno-compatible myocardium by the implanted progenitor cells will be comparable to the formation of myocardial tissue during development.

Example 5

Implantation of VPCs and MPCs into the Transplanted Donor Heart Generates Immunocompatible Coronary Vessels and Cardiomyocytes which Together Reconstitute an Immunocompatible Heart The objective of this Example is to utilize therapeutically the two recently identified progenitor cell classes, vascular progenitor cells (VPCs) and myocyte progenitor cells (MPCs), to replace donor myocardium with new recipient myocardium. This approach takes advantage of the vessel regenerative capacity of VPCs and myocyte formation of MPCs to dramatically restructure the transplanted heart. Human studies on cardiac chimerism (14-26) are consistent with this possibility and, in fact, point strongly in this direction. The premise is that resident MPCs and VPCs are preferable and more efficient in creating de novo myocardium than bone marrow progenitor cells (BMPCs) which have to transdifferentiate and acquire a different genetic phenotype (36, 185, 186, 207) before committing to the myocyte and vascular cell lineages (47-57). However, progenitor cells from the explanted organ and/or the bone marrow can be employed to rebuild the donor heart.

Three protocols are used to assess whether the implanted progenitor cells generate functional myocardial tissue and vessels: regional ventricular function, coronary blood flow, and myocyte mechanics.

A. Ventricular Function

The use of a large animal model offers the unique opportunity to instrument the transplanted heart with sonomicrometers and determine chronically the time course of the alterations in regional function and establish whether delivery of progenitor classes results in an improvement of the dyskinetic and hypokinetic segments included within the sonomicrometers (64, 232-237). Recovery of contraction points to myocardial regeneration as one of the possible mechanisms involved, while the lack of amelioration in function suggests absence of tissue reconstitution. The histological examination of the same regions at sacrifice allows us to obtain critical information on the structure and function of the transplanted heart.

B. Coronary Blood Flow (CBF) and Hemodynamics

Figure 18:
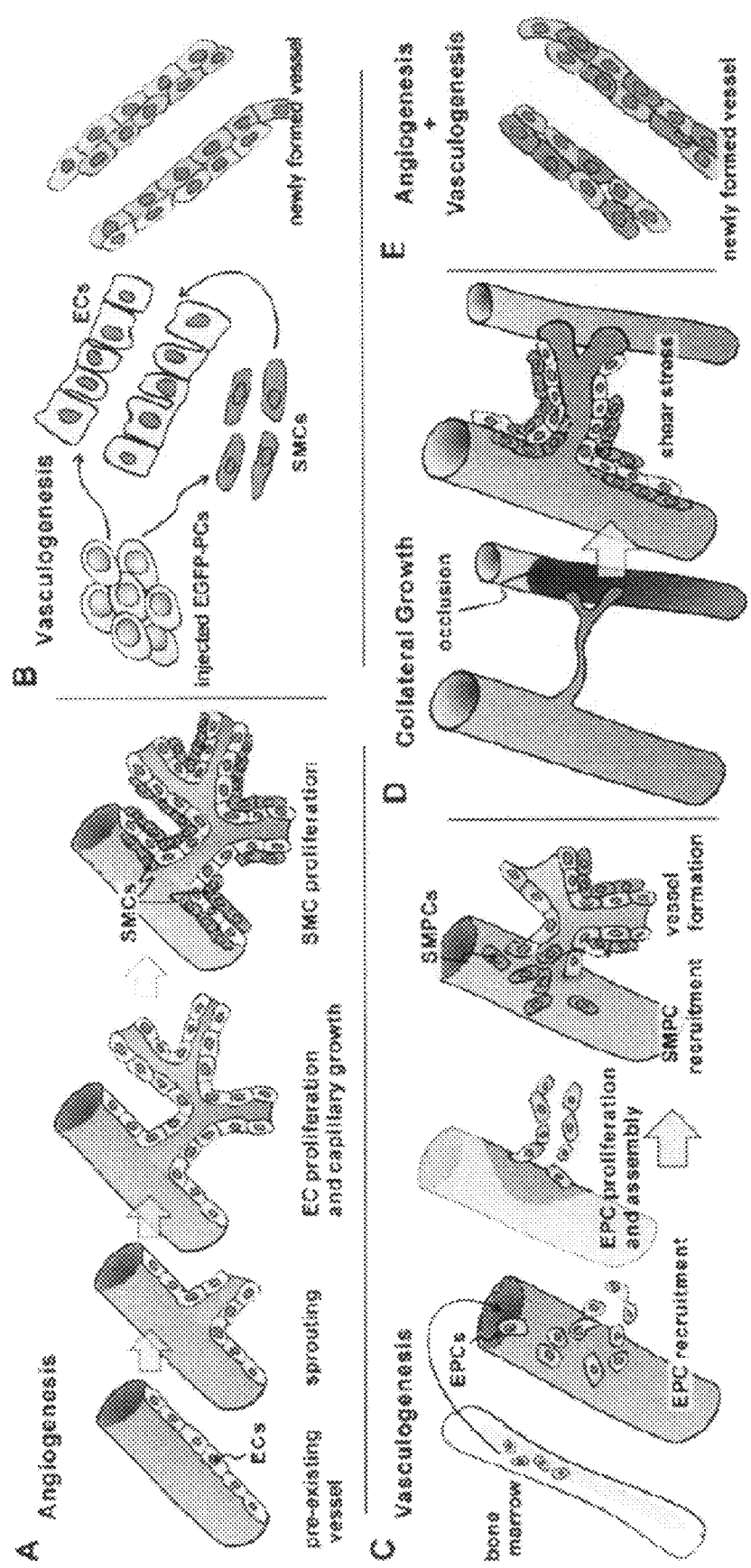
FIG. 18. A: Angiogenesis corresponds to the sprouting of mature ECs and SMCs from pre-existing vessels. Therefore, the cells within the newly formed vessel will not express the reporter genes carried by the injected PCs. B: Vasculogenesis corresponds to sites of active neovascularization and is mediated by the recruitment of the delivered PCs. In this case, the cells in the regenerated vessels will express the reporter genes. C: Alternatively, Vasculogenesis corresponds to the recruitment of circulating EPCs and smooth muscle PCs (SMPCs), which together generate new vessels. In this case, the cells in the vessel wall will be negative for the reporter genes but will carry the Y-chr. D: Adaptive arteriogenesis or collateral vessel formation corresponds to the development of large vessels from pre-existing arteriolar anastomoses. Therefore, the cells within the wall of the collateral vessels will be negative for the reporter genes. E: Combination of angiogenesis and vasculogenesis may also occur resulting in the colocalization of cells negative and positive for the reporter genes within the wall of newly formed vessels.

The potential efficacy of cell therapy requires the inclusion of measurements of CBF distribution and coronary vascular resistance (264-267). If the formation of the various segments of the coronary circulation by BMPCs, VPCs and/or MPCs occurs and cardiac allograft vasculopathy (CAV) is partly corrected, a functional counterpart has to be documented. The collateral circulation of the canine heart protects to a certain extent the myocardium from ischemic events (264-267) so that coronary occlusion may result in hypokinesis instead of dyskinesis of the affected region of the heart (64). Therefore, the potentiation of collateral vessel formation has to be considered and carefully analyzed together with angiogenesis and vasculogenesis to interpret properly functional changes in CBF (FIG. 18). Data are obtained at 10 days after each cell treatment and at sacrifice (264, 265, 268-270).

C. Myocyte Mechanics

An important aspect of the reconstituting myocardium concerns the performance of regenerated myocytes. Thus, parameters of myocyte contractility, calcium handling and L-type calcium current are measured in isolated myocytes and comparisons are made with donor myocytes (40, 57, 59, 139, 271). The acquisition of this information allows us to establish the effective functional competence of regenerated cells (59, 139). Changes in myocyte mechanics which accompany the acquisition of the adult phenotype are assessed and analyzed in myocyte populations derived from different progenitor classes. Thus, the most efficient and powerful myocyte progeny are identified. These measurements are routinely performed (40, 57, 59, 139, 271).

D. Specific Methods

Intervals: As discussed in Example 2, during the course of the study, dogs are anesthetized for left heart catheterization and autologous progenitor cell injection (Group 1; 50% EGFP-labeled VPCs and 50% RFP-labeled MPCs). This protocol is then applied bi-weekly for the next month (Group 2; 50% EGFP-labeled VPCs and 50% β-Gal-labeled MPCs) and subsequently for an additional month (Group 3; 50% EGFP-labeled VPCs and 50% β-Gal-labeled MPCs). Group 1 animals are sacrificed one month after a single cell injection, 2 months after transplantation; Group 2 animals are sacrificed one month after the last of 3 cell injections, 3 months after transplantation; and Group 3 animals are sacrificed one month after the last of 5 cell injections, 4 months after transplantation. Another group of animals, Group 4, is injected bi-weekly for 2 months (5 injections) with 50% MPCs infected with a lentivirus carrying EGFP-Flag-tag under the cardiomyocyte specific α-MHC promoter, RFP-HA-tag under the SMC-specific Sm22a promoter and TFP-c-myc-tag under the EC-specific VE-cadherin promoter. These animals are sacrificed 4 months after transplantation. At most 5 injections of progenitor cells are done in each dog; $2 \times 10^6$ cells are injected each time.

CBF: Two ml of Steri spheres (BioPal) suspension (2 millions/mL) are mixed with arterial blood and injected into left atrium over 5 seconds. Immediately before the injection, arterial blood reference sample is withdrawn from the aortic catheter. At the end of experiment, transmural tissue samples (~1 g) are harvested from cardiac regions of interest and cut into three layers: epicardial, mid-myocardial and endocardial. Tissue and reference blood samples are dried overnight, and then shipped to Bio-Pal for neutron activation and radioactivity counting. The average radioactivity counts for myocardium are calculated as $Ci=(C1 \times W1+C2 \times W2+C3 \times W3)/(W1+W2+W3)$ where Ci is the average count (dpm/g), C1-3 and W1-3 are the counts and wet weights for the epicardium, mid-myocardium, and endocardium layers, respectively. The myocardial flow is calculated as $Qi=(Ci/Cref) \times R(ml/min)$ where Qi is flow, Ci and Cref are the radioactivities in tissue and in blood reference sample, respectively, and R is the withdrawal rate of the reference blood sample. Endocardial/epicardial flow ratio is calculated to obtain an index of regional flow pattern (268-270).

Figure 19:
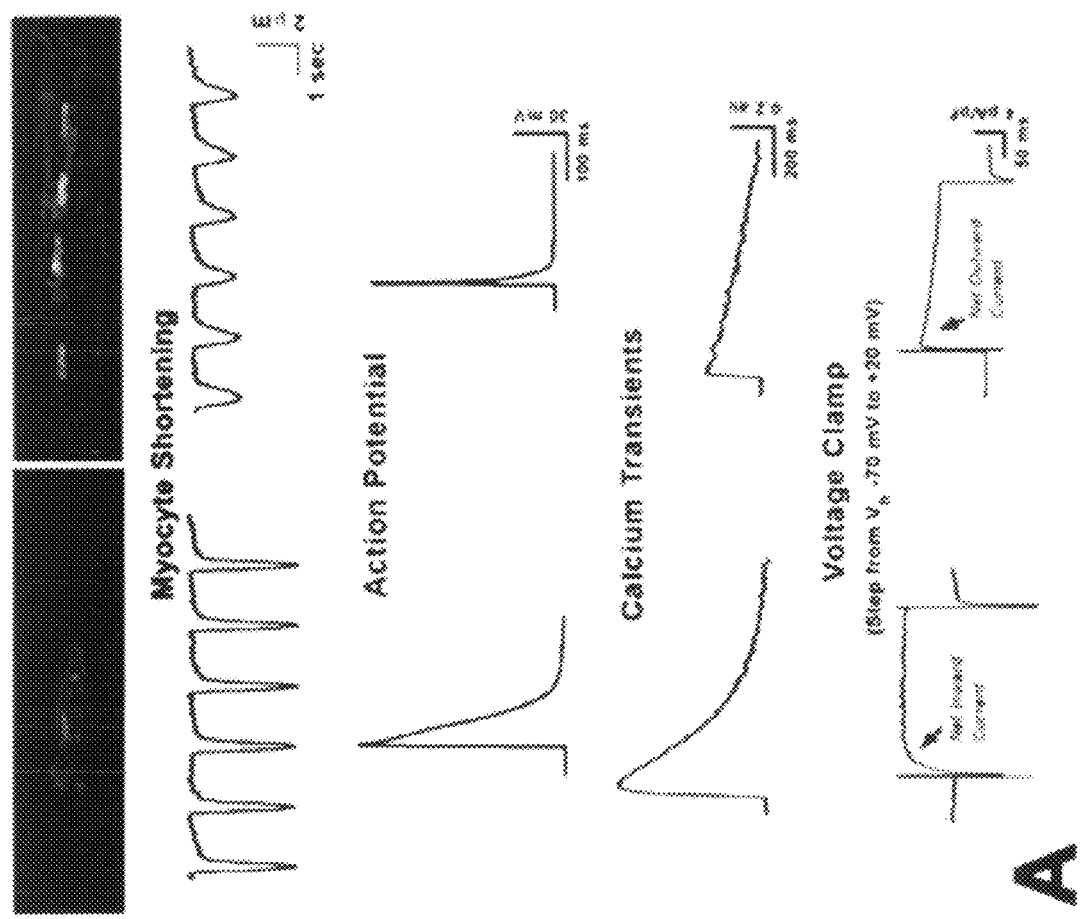
FIG. 19. Physiology of newly generated myocytes. A: Contractility, action potential, calcium transients and voltage clamp currents in a small newly formed (left panel) and a large terminally differentiated (right panel) myocyte. Hypertrophied myocytes exhibit depressed contractility, which is paralleled by shorter action potential, decreased calcium transient and increased net outward current. B: Mechanical properties of myocytes generated by BMPCs injected in the infarcted mouse heart. Newly formed cells show green fluorescence, since BMPCs were obtained from transgenic mice expressing EGFP under the control of α-MHC promoter. Spared hypertrophied myocytes (phase contrast) are characterized by decreased fractional shortening. C: Membrane currents in myocytes generated by BMPCs. In comparison with surviving myocytes, new cells possess higher outward potassium current which, in turn, determines longer duration of the action potential.
Figure 19:
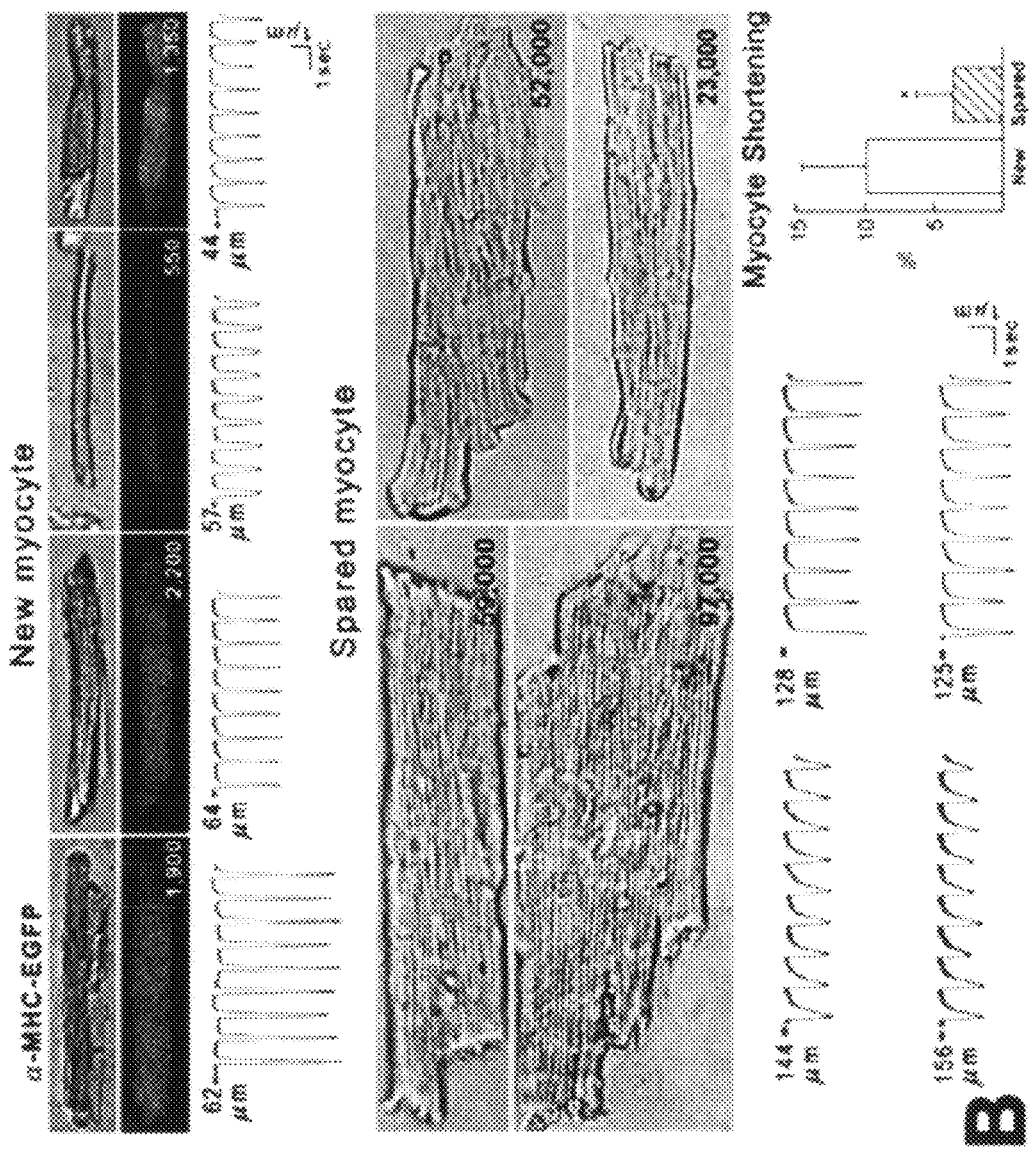
Figure 19C:
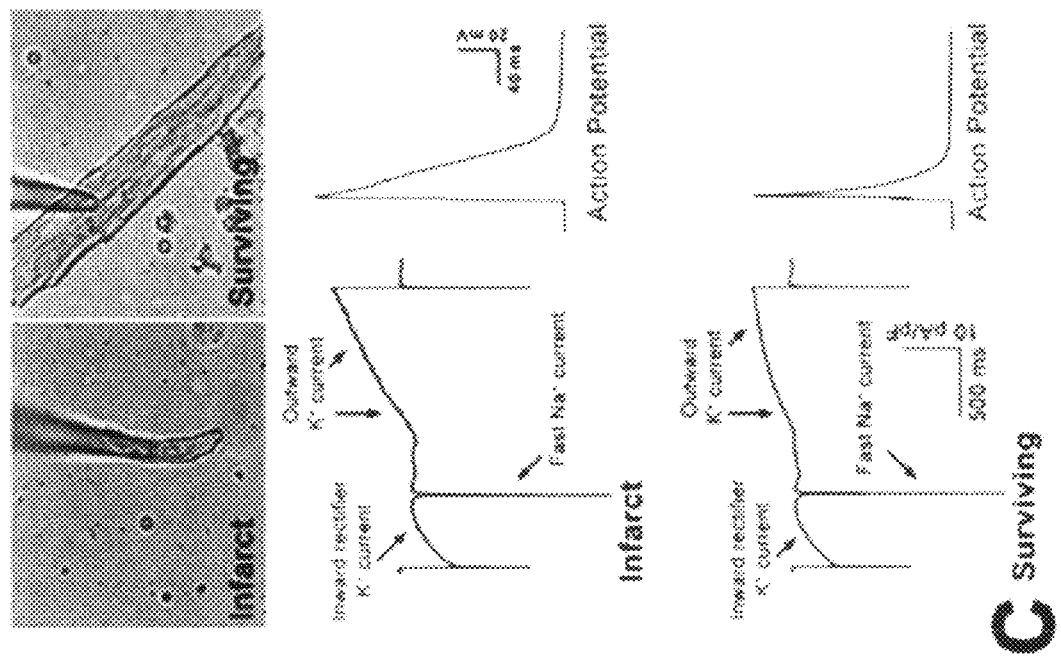

Mechanics, Ca2+ transients and electrophysiology (see FIG. 19): Myocytes are transferred to a chamber placed on the stage of an inverted microscope. External bath Ca2+ is kept at 1.5 mM. Mechanics, Ca2+ transients: Myocytes are stimulated at 1.0 Hz by rectangular depolarizing pulses, 2 ms in duration, and twice-diastolic threshold intensity. Changes in cell length are quantified by edge tracking. Sarcomere length is determined by the mean frequency of sarcomere spacing utilizing the Fast Fourier Transform. Fluo 3-fluorescence is measured by epi-illumination with flashes of 488 nm light. After loading cell with the Ca2+ probe, experiments are performed at 25±0.2° C. to minimize the loss of the Ca2+ indicator. The ability of myocytes to adapt to different rates of stimulation and extracellular Ca2+ concentrations is examined (40, 59). Electrophysiology: Electrical properties of differentiating myocytes are measured in combination with cell shortening. Data are collected by whole cell patch-clamp technique in voltage- and current-clamp mode and by edge motion detection measurements. Voltage, time-dependence and density of L-type Ca2+ current is analyzed in voltage-clamp preparations. T-type Ca2+ current is assessed (265); it is restricted to developing myocytes (272). Relationship between shortening and action potential is done in current-clamp mode (57, 271, 273-280).

The results of these experiments are expected to show that the implanted MPCs will generate predominantly immunocompatible myocytes, while the implanted VPCs will generate predominantly immunocompatible smooth muscle cells and endothelial cells. Some of the smooth muscle cells and endothelial cells derived from the recipient will assemble into functional coronary vessels that may reduce cardiac allograft vasculopathy and enhance coronary blood flow.

Having thus described in detail preferred embodiments of the present invention, it is to be understood that the invention defined by the appended claims is not to be limited by particular details set forth in the above description as many apparent variations thereof are possible without departing from the spirit or scope thereof.

Those skilled in the art will recognize, or be able to ascertain using no more than routine experimentation, many equivalents to the specific embodiments of the invention described herein. Such equivalents are intended to be encompassed by the following claims.

References

1. Lowsky R, Takahashi T, Liu Y P, Dejbakhsh-Jones S, Grumet F C, Shizuru J A, Laport G G, Stockeri-Goldstein K E, Johnston L J, Hoppe R T, Bloch D A, Blume K G, Negrin R S, Strober S: Protective conditioning for acute graft-versus-host disease. N Engl J Med. 353:1321-1331, 2005.
2. Olszewski W L: Innate immunity processes in organ allografting—their contribution to acute and chronic rejection. Ann Transplant. 10:5-9, 2005.
3. Colvin R B, Smith R N: Antibody-mediated organ-allograft rejection. Nat Rev Immunol. 5:807-817, 2005.
4. Al-khaldi A, Robbins R C: New directions in cardiac transplantation. Annu Rev Med. 57:455-471, 2006.
5. Kabashigawa J A, Patel J K: Immunosupression for heart transplantation: where are we now? Nat Clin Pract Cardiovasc Med. 3:203-212, 2006.
6. Starzl T E, Demetris A J, Murase N, Ildstad S, Ricordi C, Trucco M: Cell migration, chimerism, and graft acceptance. Lancet. 339:1579-1582, 1992.
7. Starzl T E, Demetris A J, Trucco M, Ramos H, Zeevi A, Rudert W A, Kocova M, Ildstad S, Murase N: Systemic chimerism in human female recipients of male livers. Lancet. 340:876-877, 1992.
8. Frede S E, Levy A E, Alexander J W, Babcock G F: An examination of tissue chimerism in the ACI to Lewis rat cardiac transplant model. Transp Immunol. 4:227-231, 1996.
9. Kitagawa-Sakakida S, Tori M, Li Z, Horiguchi K, Izutani H, Matsuda H, Shirakura R: Active cell migration in retransplanted rat cardiac allografts during the course of chronic rejection. J Heart Lung Transplant. 19:584-590, 2000.
10. Ichikawa N, Demetris A J, Starzl T E, Ye Q, Okuda T, Chun H J, Liu K, Kim Y M, Murase N: Donor and recipient leukocytes in organ allografts of recipients with variable donor specific tolerance: with particular reference to chronic rejection. Liver Transpl. 6:686-702, 2000.
11. Hruban R H, Long P P, Perlman E J, Hutchins G M, Baumgartner W A, Bauthman K L, Griffin C A: Fluorescence in situ hybridization for the Y-chromosome can be used to detect cells of recipient origin in allografted hearts following cardiac transplantation. Am J Pathol. 142:975-980, 1993.
12. Hessel H, Mitternuller J, Zitzelsberger H, Weier H U, Bauchinger M: Combined immunophenotyping and FISH with sex chromosome-specific DNA probes for the detection of chimerism in epidermal Langerhans cells after sex-mismatched bone marrow transplantation. Histochem Cell Biol. 106:481-485, 1996.
13. Lion T, Watzinger F: Chimerism analysis following non-myeloablative stem cell transplantation. Methods Mol Med. 125:275-295, 2006.
14. Quaini F, Urbanek K, Beltrami A P, Finato N, Beltrami C A, Nadal-Ginard B, Kajstura J, Leri A, Anversa P: Chimerism of the transplanted heart. N Engl J Med. 346:5-15, 2002.
15. LaFlamme M A, Myerson D, Saffitz J E, Murry C E: Evidence for cardiomyocyte repopulation by extracardiac progenitors in transplanted human hearts. Circ Res. 90:634-640, 2002.
16. Thiele J, Varus E, Wickenhauser C, Kvasnicka H M, Metz K, Schaefer U W, Beelen D W: Chimerism of cardiomyocytes and endothelial cells after allogenic bone marrow transplantation in chronic myeloid leukemia. An autopsy study. Pathologe. 23:405-410, 2002.
17. Müller P, Pfeiffer P, Koglin J, Schäfers H J, Seeland U, Janzen I, Urbschat S, Böhm M: Cardiomyocytes of non-cardiac origin in myocardial biopsies of human transplanted hearts. Circulation. 106:31-35, 2002.
18. Bayes-Genis A, Salido M, Ristol F S, Puig M, Brossa V, Campreciós M, Corominas J M, Mariñoso ML, Baró T, Vela M, Serrano S, Padró J, de Luna A B, Cinca J: Host cell-derived cardiomyocytes in sex-mismatch cardiac allografts. Cardiovasc Res. 56:404-410, 2002.
19. Glaser R, Lu M M, Narula N, Epstein J: Smooth muscle cells, but not myocytes, are of host origin in transplanted human hearts. Circulation. 106:17-19, 2002.
20. Deb A, Wang S, Skelding K A, Miller D, Simper D, Caplice N M: Bone marrow-derived cardiomyocytes are present in adult human heart. A study of gender-mismatched bone marrow transplantation patients. Circulation. 107:1245-1247, 2003.
21. Caplice N M, Bunch T J, Stalboerger P G, Wang S, Simper D, Miller D V, Russell S J, Litzow M R, Edwards M D: Smooth muscle cells in human coronary atherosclerosis can originate from cells administered at marrow transplantation. Proc Natl Acad Sci USA. 100: 4754-4759, 2003.
22. Koestner S C, Kappeler A, Schaffner T, Carrel T P, Nydegger U E, Mohacsi P: Histo-blood group type change of the graft from B to O after ABO mismatched heart transplantation. Lancet. 363:1523-1525, 2004.
23. Thiele J, Varus E, Wickenhauser C, Kvasicka H M, Lorenzen J, Gramley F, Metz K A, Rivero F, Beelen D W: Mixed chimerism of cardiomyocytes and vessels after allogeneic bone marrow and stem-cell transplantation in comparison with cardiac allografts. Transplantation. 77:1902-1905, 2004.
24. Höcht-Zeisberg E, Kahnert H, Guan K, Wulf G, Hemmerlein B, Schlott T, Tenderich G, Körfer R, Raute-Kreinsen U, Hasenfuss G: Cellular repopulation of myocardial infarction in patients with sex-mismatched heart transplantation. Eur Heart J. 25:749-758, 2004.
25. Minami E, Laflamme M A, Saffitz J E, Murry C E: Extracardiac progenitor cells repopulate most major cell types in the transplanted human heart. Circulation. 112: 2951-2958, 2005.
26. Pfeiffer P, Muller P, Kazakov A, Kindermann I, Bohm M: Time-dependent cardiac chimerism in gender-mismatched heart transplantation patients. J Am Coll Cardiol. 48:843-845, 2006.
27. Anversa P, Nadal-Ginard B: Cardiac chimerism: methods matter. Circulation. 106:e129-e131, 2002.
28. Anversa P, Nadal-Ginard B: Chimerism of the transplanted heart. N Engl J Med. 346:1411-1412, 2002.
29. Kvasnicka H M, Wickenhauser C, Thiele J: Quantifying chimeric cardiomyocytes. Circulation. 108:e60, 2003.
30. Bolli R: Regeneration of the human heart—No Chimera? N Engl J Med. 346:55-56, 2002.
31. Bayes-Genis A, Roura S, Prat-Vidal C, Farré J, Soler-Botija C, de Luna A B, Cinca J: Chimerism and microchimerism of the human heart: evidence for cardiac regeneration. Nat Clin Pract Cardiovasc Med. 4:S40-45, 2007.
32. Mathur A, Martin J F: Stem cells and repair of the heart. Lancet. 364:183-192, 2004.
33. Körbling M, Estrov Z: Adult stem cells for tissue repair-A new therapeutic concept? N Engl J Med. 349:570-582, 2003.
34. von Harsdorf R, Poole-Wilson P H, Dietz R: Regenerative capacity of the myocardium: implications for treatment of heart failure. Lancet. 363:1306-1313, 2004.

35. Angelini P, Markwald R R: Stem cell treatment of the heart. A review of its current status on the brink of clinical experimentation. Tex Heart Inst J. 32:479-488, 2005.
36. Leri A, Kajstura J, Anversa P: Cardiac stem cells and mechanisms of myocardial regeneration. Physiol Rev. 85:1373-1416, 2005.
37. Schwartz R S, Curfman G D: Can the heart repair itself? N Engl J Med. 346:2-4, 2002.
38. Wagers A J, Weissman I L: Plasticity of adult stem cells. Cell. 116:639-648, 2004.
39. Pomerantz J, Blau H M: Nuclear reprogramming: a key to stem cell function in regenerative medicine. Nat Cell Biol. 6:810-816, 2004.
40. Urbanek K, Rota M, Cascapera S, Bearzi C, Nascimbene A, De Angelis A, Hosoda T, Chimenti S, Baker M, Limana F, Nurzynska D, Torella D, Rotatori F, Rastaldo R, Musso E, Quaini F, Leri A, Kajstura J, Anversa P: Cardiac stem cells possess growth factor-receptor systems that after activation regenerate the infarcted myocardium, improving ventricular function and long-term survival. Circ Res. 97:663-673, 2005.
41. Murry C E, Soonpaa M H, Reinecke H, Nakajima H, Nakajima H O, Rubart M, Pasumarthi K B, Virag J I, Bartelmez S H, Poppa V, Bradford G, Dowell J D, Williams D A, Field L J: Haematopoietic stem cells do not transdifferentiate into cardiac myocytes in myocardial infarcts. Nature. 428:664-668, 2004.
42. Balsam L B, Wagers A J, Christensen J L, Kofidis T, Weissman I L, Robbins R C: Haematopoietic stem cells adopt mature haematopoietic fates in ischaemic myocardium. Nature. 428:668-673, 2004.
43. Nygren J M, Jovinge S, Breitbach M, Sawen P, Roll W, Hescheler J, Taneera J, Fleischmann B K, Jacobsen S E: Bone marrow-derived hematopoietic cells generate cardiomyocytes at a low frequency through cell fusion, but not transdifferentiation. Nat Med. 10:494-501, 2004.
44. Laflamme M A, Murry C E: Regenerating the heart. Nat Biotechnol. 23:845-856, 2005.
45. Rubart M, Field L J: Cardiac regeneration: repopulating the heart. Annu Rev Physiol. 68: 29-49, 2006.
46. Chien K R: Stem cells: lost in translation. Nature. 428:607-608, 2004.
47. Orlic D, Kajstura J, Chimenti S, Jakoniuk I, Anderson S M, Li B, Pickel J, McKay R, Nadal-Ginard B, Bodine D M, Leri A, Anversa P: Bone marrow cells regenerate infarcted myocardium. Nature. 410:701-705, 2001.
48. Orlic D, Kajstura J, Chimenti S, Limana F, Jakoniuk I, Quaini F, Nadal-Ginard B, Bodine D M, Leri A, Anversa P: Mobilized bone marrow cells repair the infarcted heart improving function and survival. Proc Natl Acad Sci USA. 98:10344-10349, 2001.
49. Aicher A, Heeschen C, Mildner-Rihm C, Urbich C, Ihling C, Technau-Ihling K, Zeiher A M, Dimmeler S: Essential role of endothelial nitric oxide synthase for mobilization of stem and progenitor cells. Nat Med. 9:1370-1376, 2003.
50. Kawada H, Fujita J, Kinjo K, Matsuzaki Y, Tsuma M, Miyatake H, Muguruma Y, Tsuboi K, Itabashi Y, Ikeda Y, Ogawa S, Okano H, Hotta T, Ando K, Fukuda K: Non-hematopoietic mesenchymal stem cells can be mobilized and differentiate into cardiomyocytes after myocardial infarction. Blood. 104:3581-3587, 2004.
51. Kajstura J, Rota M, Whang B, Cascapera S, Hosoda T, Bearzi C, Nurzynska D, Kasahara H, Zias E, Bonafe' M, Nadal-Ginard B, Torella D, Nascimbene A, Quaini F, Urbanek K, Leri A, Anversa P: Bone marrow cells differentiate in cardiac cell lineages after infarction independently of cell fusion. Circ Res. 96:127-137, 2005.
52. Yoon Y S, Wecker A, Heyd L, Park J S, Tkebuchava T, Kusano K, Hanley A, Scadova H, Qin G, Cha D H, Johnson K L, Aikawa R, Asahara T, Losordo D W: Clonally expanded novel multipotent stem cells from human bone marrow regenerate myocardium after myocardial infarction. J Clin Invest. 115:326-338, 2005.
53. Murasawa S, Kawamoto A, Horii M, Nakamori S, Asahara T: Niche-dependent translineage commitment of endothelial progenitor cells, not cell fusion in general, into myocardial lineage cells. Arterioscler Thromb Vasc Biol. 25:1388-1394, 2005.
54. Urbich C, Heeschen C, Aicher A, Sasaki K, Bruhl T, Farhadi M R, Vajkoczy P, Hofmann W K, Peters C, Pennacchio L A, Abolmaali N D, Chavakis E, Reinheckel T, Zeiher A M, Dimmeler S: Cathepsin L is required for endothelial progenitor cell-induced neovascularization. Nat Med. 11:206-213, 2005.
55. Urbich C, Aicher A, Heeschen C, Dernbach E, Hofmann W K, Zeiher A M, Dimmeler S: Soluble factors released by endothelial progenitor cells promote migration of endothelial cells and cardiac resident progenitor cells. J Mol Cell Cardiol. 39:733-742, 2005.
56. Mouquet F, Pfister O, Jain M, Oikonomopoulos A, Ngoy S, Summer R, Fine A, Liao R: Restoration of cardiac progenitor cells after myocardial infarction by self-proliferation and selective homing of bone marrow-derived stem cells. Circ Res. 97:1090-1092, 2005.
57. Rota M, Kajstura J, Hosoda T, Bearzi C, Vitale S, Esposito G, Iaffaldano G, Padin-Iruegas M E, Gonzalez A, Rizzi R, Small N, Muraski J, Xiongwen C, Urbanek K, Bolli R, Houser S R, Leri A, Sussman M A, Anversa P: Bone marrow cells to adopt the cardiomyogenic fate in vivo: Proc Natl Acad Sci USA. In press, 2007.
58. Hierlihy A M, Seale P, Lobe C G, Rudnicki M A, Megeney L A: The post-natal heart contains a myocardial stem cell population. FEBS Lett. 530:239-243, 2002.
59. Beltrami A P, Barlucchi L, Torella D, Baker M, Limana F, Chimenti S, Kasahara H, Rota M, Musso E, Urbanek K, Leri A, Kajstura J, Nadal-Ginard B, Anversa P: Adult cardiac stem cells are multipotent and support myocardial regeneration. Cell. 114:763-776, 2003.
60. Oh H, Bradfute S B, Gallardo T D, Nakamura T, Gaussin V, Mishina Y, Pocius J, Michael L H, Behringer R R, Garry D J, Schneider M D: Cardiac progenitor cells from adult myocardium: homing, differentiation, and fusion after infarction. Proc Natl Acad Sci USA. 100:12313-12318, 2003.
61. Matsuura K, Nagai T, Nishigaki N, Oyama T, Nishi J, Wada H, Sano M, Toko H, Akazawa H, Sato H, Nakaya H, Kasanuki H, Komuro I: Adult cardiac Sca-1-positive cells differentiate into beating cardiomyocytes. J Biol Chem. 279:11384-11391, 2004.
62. Martin C M, Meeson A P, Robertson S M, Hawke T J, Richardson J A, Bates S, Goetsch S C, Gallardo T D, Garry D J: Persistent expression of the ATP-binding cassette transporter, Abcg2, identifies cardiac SP cells in the developing and adult heart. Dev Biol. 265:262-275, 2004.
63. Messina E, De Angelis L, Frati G, Morrone S, Chimenti S, Fiordaliso F, Salio M, Battaglia M, Latronico M V G, Coletta M, Vivarelli E, Frati L, Cossu G, Giacomello A: Isolation and expansion of adult cardiac stem cells from human and murine heart. Circ Res. 95:911-921, 2004.
64. Linke A, Muller P, Nurzynska D, Casarsa C, Torella D, Nascimbene A, Castaldo C, Cascapera S, Bohm M, Quaini F, Urbanek K, Leri A, Hintze T H, Kajstura J, Anversa P: Stem cells in the dog heart are self-renewing, clonogenic, and multipotent and regenerate infarcted myocardium, improving cardiac function. Proc Natl Acad Sci USA. 102: 8966-8971, 2005.
65. Pfister O, Mouquet F, Jain M, Summer R, Helmes M, Fine A, Colucci W S, Liao R: CD31− but not CD31+ cardiac side populations cells exhibit functional cardiomyogenic differentiation. Circ Res. 97:52-61, 2005.
66. Laugwitz K L, Moretti A, Lam J, Gruber P, Chen Y, Woodard S, Lin L Z, Cai C L, Lu M M, Reth M, Platoshyn O, Yuan J X, Evans S, Chien K R: Postnatal isl1+ cardioblasts enter fully differentiated cardiomyocyte lineages. Nature. 433:585-587, 2005.
67. Rosenblatt-Velin N, Lepore M G, Cartoni C, Beermann F, Pedrazzini T: FGF-2 controls the differentiation of resident cardiac precursors into functional cardiomyocytes. J Clin Invest. 115:1724-1733, 2005.
68. Tomita Y, Matsumura K, Wakamatsu Y, Matsuzaki Y, Shibuya I, Kawaguchi H, Ieda M, Kanakubo S, Shinmazaki T, Ogawa S, Osumi N, Okano H, Fukuda K: Cardiac neural crest cells contribute to the dormant multipotent stem cell in the mammalian heart. J Cell Biol. 170: 1135-1146, 2005.
69. Oyama T, Nagai T, Wada H, Naito A T, Matsuura K, Iwanaga K, Takahashi T, Goto M, Mikami Y, Yasunda N, Akazawa H, Uezumi A, Takeda S, Komuro I: Cardiac side population cells have a potential to migrate and differentiate into cardiomyocytes in vitro and in vivo. J Cell Biol. 176:329-341, 2007.
70. Smith R R, Barile L, Cho H C, Leppo M K, Hare J M, Messina E, Giacomello A, Abraham M R, Marbán E: Regenerative potential of cardiosphere-derived cells expanded from percutaneous endomyocardial biopsy specimens. Circulation. 115:829-832, 2007.
71. Orosz C G, Pelletier R P: Chronic remodeling pathology in grafts. Curr Opin Immunol. 9:676-680, 1997.
72. Kass M, Haddad H: Cardiac allograft vasculopathy: pathology, prevention, and treatment. Curr Opin Cardiol. 21:132-137, 2006.
73. Libby P, Pober J S: Chronic rejection. Immunity. 14:387-397, 2001.
74. Barry W H: Mechanism of immune-mediated myocyte injury. Circulation. 89:2421-2432, 1994.
75. Taqueti V R, Mitchell R N, Lichtman A H: Protecting the pump: controlling myocardial inflammatory responses. Annu Rev Physiol. 68:67-95, 2006.
76. Julius B K, Attenhofer J C H, Sutsch G, Brunner H P, Kuenzli A, Vogt P R, Turina M, Hess O M, Kiowski W: Incidence, progression and functional significance of cardiac allograft vasculopathy after heart transplantation. Transplantation. 69:847-853, 2000.
77. Bieber C P, Hunt S A, Schwinn D A, Jamieson S A, Reitz B A, Oyer P E, Shumway N E, Stinson E B: Complications in long-term survivors of cardiac transplantation. Transplant Proc. 13:207-211, 1981.
78. Ciliberto G R, Mangiavacchi M, Banfi F, Massa D, Danzi G, Cataldo G, Cipriani M, Piccalo G, Dabala A, Gronda E: Coronary artery disease after heart transplantation: noninvasive evaluation with exercise thallium scintigraphy. Eur Heart J. 14:226-229, 1993.
79. Young Y B: Perspectives on cardiac allograft vasculopathy. Curr Atheroscler Rep. 2:259-271, 2000.
80. Aranda J M Jr, Hill J: Cardiac transplant vasculopathy. Chest. 118:1792-1800, 2000.
81. Tuzcu E M, Kapadia S R, Sachar R, Ziada K M, Crowe T D, Feng J, Magyar W A, Hobbs R E, Starling R C, Young J B, McCarthy P, Nissen S E: Intravascular ultrasound of angiographically silent progression in coronary arthero-sclerosis predicts long-term morbidity and mortality after cardiac transplantation. J Am Coll Cardiol. 45:1538-1542, 2005.
82. Luciani G B, Faggian G, Livi U, Mazzucco A: Variables affecting clinical results after heart transplantation using older donors. Transplant. 24:2681-2683, 1992.
83. Drinkwater D C, Laks H, Blitz A, Kobashigawa J, Sabad A, Moriguchi J, Hamilton M: Outcomes of patients undergoing transplantation with older donor hearts. J Heart Lung Transplant. 15:684-691, 1996.
84. Livi U, Caforio A L, Tursi V, Boffa G M, Borrelli M R, Bauce B, Thiene G, Casarotto D: Donor age greater than 50 years does not influence midterm results of heart transplantation. Transplant Proc. 28:91-92, 1996.
85. Luyt C E, Drobinski G, Dorent R, Ghossoub J J, Collet J P, Choussat R, Dalby M, Thomas D, Gandjbakhch I: Prognosis of moderate coronary artery lesions in heart transplant patients. J Heart Lung Transplant. 22:130-136, 2003.
86. Fellstrom B, Backman U, Larsson E, Wahlberg J: Accelerated atherosclerosis in the transplant recipient: role of hypertension. J Hum Hypertens. 12:851-854, 1998.
87. Bundy R E, Marczin N, Birks E F, Chester A H, Yacoub M H: Transplant atherosclerosis: role of phenotypic modulation of vascular smooth muscle by nitric oxide. Gen Pharmacol. 34:73-84, 2000.
88. Vassali G, Gallino A, Weis M, von Scheidt W, Kappenberger L, von Segesser L K, Goy J J: Alloimmunity and non-immunologic risk factors in cardiac allograft vasculopathy. Eur Heart J. 24:1180-1188, 2003.
89. Weis M, Cooke J P: Cardiac allograft vasculopathy and dysregulation of the NO synthase pathway. Arterioscler Thromb Vasc Biol. 23:567-575, 2003.
90. Alexander R T, Lathrop S, Vollmer R, Blue L, Russel S D, Steenbergen C: Graft vascular disease after cardiac transplantation and its relationship to mean acute rejection score. Arch Pathol Lab Med. 129:1283-1287, 2005.
91. Mehra M R: Contemporary concepts in prevention and treatment of cardiac allograft vasculopathy. Am J Transplant. 6:1248-1256, 2006.
92. Costanzo M R, Naftel D C, Pritzker M R, Heilman J K 3rd, Boehmer J P, Brozena S C, Dec G W, Ventura H O, Kirklin J K, Bourge R C, Miller L W: Heart transplant coronary artery disease detected by coronary angiography: a multi-institutional study of preoperative donor and recipient risk factors. Cardiac Transplant Research Database. J Heart Lung Transplant. 17:744-753, 1998.
93. Yeung A C, Davis S F, Hauptman P J, Kobashigawa J A, Miller L W, Valantine H A, Ventura H O, Wiedermann J, Wilensky R: Incidence and progression of transplant coronary artery disease over 1 year: results of a multicenter trial with the use of intravascular ultrasound. J Heart Lung Transplant. 14:S215-S220, 1995.
94. Geraghty J G, Stoltenberg H W, Sollinger H W, Hullett D A: Vascular smooth muscle cells and neointimal hyperplasia in chronic transplant rejection. Transplantation. 62:502-509, 1996.
95. Amano J, Ishiyama S, Nishikawa T, Tanaka H, Nagai R, Marumo F, Hiroe M: Proliferation of smooth muscle cells in acute allograft vascular rejection. J Thorac Cardiovasc Surg. 113:19-25, 1997.
96. Vos I H, Briscoe D H: Endothelial injury: cause and effect of alloimmune inflammation. Transpl Infect Dis. 0.4:152-159, 2002.
97. Salomon R N, Hughes C C, Schoen F J, Payne D D, Pober J S, Libby P: Human coronary transplantation-associated 98. Mintz G S, Popma J J, Pichard A D, Kent K M, Satler L F, Wong C, Hong M K, Kovach J A, Leon M B: Arterial remodeling after coronary angioplasty: a serial intravascular ultrasound study. Circulation. 94:35-43, 1996.
99. Lim T T, Liang D H, Botas J, Schroeder J S, Oesterle S N, Yeung A C: Role of compensatory enlargement and shrinkage in transplant coronary artery disease. Serial intravascular ultrasound study. Circulation. 95:855-859, 1997.
100. Pethig K, Heublein B, Wahlers T, Haverich A: Mechanism of luminal narrowing in cardiac allograft vasculopathy: inadequate vascular remodeling rather than intimal hyperplasia is the major predictor of coronary artery stenosis. Am Heart J. 135:628-633, 1998.
101. Schwarzacher S P, Uren N G, Ward M R, Schwarzkopf A, Gianetti N, Hung S, Fitzgerald P J, Oesterle S N, Yeung A C: Determinants of coronary remodeling in transplant coronary disease: a simultaneous intravascular ultrasound and Doppler flow study. Circulation. 101: 1384-1389, 2000.
102. Tsutsui H, Ziada K M, Schoenhagen P, Iyisoy A, Magyar W A, Crowe T D, Klingensmith J D, Vince D G, Rincon G, Hobbs R E, Yamagishi M, Nissen S E, Tuzcu E M: Lumen loss in transplant coronary artery disease is a biphasic process involving early intimal thickening and late constrictive remodeling: results from a 5-year serial intravascular ultrasound study. Circulation. 104:653-657, 2001.
103. Tsutsui H, Schoenhagen P, Ziada K M, Crowe T D, Klingensmith J D, Vince D G, Bott-Silverman C, Starling R, Hobbs R E, Young J, Nissen S E, Tuzcu E M: Early constriction or expansion of the external elastic membrane area determines the late remodeling response and cumulative lumen loss in transplant vasculopathy: an intravascular ultrasound study with 4-year follow-up. J Heart Lung Transplant. 22:519-525, 2003.
104. Hosenpud J D, Shipley G D, Wagner C R: Cardiac allograft vasculopathy: current concepts, recent developments, and future directions. J Heart Lung Transplant. 11:9-23, 1992.
105. Mehra M R, Ventura H O, Smart F W, Stapleton D D, Collins T J, Ramee S R, Murgo J P, White C J: New developments in the diagnosis and management of cardiac allograft vasculopathy. Tex Heart Inst J. 22:138-144, 1995.
106. Davis S F, Yeung A C, Meredith I T, Charbonneau F, Ganz P, Selwyn A P, Anderson T J: Early endothelial dysfunction predicts the development of transplant coronary artery disease at 1 year posttransplant. Circulation. 93:457-462, 1996.
107. Behrendt D, Ganz P, Fang J C: Cardiac allograft vasculopathy. Curr Opin Cardiol. 15: 422-429, 2000.
108. Avery R K: Cardiac allograft vasculopathy. N Engl J Med. 349:829-830, 2003.
109. Pinney S, Mancini D: Cardiac allograft vasculopathy: advances in understanding its pathophysiology, prevention, and treatment. Curr Opin Cardiol. 19:170-176, 2004.
110. Hillebrands J L, Flatter F, Rozing J: Origin of vascular smooth muscle cells and the role of circulating stem cells in transplant arteriosclerosis. Arterioscler Thromb Vasc Biol. 22:380-387, 2003.
111. Nieuwenhuis P, Hillebrands J L, Rozing J: Chronic allograft rejection associated vasculopathy and synthetic biodegradable vascular grafts: a lesson to learn? Crit Rev Immunol. 20:85-88, 2000.
112. Sedmak D D, Sharma H M, Czajka C M, Ferguson R M: Recipient endothelialization of renal allografts: an immunohistochemical study utilizing blood group antigens. Transplantation. 46:907-910, 1988.
113. O'Connell J B, Renlund D G, Bristow M R, Hammond E: Detection of allograft endothelial cells of recipient origin following ABO-compatible, non-identical cardiac transplantation. Transplantation. 51:438-442, 1991.
114. Hillebrands J L, van den Hurk B M H, Klatter F A, Popa E R, Nieuwenhuis P, Rozing J: Recipient origin of neointimal vascular smooth muscle cells in cardiac allografts with transplant arteriosclerosis. J Heart Lung Transplant. 19:1183-1192, 2000.
115. Hillebrands J L, Klater F A, van den Hurk B M H, Popa E R, Nieuwenhuis P, Rozing J: Origin of neointimal endothelium and α-actin-positive smooth muscle cells in transplant arteriosclerosis. J Clin Invest. 107:1411-1422, 2001.
116. Lagaaij E L, Cramer-Knijnenburg G F, van Demenade F J, van Es L A, Bruijn J A, van Krieken J H: Endothelial cell chimerism after renal transplantation and vascular rejection. Lancet. 357:33-37, 2001.
117. Hillebrands J L, Klatter F A, van Dijk W D, Rozing J: The bone-marrow does not contribute substantially to host-derived endothelial cell replacement in transplant arteriosclerosis. Nat Med. 8:2-3, 2002.
118. Simper D, Wang S, Deb A, Holmes D, McGregor C, Frantz R, Kushawa S S, Caplice N: Endothelial progenitor cells are decreased in blood and cardiac allograft patient with vasculopathy and endothelial cell of noncardiac origin are enriched in transplant atherosclerosis. Circulation. 107:143-149, 2003.
119. Hasegawa S, Becker G, Nagano H, Libby P, Mitchell R N: Pattern of graft- and host-specific MHC class II expression in long-term murine cardiac allografts: origin of inflammatory vascular wall cells. Am J Pathol. 153:69-79, 1998.
120. Li J, Han X, Jiang J, Zhong R, Williams G M, Pickering J G, Chow L H: Vascular smooth muscle cells of recipient origin mediate intimal expansion after aortic allotransplantation in mice. Am J Pathol. 158:1943-1947, 2001.
121. Sata M, Hirata Y, Nagai R: Circulating recipient cells contribute to graft coronary arteriosclerosis. J Cardiol. 39:48-49, 2002.
122. Shimizu K, Sugiyama S, Aikawa M, Fukumoto Y, Rabkin E, Libby P, Mitchell R N: Host bone-marrow cells are a source of donor intimal smooth-muscle-like cells in murine aortic transplant arteriopathy. Nat Med. 7:738-741, 2001.
123. Saiura A, Sata M, Hirata Y, Nagai R, Makuuchi M: Circulating smooth muscle progenitor cells contribute to atherosclerosis. Nat Med. 7:382-383, 2001.
124. Sata M, Saiura A, Kunisato A, Toja A, Okada S, Tokuhisa T, Hirai H, Makuuchi M, Hirata Y, Nagai R: Hematopoietic stem cells differentiate into vascular cells that participate in the pathogenesis of atherosclerosis. Nat Med. 8:403-409, 2002.
125. Bigaud M, Schraa E O, Andriambeloson E, Lobstein V, Pally C, Kobel T, Bruns C, Zerweis H G: Complete loss of functional smooth muscle cells precedes vascular remodeling in rat aorta allografts. Transplantation. 68:1701-1707, 1999.
126. Rossman P, Lacha J, Lodererova A: Morphology and immunohistochemistry of rat aortic grafts. Folia Microbiol (Praha). 44:339-353, 1999.
127. Olivetti G, Anversa P, Melissari M, Loud A V: Morphometric study of early postnatal development of the thoracic aorta in the rat. Circ Res. 47:417-424, 1980.

128. Olivetti G, Anversa P, Melissari M, Loud A V: Morphometry of medial hypertrophy in the rat thoracic aorta. Lab Invest. 42:559-565, 1980.
129. Anversa P, Capasso J M: Loss of intermediate-sized arteries and capillary proliferation following left ventricular failure in rats. Am J Physiol. 260:H1552-H1560, 1991.
130. Anversa P, Li P, Sonnenblick E H, Olivetti G: Effects of aging on the quantitative structural properties of the coronary vasculature and microvasculature in Fischer 344 rats. Am J Physiol. 267:H1062-H1073, 1994.
131. Bojakowski K, Religa P, Bojakowska M, Hedin U, Gaciong Z, Thyberg J: Arteriosclerosis in rat aortic allografts: early changes in endothelial integrity and smooth muscle phenotype. Transplantation. 70:65-72, 2000.
132. Mennander A, Paavonen T, Hayry P: Intimal thickening and medial necrosis in allograft arteriosclerosis (chronic rejection) are independently regulated. Arterioscler Thromb. 13:1019-1025, 1993.
133. Plissonnier D, Nochy D, Poncet P, Mandet C, Hinglais N, Bariety J, Michel J-B: Sequential immunological targeting of experimental arterial allograft. Transplantation. 60:414-424, 1995.
134. Wenke K, Meiser B, Thiery J, Nagel D, von Scheidt W, Krobot K, Steinbeck G, Seidel D, Reichart B: Simvastatin initiated early after heart transplantation: 8-year prospective experience. Circulation. 107:93-97, 2003.
135. Mancini D, Pinney S, Burkhoff D, LaManca J, Itescu S, Burke E, Edwards N, Oz M, Marks A R: Use of rapamycin slows progression of cardiac transplantation vasculopathy. Circulation. 108:48-53, 2003.
136. Anversa P, Olivetti G: Cellular basis of physiological and pathological myocardial growth. Handbook of Physiology: the Cardiovascular System. The Heart New York: Oxford University Press. pp. 75-144, 2002.
137. Tillmanns J, Rota M, Hosoda T, Misao Y, Esposito G, LeCapitaine N, Siggins R, De Angelis A, Yasuzawa-Amano S, Loredo M, Vitale S, Bearzi C, Bolli R, Urbanek K, Leri A, Kajstura J, Anversa P: Formation of large coronary arteries by cardiac progenitor cells: A biological bypass. Proc Natl Acad Sci USA., in revision, 2007.
138. Bearzi C, Muller P, Amano K, Loredo M, Mosna F, Gatti A, Rimoldi O, Kajstura J, Anversa P, Bolli R. Identification and characterization of cardiac stem cells in the pig heart. Circulation. 114:11-125, 2006.
139. Bearzi C, Rota M, Hosoda T, Tillmanns J, Nascimbene A, De Angelis A, Yasuzawa-Amano S, Trofimova I, Siggins R W, Cascapera S, Beltrami A P, Zias E, Quaini F, Urbanek K, Michler R E, Bolli R, Kajstura J, Leri A, Anversa P: Human cardiac stem cells. Proc Natl Acad Sci USA. 104:14068-14073, 2007.
140. Bolli R, Jneid H, Tang X-L, Dawn B, Rimoldi O, Mosna F, Loredo M, Gatti A, Kajstura J, Leri A, Bearzi C, Abdel-Latif A, Anversa P: Intracoronary administration of cardiac stem cells improves cardiac function in pigs with old infarction. Circulation. 114:II-239, 2006.
141. Fehling H J, Lacaud G, Kubo A, Kennedy M, Robertson S, Keller G, Kouskoff V: Tracking mesoderm induction and its specification to the hemangioblast during embryonic stem cell differentiation. Development. 130:4217-4227, 2003.
142. Kouskoff V, Lacaud G, Schwantz S, Fehling H J, Keller G: Sequential development of hematopoietic and cardiac mesoderm during embryonic stem cell differentiation. Proc Natl Acad Sci USA. 102:13170-13175, 2005.
143. Carmeliet P: Angiogenesis in life, disease and medicine. Nature. 438:932-936, 2005.
144. Coultas L, Chawengsaksophak K, Rossant J: Endothelial cells and VEGF in vascular development. Nature. 438:937-945, 2005.
145. Kattman S J, Huber T L, Keller G M: Multipotent Flk-1+ cardiovascular progenitor cells give rise to the cardiomyocyte, endothelial, and vascular smooth muscle lineages. Dev Cell. 11:723-732, 2006.
146. Reese D E, Mikawa T, Bader D M: Development of the coronary vessel system. Circ Res. 91:761-768, 2002.
147. Wada A M, Willet S G, Bader D: Coronary vessel development: a unique form of vasculogenesis. Arterioscler Thromb Vasc Biol. 23:2138-2145, 2003.
148. Shalaby F, Rossant J, Yamaguchi T P, Gertsenstein M, Wu X F, Breitman M L, Schuh A C: Failure of blood-island formation and vasculogenesis in Flk-1-deficient mice. Nature. 376:62-66, 1995.
149. Shalaby F, Ho J, Standord W L, Fischer K D, Schuh A C, Schwartzx L, Bernstein A, Rossant J: A requirement for Flk1 in primitive and definitive hematopoiesis and vasculogenesis. Cell. 89:981-990, 1997.
150. Yamashita J, Itoh H, Hirashima M, Ogawa M, Nishikawa S, Yurugi T, Naito M, Nakao K, Nishikawa S: Flk 1-positive cells derived from embryonic stem cells serve as vascular progenitors. Nature. 408:92-96, 2000.
151. Ema M, Faloon P, Zhang W J, Hirashima M, Reid T, Standford W L, Orkin S, Choi K, Rossant J: Combinatorial effects of Flk1 and Tal1 on vascular and hematopoietic development in the mouse. Genes Dev. 17:380-393, 2003.
152. Schroeder T, Fraser S T, Ogawa M, Nishikawa S, Oka C, Bornkamm G W, Nishikawa S, Honjo T, Just U: Recombination signal sequence-binding protein Jkappa alters mesodermal cell fate decisions by suppressing cardiomyogenesis. Proc Natl Acad Sci USA. 100:4018-4023, 2003.
153. Motoike T, Markham D W, Rossant J, Sato T N: Evidence for novel fate of Flk1+ progenitor: contribution to muscle lineage. Genesis. 35:153-159, 2003.
154. Huber T L, Kouskoff V, Fehling H J, Palis J, Keller G: Haemangioblast commitment is initiated in the primitive streak of the mouse embryo. Nature. 432:625-630, 2004.
155. Ema M, Takahashi S, Rossant J: Deletion of the selection cassette, but not cis-acting elements, in targeted Flk1-lacZ allele reveals Flk1 expression in multipotent mesodermal progenitors. Blood. 107:111-117, 2006.
156. Wu S M, Fujiwara Y, Cibulsky S M, Clapham D E, Lien C, Schultheiss T M, Orkin S H: Developmental origin of a bipotential myocardial and smooth muscle cell precursor in the mammalian heart. Cell. 127:1-14, 2006.
157. Kinder S J, Tsang T E, Wakamiya M, Sasaki H, Behringer R R, Nagy A, Tam P P: The organizer of the mouse gastrula is composed of a dynamic population of progenitor cells for the axial mesoderm. Development. 128:3623-3634, 2001.
158. Kinder S J, Loebel D A, Tam P P: Allocation and early differentiation of cardiovascular progenitors in the mouse embryo. Trends Cardiovasc Med. 11:177-184, 2001.
159. Minasi M G, Riminucci M, De Angelis L, Borello U, Berarducci B, Innocenzi A, Caprioli A, Sirabella D, Baiocchi M, De Maria R, Boratto R, Jaffredo T, Broccoli V, Bianco P, Cossu G: The meso-angioblast: a multipotent, self-renewing cell that originates from the dorsal aorta and differentiates into most mesodermal tissues. Development. 129:2773-2783, 2002.
160. Jones E A, Crotty D, Kulesa P M, Waters C W, Baron M H, Fraser S E, Dickinson M E: Dynamic in vivo imaging of post-implantation mammalian embryos using whole embryo culture. Genesis. 34:228-235, 2002.

161. Jiang Y, Jahagirdar Bn, Reinhardt R L, Schwartz R E, Keene C D, Ortiz-Gonzalez X R, Reyes M, Lenvik T, Lund T, Blackstad M, Du J, Aldrich S, Lisberg A, Low W C, Largaespada D A, Verfaillie C M: Pluripotency of mesenchymal stem cells derived from adult marrow. Nature. 418: 41-49, 2002.

162. Wollert K C, Drexler H: Clinical applications of stem cells for the heart. Circ Res. 96:151-163, 2005.

163. Srour E F, Jetmore A, Wolber F M, Plett P A, Abonour R, Yoder M C, Orschell-Traycoff C M: Homing, cell cycle kinetics and fate of transplanted hematopoietic stem cells. Leukemia. 15:1681-1684, 2001.

164. Zocchi M R, Poggi A: PECAM-1, apoptosis and CD34+ precursors. Leuk Lymphoma. 45:2205-2213, 2004.

165. Lapidot T, Dar A, Kollet O: How do stem cells find their way home? Blood. 106:1901-1910, 2005.

166. Voermans C, van Hennik P B, van der Schoot C E: Homing of human hematopoietic stem and progenitor cells: new insights, new challenges? J Hematother Stem Cell Res. 10:725-738, 2001.

167. Nilsson S K, Simmons P J: Transplantable stem cells: home to specific niches. Curr Opin Hematol. 11:102-106, 2004.

168. Lanza R, Moore M A, Wakayama T, Perry A C, Shieh J H, Hendrikx J, Leri A, Chimenti S, Monsen A, Nurzynska D, West M D, Kajstura J, Anversa P: Regeneration of the infarcted heart with stem cells derived by nuclear transplantation. Circ Res. 94:820-827, 2004.

169. Urbanek K, Cesselli D, Rota M, Nascimbene A, De Angelis A, Hosoda T, Bearzi C, Boni A, Kajstura J, Anversa P, Leri A: Stem cell niches in the adult mouse heart. Proc Natl Acad Sci USA. 103:9226-9231, 2006.

170. Frisch S M, Ruoslahti E: Integrins and anoikis. Curr Opin Cell Biol. 9:701-706, 1997.

171. Gnecchi M, He H, Liang O D, Melo L G, Morello F, Mu H, Noiseux N, Zhang L, Pratt R E, Ingwall J S, Dzau V J: Paracrine action accounts for marked protection of ischemic heart by Akt-modified mesenchymal stem cells. Nat Med. 11:367-368, 2005.

172. Gnecchi M, He H, Noiseux N, Liang O D, Zhang L, Morello F, Mu H, Melo L G, Pratt Re, Ingwall J S, Dzau V J: Evidence supporting paracrine hypothesis for Akt-modified mesenchymal stem cell-mediated cardiac protection and functional improvement. FASEB J. 20:661-669, 2006.

173. Abbott J D, Huang Y, Liu D, Hickey R, Krause D S, Giordano F J: Stromal cell-derived factor-1 alpha plays a critical role in stem cell recruitment to the heart after myocardial infarction but is not sufficient to induce homing in the absence of injury. Circulation. 110:3300-3305, 2004.

174. Dalakas E, Newsome P N, Harrison D J, Plevris J N: Hematopoietic stem cell trafficking in liver injury. FASEB J. 19:1225-1231, 2005.

175. Ceradini D J, Gurtne G C: Homing to hypoxia: HIF-1 as a mediator of progenitor cell recruitment to injured tissue. Trends Cardiovasc Med. 15:57-63, 2005.

176. Anversa P, Reiss K, Kajstura J, Cheng W, Li P, Sonnenblick E H, Olivetti G: Myocardial infarction and the myocyte IGF1 autocrine system. Eur Heart J. 16:37-45, 1995.

177. Cheng W, Reiss K, Li P, Chun M J, Kajstura J, Olivetti G, Anversa P: Aging does not affect the activation of the myocyte insulin-like growth factor-1 autocrine system after infarction and ventricular failure in Fischer 344 rats. Circ Res. 78:536-546, 1996.

178. Nakamura T, Mizuno S, Matsumoto K, Sawa Y, Matsuda H, Nakamura T: Myocardial protection from ischemia/reperfusion injury by endogenous and exogenous HGF. J Clin Invest. 106:1511-1519, 2000.

179. Nian M, Lee P, Khaper N, Liu P: Inflammatory cytokines and post-myocardial infarction remodeling. Circ Res. 94:1543-1553, 2004.

180. Frangogiannis N G, Entman M L: Chemokines in myocardial ischemia. Trends Cardiovasc Med. 15:163-169, 2005.

181. Yamani M H, Ratliff N B, Cook D J, Tuzcu E M, Uy Y, Hobbs R, Rincon G, Bott-Silverman C, Young J B, Smedira N, Starling R C: Peri-transplant ischemic injury is associated with up-regulation of stromal cell-derived factor-1. J Am Coll Cardiol. 46:1029-1035, 2005.

182. Wang Y, Haider H K H, Ahmad N, Zhang D, Ashraf M: Evidence for ischemia induced host-derived bone marrow cell mobilization into cardiac allografts. J Mol Cell Cardiol. 41:478-487, 2006.

183. Dawn B, Stein A B, Urbanek K, Rota M, Whang B, Rastaldo R, Torella D, Tang X L, Rezazadeh A, Kajstura J, Leri A, Hunt G, Varma J, Prabhu S D, Anversa P, Bolli R: Cardiac stem cells delivered intravascularly traverse the vessel barrier, regenerate infarcted myocardium, and improve cardiac function. Proc Natl Acad Sci USA. 102: 3766-3771, 2005.

184. El-Sawy T, Fahmy N M, Fairchild R L: Chemokines: directing leukocyte infiltration into allografts. Curr Opin Immunol. 14:562-568, 2002.

185. Anversa P, Kajstura J, Leri A, Bolli R: Life and death of cardiac stem cells: a paradigm shift in cardiac biology. Circulation. 113:1451-1463, 2006.

186. Anversa P, Leri A, Kajstura J: Cardiac regeneration. J Am Coll Cardiol. 47:1769-1776, 2006.

187. Feigl E O: Coronary physiology. Physiol Rev. 63:1-205, 1983.

188. Tsai A G, Johnson P C, Intaglietta M: Oxygen gradients in the microcirculation. Physiol Rev. 83:933-963, 2003.

189. Murry C E, Field L J, Menasche P: Cell-based cardiac repair: reflections at the 10-year point. Circulation. 112: 3174-3183, 2005.

190. Rubart M, Field L J: Cardiac regeneration: repopulating the heart. Annu Rev Physiol. 68:29-49, 2006.

191. Ahuja P, Sdek P, MacLellan W R: Cardiac myocyte cell cycle control in development, disease, and regeneration. Physiol Rev. 87:521-544, 2007.

192. Lemischka I R, Jordan C T: The return of clonal marking sheds new light on human hematopoietic stem cells. Nat Immunol. 2:11-12, 2001.

193. Glimm H, Schmidt M, Fischer M, Schwarzwaelder K, Wissler M, Klingenberg S, Prinz C, Waller C F, Lange W, Eaves C J, von Kalle C: Efficient marking of human cells with rapid but transient repopulating activity in autografted recipients. Blood. 106:893-898, 2005.

194. Ando K, Yahata T, Sato T, Miyatake H, Matsuzawa H, Oki M, Miyoshi H, Tsuji T, Kato S, Hotta T: Direct evidence for ex vivo expansion of human hematopoietic stem cells. Blood. 107:3371-3377, 2006.

195. Shi P A, Hematti P, von Kalle C, Dunbar C E: Genetic marking as an approach to studying in vivo hematopoiesis: progress in the non-human primate model. Oncogene. 21:3274-3283, 2002.

196. Kim H J, Tisdale J F, Wu T, Takatoku M, Sellers S E, Zickler P, Metzger M E, Agricola B A, Malley J D, Kato I, Donahue R E, Brown K E, Dunbar C E: Many multipotential gene-marked progenitor or stem cell clones contribute to hematopoiesis in nonhuman primates. Blood. 96:1-8, 2000.

197. Mazurier F, Gan O I, McKenzie J L, Doedens M, Dick J E: Lentivector-mediated clonal tracking reveals intrinsic 197. [continued] heterogeneity in the human hematopoietic stem cell compartment and culture-induced stem cell impairment. Blood. 103:545-552, 2004.
198. Németh T, Tóth J, Balogh L, Jánoki G, Manczur F, Vörös K, Dallos G: Principles of renal transplantation in the dog: A review. Acta Vet Hung. 45:213-226, 1997.
199. Maris M, Sandmaier B M, Maloney D G, McSweeney P A, Woolfrey A, Chauncey T, Shizuru J, Niederwieser D, Blume K G, Forman S, Storb R: Non-myeloablative hematopoietic stem cell transplantation. Transfus Clin Biol. 8:231-234, 2001.
200. Plotnikov A N, Shlapakova I, Szabolcs M J, Danilo P Jr, Lorell B H, Potapova I A, Lu Z, Rosen A B, Mathias R T, Brink P R, Robinson R B, Cohen I S, Rosen M R: Xenografted adult human mesenchymal stem cells provide a platform for sustained biological pacemaker function in canine heart. Circulation. 2007. [epub ahead of print]
201. Kim S J, Ghaleh B, Kudej R K, Huang C H, Hintze T H, Vatner S F: Delayed enhanced nitric oxide-mediated coronary vasodilation following brief ischemia and prolonged reperfusion in conscious dogs. Circ Res. 81:53-59, 1997.
202. Osorio J C, Stanley W C, Linke A, Castellari M, Diep Q N, Panchal A R, Hintze T H, Lopaschuk G D, Recchia F A: Impaired myocardial fatty acid oxidation and reduced protein expression of retinoid X receptor-alpha in pacing-induced heart failure. Circulation. 105:606-612, 2002.
203. Post H, d'Agostino C, Lionetti V, Castellari M, Kang E Y, Altarejos M, Xu X, Hintze T H, Recchia F A: Reduced left ventricular compliance and mechanical efficiency after prolonged inhibition of NO synthesis in conscious dogs. J Physiol. 552:233-239, 2003.
204. Kinugawa S, Post H, Kmainski P M, Zhang X, Xu X, Huang H, Recchia F A, Ochoa M, Wolin M S, Kaley G, Hintze T H: Coronary microvascular endothelial stunning after acute pressure overload in the conscious dog is caused by oxidant processes: the role of angiotensin II type 1 receptor and NAD(P)H oxidase. Circulation. 108:2934-2940, 2003.
205. Quesenberry P J, Dooner G, Dooner M, Colvin G: The stem cell continuum: considerations on the heterogeneity and plasticity of marrow stem cells. Stem Cell Rev. 1:29-36, 2005.
206. Chien K R: Lost and found: cardiac stem cell therapy revisited. J Clin Invest. 116:1838-1840, 2006.
207. Anversa P, Leri A, Rota M, Hosoda T, Bearzi C, Urbanek K, Kajstura J, Bolli R: Concise review: stem cells, myocardial regeneration, and methodological artifacts. Stem Cells. 25:589-601, 2007.
208. Schächinger V, Erbs S, Elsässer A, Haberbosch W, Hamrecht R, Hölschermann H, Yu J, Corti R, Mathey D G, Hamm C W, Wüselbeck T, Assmus B, Tonn T, Dimmeler S, Zeiher A M; REPAIR-AMI Investigators: Intracoronary bone marrow-derived progenitor cells in acute myocardial infarction. N Engl J Med. 355:1210-1221, 2006.
209. Assmus B, Honold J, Schächinger V, Britten M B, Fischer-Rasokat U, Lehmann R, Teupe C, Pistorius K, Martin H, Abolmaali N D, Tonn T, Dimmeler S, Zeiher A M: Transcoronary transplantation of progenitor cells after myocardial infarction. N Engl J Med. 355:1222-1232, 2006.
210. Vitk J A: The behavior of cells during the evaluation of gap junctional intercellular communication by metabolic cooperation assay. Neoplasma. 43:119-123, 1996.
211. Rustom A, Saffrich R, Markovic I, Walther P, Gerdes H H: Nanotubular highways for intercellular organelle transport. Science. 303:1007-1010, 2004.
212. Will E, Klump H, Heffner N, Schwieger M, Schiedlmeier B, Ostertag W, Baum C, Stocking C: Unmodified Cre recombinase crosses the membrane. Nucleic Acids Research. 30: e59, 2002.
213. Wang X, Willenbring H, Akkari Y, Torimaru Y, Foster M, Al-Dhalimy M, Lagasse E, Finegold M, Olson, Grompe M: Cell fusion is the principal source of bone-marrow-derived hepatocytes. Nature. 422:897-901, 2003.
214. Petronczki M, Siomos M F, Nasmyth K: Un ménage á quatre: the molecular biology of chromosome segregation in meiosis. Cell. 112:423-440, 2003.
215. Leri A, Kajstura J, Anversa P: Identity deception: not a crime for a stem cell. Physiology. 20:162-168, 2005.
216. Kajstura J, Leri A, Bolli R, Anversa P: Endothelial progenitor cells: neovascularization or more? J Mol Cell Cardiol. 40:1-8, 2006.
217. Urbanek K, Torella D, Sheikh F, De Angelis A, Nurzynska D, Silvestri F, Beltrami C A, Bussani R, Beltrami A P, Quaini F, Bolli R, Leri A, Kajstura J, Anversa P: Myocardial regeneration by activation of multipotent cardiac stem cells in ischemic heart failure. Proc Natl Acad Sci USA. 102:8692-8697, 2005.
218. Riley R S, Hogan T F, Pavot D R, Forysthe R, Massey D, Smith E, Wright L Jr, Ben-Ezra J M: A pathologist's perspective on bone marrow aspiration and biopsy: I. Performing a bone marrow examination. J Clin Lab Anal. 18:70-90, 2004.
219. Wallenstein S, Zucker C L, Fleiss J L: Some statistical methods useful in circulation research. Circ Res. 47:1-9, 1980.
220. Berenson M L, Levine D M, Rindskopf D: Applied Statistics. Prentice Hall, Englewood Cliffs. 362-418, 1988.
221. Hofmann M, Wollert K C, Meyer G P, Menke A, Arseniev L, Hertenstein B, Ganser A, Knapp W H, Drexler H: Monitoring of bone marrow cell homing into the infracted human myocardium. Circulation. 111:2198-2202, 2005.
222. Urbich C, Heeschen C, Aicher A, Dembach E, Zeiher A M, Dimmeler S: Relevance of monocytic features for neovascularization capacity of circulating endothelial progenitor cells. Circulation. 108:2511-2516, 2003.
223. Bruhl T, Heeschen C, Aicher A, Jadidi A S, Haendeler J, Hoffmann J, Schneider M D, Zeiher A M, Dimmeler S, Rossig L: p21Cip1 levels differentially regulate turnover of mature endothelial cells, endothelial progenitor cells, and in vivo neovascularization. Circ Res. 94:686-692, 2004.
224. Chavakis E, Aicher A, Heeschen C, Sasaki K, Kaiser R, El Makhfi N, Urbich C, Peters T, Scharffetter-Kochanek K, Zeiher A M, Chavakis T, Dimmeler S: Role of beta2-integrins for homing and neovascularization capacity of endothelial progenitor cells. J Exp Med. 201:63-72, 2005.
225. Potente M, Urbich C, Sasaki K, Hofmann W K, Heeschen C, Aicher A, Kollipara R, DePinho R A, Zeiher A M, Dimmeler S: Involvement of Foxo transcription factors in angiogenesis and postnatal neovascularization. J Clin Invest. 115:2382-2392, 2005.
226. Walter D H, Haendeler J, Reinhold J, Rochwalsky U, Seeger F, Honold J, Hoffmann J, Urbich C, Lehmann R, Arenzana-Seisdesdos F, Aicher A, Heeschen C, Fichtlscherer S, Zeiher A M, Dimmeler S: Impaired CXCR4 signaling contributes to the reduced neovascularization capacity of endothelial progenitor cells from patients with coronary artery disease. Circ Res. 97:1142-1151, 2005.
227. Dimmeler S, Zeiher A M: Vascular repair by circulating endothelial progenitor cells: the missing link in atherosclerosis? J Mol Med. 82:671-677, 2004.

228. Urbich C, Dimmeler S: Endothelial progenitor cells functional characterization. Trends Cardiovasc Med. 14:318-322, 2004.

229. Asahara T, Kawamoto A: Endothelial progenitor cells for postnatal vasculogenesis. Am J Physiol. 287:C572-C579, 2004.

230. Aicher A, Zeiher A M, Dimmeler S: Mobilizing endothelial progenitor cells. Hypertension. 45:321-325, 2005.

231. Aicher A, Bearzi C, Rota M, Urbanek K, Leri A, Zeiher A M: Human circulating endothelial progenitor cells differentiate into cardiomyocytes and coronary vessels after infarction in mice. Circulation. 110:II-462, 2006.

232. Liu Y, Cigola E, Cheng W, Kajstura J, Olivetti G, Hintze T H, Anversa P: Myocyte nuclear mitotic division and programmed myocyte cell death characterize the cardiac myopathy induced by rapid ventricular pacing in dogs. Lab Invest. 73:771-787, 1995.

233. Kajstura J, Zhang X, Liu Y, Szoke E, Cheng W, Olivetti G, Hintze T H, Anversa P: The cellular basis of pacing-induced dilated cardiomyopathy. Myocyte cell loss and myocyte cellular reactive hypertrophy. Circulation. 92:2306-2317, 1995.

234. Leri A, Liu Y, Malhotra A, Li Q, Stiegler P, Claudio P P, Giordano A, Kajstura J, Hintze T H, Anversa P: Pacing-induced heart failure in dogs enhances the expression of p53 and p53-dependent genes in ventricular myocytes. Circulation. 97:194-203, 1998.

235. Barlucchi L, Leri A, Dostal D E, Fiordaliso F, Tada H, Hintze T H, Kajstura J, Nadal-Ginard B, Anversa P: Canine ventricular myocytes possess a renin-angiotensin system that is upregulated with heart failure. Circ Res. 88:298-304, 2001.

236. Leri A, Barlucchi L, Limana F, Deptala A, Darzyenkiewicz Z, Hintze T H, Kajstura J, Nadal-Ginard B, Anversa P: Telomerase expression and activity are coupled with myocyte proliferation and preservation of telomeric length in the failing heart. Proc Natl Acad Sci USA. 98:8626-8631, 2001.

237. Cesselli D, Jakoniuk I, Barlucchi L, Beltrami A P, Hintze T H, Nadal-Ginard B, Kajstura J, Leri A, Anversa P: Oxidative stress-mediated cardiac cell death is a major determinant of ventricular dysfunction and failure in dog dilated cardiomyopathy. Circ Res. 89:279-286, 2001.

238. Gonzalez A, Rota M, Nurzynska D, Misao Y, Tillmanns J, Ojaimi C, Padin-Iruegas M E, Müller P, Esposito G, Bearzi C, Vitale S, Dawn B, Math S, Baker M, Hintze T H, Bolli R, Urbanek K, Hosoda T, Anversa P, Kajstura J, Leri A: Activation of cardiac progenitor cells reverses the failing heart senescent phenotype and prolongs lifespan. Submitted, 2007.

239. Hakuno D, Fukuda K, Makino S, Konishi F, Tomita Y, Manabe T, Suzuki Y, Umezawa A, Ogawa S: Bone marrow-derived regenerated cardiomyocytes (CMG cells) express functional adrenergic and muscarinic receptors. Circulation. 105:380-386, 2002.

240. Eisenberg L M, Burns L, Eisenberg C A: Hematopoietic cells from bone marrow have the potential to differentiate into cardiomyocytes in vitro. Anat Rec A Discov Mol Cell Evol Biol. 272:870-882, 2003.

241. Badorff C, Brandes R P, Popp R, Rupp S, Urbich C, Aicher A, Fleming I, Busse R, Zeiher A M, Dimmeler S: Transdifferentiation of blood-derived human adult endothelial progenitor cells into functionally active cardiomyocytes. Circulation. 107:1024-1032, 2003.

242. Cossu G, Bianco P: Mesoangioblasts—vascular progenitors for extravascular mesodermal tissues. Curr Opin Genet Dev. 13:537-542, 2003.

243. Sampaolesi M, Biressi S, Tonlorenzi R, Innocenzi A, Draghici E, Cusella de Angelis M G, Cossu G: Cell therapy of primary myopathies. Arch Ital Biol. 143:235-242, 2005.

244. Hristov M, Erl W, Weber P C: Endothelial progenitor cells: isolation and characterization. Trends Cardiovasc Med. 13:201-206, 2003.

245. Ishikawa M, Asahara T: Endothelial progenitor cell culture for vascular regeneration. Stem Cells Dev. 13:344-349, 2004.

246. Hosoda T, Yasuzawa-Amano S, Amano K, Bearzi C, Rota M, Kajstura J, Anversa P, Leri A: Genetic tagging documents the multipotentiality of human cardiac progenitor cells in vivo. Submitted, 2007.

247. Olson E N: A genetic blueprint for growth and development of the heart. Harvey Lect. 98:41-64, 2002-2003.

248. Olson E N: Gene regulatory networks in the evolution and development of the heart. Science. 313:1922-1927, 2006.

249. Lien C L, Schebesta M, Makino S, Weber G J, Keating M T: Gene expression analysis of zebrafish heart regeneration. PloS Biol. 4 e260, 2006.

250. Poss K D: Getting to the heart of regeneration in zebrafish. Semin Cell Dev Biol. 18:36-45, 2007.

251. Karamboulas C, Dakubo G D, Liu J, De Repentigny Y, Yutzey K, Wallace V A, Kothary R, Skerjanc I S: Disruption of MEF2 activity in cardiomyoblasts inhibits cardiomyogenesis. J Cell Sci. 119:4315-4321, 2006.

252. Moskowitz I P, Kim J B, Moore M L, Wolf C M, Peterson M A, Shendure J, Nobrega M A, Yokota Y, Berul C, Izumo S, Seidman J G, Seidman C E: A molecular pathway including Id2, Tbx5, and Nkx2-5 required for cardiac conduction system development. Cell. 129:1365-1376, 2007.

253. Dunwoodie S L: Combinatorial signaling in the heart orchestrates cardiac induction, lineage specification and chamber formation. Semin Cell Dev Biol. 18:54-66, 2007.

254. Owens G K, Kumar M S, Wamhoff B R: Molecular regulation of vascular smooth muscle cell differentiation in development and disease. Physiol Rev. 84:767-801, 2004.

255. Yoshida T, Owens G K: Molecular determinants of vascular smooth muscle cell diversity. Circ Res. 96:280-291, 2005.

256. Atkins G B, Jain M K: Role of Krüppel-like transcription factors in endothelial biology. Circ Res. 100:1686-1695, 2007.

257. Kuhnert F, Campagnolo L, Xiong J W, Lemons D, Fitch M J, Zou Z, Kiosses W B, Gardner H, Stuhlmann H: Dosage-dependent requirement for mouse Vezf1 in vascular system development. Dev Biol. 283:140-156, 2005.

258. Soonpaa M H, Kim K K, Pajak L, Franklin M, Field L J: Cardiomyocyte DNA synthesis and binucleation during murine development. Am J Physiol. 271:H2183-H2189, 1996.

259. Pajak L, Jin F, Xiao G H, Soonpaa M H, Field L J, Yeung R S: Sustained cardiomyocyte DNA synthesis in whole embryo cultures lacking the TSC2 gene product. Am J Physiol. 273: H1619-H1629, 1997.

260. Pasumarthi K B, Nakajima H, Nakajima H O, Jing S, Field L J: Enhanced cardiomyocyte DNA synthesis during myocardial hypertrophy in mice expressing a modified TSC2 transgene. Circ Res. 86:1069-1077, 2000.

261. Kustikova O, Fehse B, Modlich U, Yang M, Düllmann J, Kamino K, von Neuhoff N, Schlegelberger B, Li Z, Baum C: Clonal dominance of hematopoietic stem cells triggered by retroviral gene marking. Science. 308:1171-1174, 2005.

262. Huang W Y, Aramburu J, Douglas P S, Izumo S: Transgenic expression of green fluorescence protein can cause dilated cardiomyopathy. Nat Med. 6:482-483, 2000.
263. Boni A, Nascimbene A, Urbanek K, Delucchi F, Gonzalez A, Siggins R, Amano K, Yasuzawa-Amano S, Ojaimi C, Rota M, Hosoda T, Anversa P, Kajstura J, Leri A: Notch1 receptor enhances myocyte differentiation of cardiac progenitor cells and myocardial regeneration after infarction. Submitted, 2007.
264. Kinugawa S, Post H, Kaminski P M, Zhang X, Xu X, Huang H, Recchia F A, Ochoa M, Wolin M S, Kaley G, Hintze T H: Coronary microvascular endothelial stunning after acute pressure overload in the conscious dog is caused by oxidant processes: the role of angiotensin II type 1 receptor and NAD(P)H oxidase. Circulation. 108:2934-2940, 2003.
265. Post H, d'Agostino C, Lionetti V, Castellari M, Kang E Y, Altarejos M, Xu X, Hintze T H, Recchia F A: Reduced left ventricular compliance and mechanical efficiency after prolonged inhibition of NO synthesis in conscious dogs. J Physiol. 552:233-239, 2003.
266. Lei B, Matsuo K, Labinskyy V, Sharma N, Chandler M P, Ahn A, Hintze T H, Stanley W C, Recchia F A: Exogenous nitric oxide reduces glucose transporters translocation and lactate production in ischemic myocardium in vivo. Proc Natl Acad Sci USA. 102:6966-6971, 2005.
267. Kersten J R, Pagel P S, Warltier D C: Protamine inhibits coronary collateral development in a canine model of repetitive coronary occlusion. Am J Physiol. 268: H720-H728, 1995.
268. Bernstein R D, Ochoa F Y, Xu X, Forfia P, Shen W, Thompson Cl, Hintze T H: Function and production of nitric oxide in the coronary circulation of the conscious dog during exercise. Circ Res. 79:840-848, 1996.
269. Kim S J, Ghaleh B, Kudej R K, Huang C H, Hintze T H, Vatner S F: Delayed enhanced nitric oxide-mediated coronary vasodilation following brief ischemia and prolonged reperfusion in conscious dogs. Circ Res. 81:53-59, 1997.
270. Osorio J C, Stanley W C, Linke A, Castellari M, Diep Q N, Panchal A R, Hintze T H, Lopaschuk G D, Recchia F A: Impaired myocardial fatty acid oxidation and reduced protein expression of retinoid X receptor-alpha in pacing-induced heart failure. Circulation. 105: 606-612, 2002.
271. Rota M, Boni A, Urbanek K, Padin-Iruegas M E, Kajstura T J, Fiore G, Kubo H, Sonnenblick E H, Musso E, Houser S R, Leri A, Sussman M A, Anversa P: Nuclear targeting of Akt enhances ventricular function and myocyte contractility. Circ Res. 97:1332-1341, 2005.
272. Ferron L, Capuano V, Deroubaix E, Coulombe A, Renaud J F: Functional and molecular characterization of a T-type Ca(2+) channel during fetal and postnatal rat heart development. J Mol Cell Cardiol. 34:533-546, 2002.
273. Yao A, Spitzer K W, Ito N, Zaniboni M, Lorell B H, Barry W H: The restriction of diffusion of cations at the external surface of cardiac myocytes varies between species. Cell Calcium. 22:431-438, 1997.
274. Zaniboni M, Yao A, Barry W H, Musso E, Spitzer K W: Complications associated with rapid caffeine application to cardiac myocytes that are not voltage clamped. J Mol Cell Cardiol. 30:2229-2235, 1998.
275. Stilli D, Sgoifo A, Macchi E, Zaniboni M, De Lasio S, Cerbai E, Mugelli A, Lagrasta C, Olivetti G, Musso E: Myocardial remodeling and arrhythmogenesis in moderate cardiac hypertrophy in rats. Am J Physiol. 280:H142-H150, 2001.
276. Loutzenhiser R, Chilton L, Trottier G: Membrane potential measurements in renal afferent and efferent arterioles: actions of angiotensin II. Am J Physiol. 273:F307-F314, 1997.
277. Jackson W F: Ion channels and vascular tone. Hypertension. 35:173-178, 2000.
278. Hill M A, Zou H, Potocnik S J, Meininger G A, Davis M J: Arteriolar smooth muscle mechanotransduction: Ca(2+) signaling pathways underlying myogenic reactivity. J Appl Physiol. 91:973-983, 2001.
279. Hansen P B, Jensen B L, Andreasen D, Skott O: Differential expression of T- and L-type voltage-dependent calcium channels in renal resistance vessels. Circ Res. 89:630-638, 2001.
280. Rota M, Hosoda T, De Angelis A, Arcarese M L, Esposito G, Rizzi R, Tillmanns J, Tugal D, Musso E, Rimoldi O, Bearzi C, Urbanek K, Anversa P, Leri A, Kajstura J: The young mouse heart is composed of myocytes heterogeneous in age and function. Circ Res. 101:387-399, 2007.

The invention claimed is:

1. A method of reducing an immune response to a transplanted donor heart in a recipient subject comprising
administering isolated adult cardiac progenitor cells to the transplanted donor heart, wherein said adult cardiac progenitor cells are isolated from the recipient subject's myocardial tissue and are lineage negative and c-kit positive, and wherein said cardiac progenitor cells generate immunocompatible myocardium and immunocompatible myocardial vessels following their administration, thereby reducing the immune response to said transplanted donor heart.

2. The method of claim 1, wherein prior to administration, said cardiac progenitor cells are separated into vascular progenitor cells and myocyte progenitor cells, wherein said vascular progenitor cells and said myocyte progenitor cells are each expanded in culture to obtain pure cultures of each of said vascular progenitor cells and said myocyte progenitor cells, and each are subsequently administered to said transplanted donor heart, wherein said vascular progenitor cells are vascular endothelial growth factor receptor 2 (VEGFR2) positive and differentiate into immunocompatible endothelial cells and smooth muscle cells, and wherein said myocyte progenitor cells are VEGFR2 negative and differentiate into immunocompatible cardiomyoctyes.

3. The method of claim 1, further comprising exposing the cardiac progenitor cells to one or more cytokines prior to administration.

4. The method of claim 3, wherein said cardiac progenitor cells are activated by exposing the cells to one or more cytokines.

5. The method of claim 1, wherein said subject is human.

6. The method of claim 1, further comprising administering to the subject an immunosuppressive therapy.

7. A method of reducing an immune response to a transplanted donor heart in a recipient subject comprising
administering isolated myocyte progenitor cells to the transplanted donor heart, wherein said myocyte progenitor cells are isolated from the recipient subject's myocardial tissue and are lineage negative, c-kit positive, and VEGFR2 negative, and wherein said myocyte progenitor cells generate immunocompatible myocardium following their administration, thereby reducing the immune response to said transplanted donor heart.

8. The method of claim 7, wherein said myocyte progenitor cells differentiate into immunocompatible cardiomyocytes.

9. The method of claim 7, further comprising administering to the subject an immunosuppressive therapy.

10. A method of reducing cardiac allograft vasculopathy in a subject who has received a transplanted donor heart comprising
administering isolated vascular progenitor cells to the transplanted donor heart, wherein said vascular progenitor cells are isolated from the recipient subject's myocardial tissue and are lineage negative, c-kit positive, and VEGFR2 positive, and wherein said vascular progenitor cells generate immunocompatible coronary vasculature, thereby repairing/and or regenerating the non-immunocompatible coronary arteries of the donor heart.

11. The method of claim 10, wherein said vascular progenitor cells differentiate into immunocompatible endothelial cells and smooth muscle cells.

12. The method of claim 10, further comprising administering to the subject an immunosuppressive therapy.

13. The method of claim 1, wherein said cardiac progenitor cells are expanded in culture prior to administration to the donor heart.

14. The method of claim 7, wherein said myocyte progenitor cells are expanded in culture prior to administration to the donor heart.

15. The method of claim 10, wherein said vascular progenitor cells are expanded in culture prior to administration to the donor heart.

16. The method of claim 1, wherein said adult cardiac progenitor cells are administered to the transplanted donor heart by intramyocardial or intracoronary injection.

17. The method of claim 7, wherein said myocyte progenitor cells are administered to the transplanted donor heart by intramyocardial or intracoronary injection.

18. The method of claim 10, wherein said vascular progenitor cells are administered to the transplanted donor heart by intramyocardial or intracoronary injection.

19. The method of claim 2, wherein said pure vascular progenitor cells are administered simultaneously with said pure myocyte progenitor cells.

20. The method of claim 2, wherein said pure vascular progenitor cells are administered after administration of said pure myocyte progenitor cells.

* * * * *